US012209090B2

(12) United States Patent
Baati et al.

(10) Patent No.: US 12,209,090 B2
(45) Date of Patent: Jan. 28, 2025

(54) 3,6-DISUBSTITUTED-2-PYRIDINALDOXIME SCAFFOLDS

(71) Applicants: Centre National de la Recherche Scientifique, Paris (FR); Université de Strasbourg, Strasbourg (FR); ETAT FRANCAIS (Ministère des armées), representé par la Direction Centrale du Service de Santé des Armées, Paris (FR)

(72) Inventors: Rachid Baati, Strasbourg (FR); Richard Brown, Hampshire (GB); José Dias, Brétigny sur Orge (FR); Alex Maryan-Instone, Bedfordshire (GB); Jagadeesh Yerri, Strasbourg (FR)

(73) Assignees: CENTRE NATIONAL DE LA RECHERCHE SCIENTIFIQUE, Paris (FR); UNIVERSITÉ DE STRASBOURG, Strasbourg (FR); ETAT FRANCAIS (MINISTÈRE DES ARMÉES), REPRESENTE PAR LA DIRECTION CENTRALE DU SERVICE DE SANTÉ DES ARMEES, Paris (FR)

( * ) Notice: Subject to any disclaimer, the term of this patent is extended or adjusted under 35 U.S.C. 154(b) by 816 days.

(21) Appl. No.: 17/430,876

(22) PCT Filed: Feb. 14, 2020

(86) PCT No.: PCT/EP2020/053947
§ 371 (c)(1),
(2) Date: Aug. 13, 2021

(87) PCT Pub. No.: WO2020/165432
PCT Pub. Date: Aug. 20, 2020

(65) Prior Publication Data

US 2022/0081442 A1 Mar. 17, 2022

(30) Foreign Application Priority Data

Feb. 15, 2019 (EP) .................................... 19305185

(51) Int. Cl.

| | |
|---|---|
| ***C07D 473/34*** | (2006.01) |
| ***A61P 25/00*** | (2006.01) |
| ***C07D 213/42*** | (2006.01) |
| ***C07D 213/78*** | (2006.01) |
| ***C07D 401/06*** | (2006.01) |
| ***C07D 473/02*** | (2006.01) |
| ***C07D 519/00*** | (2006.01) |

(52) U.S. Cl.
CPC ......... *C07D 473/34* (2013.01); *C07D 213/42* (2013.01); *C07D 401/06* (2013.01); *C07D 473/02* (2013.01); *C07D 519/00* (2013.01)

(58) Field of Classification Search
CPC .. C07D 473/34; C07D 213/42; C07D 213/78; C07D 401/06; C07D 473/02; C07D 519/00; A61P 25/00
See application file for complete search history.

(56) References Cited

U.S. PATENT DOCUMENTS

2010/0204236 A1 8/2010 Dobbelaar

FOREIGN PATENT DOCUMENTS

| | | | |
|---|---|---|---|
| EP | 3331859 | A1 | 6/2018 |
| WO | 2017/021319 | A1 | 2/2017 |
| WO | 2017184996 | A1 | 10/2017 |
| WO | 2018151830 | A1 | 8/2018 |
| WO | 2018181830 | A1 | 8/2018 |
| WO | 2019076986 | A1 | 4/2019 |

OTHER PUBLICATIONS

Mercey et al.; "First efficient uncharged reactivators for the dephosphylation of poisoned human acetylcholinesterase"; Chemical Communications, vol. 47, No. 18, Mar. 31, 2011, pp. 5295-5297.
Yerri et al.; "Sonogashira Reaction of Bromofluoropyridinaldoxime Nuclei: Convergent Synthesis of Functionalized 2- and 3-Fluoropyridine Scaffolds"; European Journal of Organic Chemistry, vol. 30, Jun. 8, 2018, pp. 4161-4165.
Mercey G. et al. Accounts of Chemical Research, 2012, vol. 45 (5), 756-766.
L. Zhang et al., Biorg. Med. Chem. Lett. 2016, 26, 778-781.
Quinodoz, P. et al., "N-Arylazetidines: Preparation through Anionic Ring Closure", J. Org. Chem. 2016, 81, 2899-2910.
Couty et al., Chem. Comms. 2016, 52, 10072-10075.
Margolis, B. J. et al., J. Org. Chem. 2007, 72, 2232-2235.
Levesque et al. J. Org. Chem. 2017, 82, 5046-5067.
Musonda, C. C et al. Bioorg. Med. Chem. Lett. 2007, 17, 4733-4736.
Madrid, P. et al. Bioorg. Med. Chem. Lett. 2005, 15, 1015-1018.
Lauer et al. J. Am. Chem. Soc., 1946, 68, 1268.
Biannic, B.. et al. Org. Lett. 2013, 15, 2730-2733.
Choikhi et al. Chem. Comms. 2010, 46, 5476-5478.
Trabocchi et al. J. Med. Chem. 2010, 53, 7119-7128.

(Continued)

*Primary Examiner* — Sun Jae Yoo
(74) *Attorney, Agent, or Firm* — WC&F IP

(57) ABSTRACT

The present invention relates to a compound of formula (I), or one of its pharmaceutically acceptable salts: (I) wherein R1, R2 and —X—Y— have specific definitions. It also relates to the use of such a compound in therapy; and to a process for preparing it.

(I)

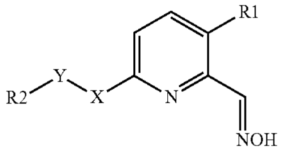

15 Claims, No Drawings

(56) References Cited

OTHER PUBLICATIONS

Tsunoda, T. et al. Tet. Letts., 1993, 34, 1639-1642.
Debnath, J. et al. Bioorg. Med. Chem. 2010, 18, 8257-8263.
Fernicola et al. J. Med. Chem. 2015, 58, 8269-8284.
Behera et al. Chem. Eur. J. 2015, 21, 10179-10184.
European Journal of Medicinal Chemistry, 2014, vol. 78, 455-467.
J. Med. Chem., 2018, vol. 61, 7630-7639.
Carletti et al. J Am Chem Soc, 2008, vol. 130 (47), 1601 1-20.
Zhao Wei and Yan-qin Liu, Sheng-zheng Wang and Lin Yao, Hui-fang Nie, and Yong-an Wang and Xue-Ying LiuZhi-bing Zheng, SongLi, Conjugates of salicylaldoximes and peripheral site ligands: Novel efficient nonquaternary reactivators fornerve agent-inhibited acetylcholinesterase, Bioorganic & Medicinal Chemistry, NL, Elsevier Ltd, Jun. 27, 2017, 25 (16), 4497-4505.
Yerri, J. & Baati, R., “Sonogashira Reaction of Bromofluoropyridinaldoxime Nuclei: Convergent Synthesis of Functionalized 2- and 3-Fluoropyridine Scaffolds”, European Journal of Organic Chemistry, 2018.

3,6-DISUBSTITUTED-2-PYRIDINALDOXIME SCAFFOLDS

The present invention relates to novel compounds having a 3,6-disubstituted-2-pyridinaldoxime scaffold. Such compounds may be useful for many therapeutic and non-therapeutic applications. The invention also relates to compositions, notably pharmaceutical compositions, comprising said compounds, and their uses.

Organophosphorous nerve agents (OPNA) are extremely toxic compounds that comprise chemical warfare agents (CWA) including Sarin, Soman, Cyclosarin, Tabun, O-ethyl S-[2-(diisopropylamino)ethyl] methylphosphonothioate (VX) and pesticides such as Paraoxon, Parathion and tetraethyl pyrophosphate (TEPP). Their acute toxicity results from the irreversible inhibition of acetylcholinesterase (AChE) through phosphorylation of its catalytic serine, which results in the inability of the enzyme to hydrolyze acetylcholine (ACh). Accumulation of this neurotransmitter at cholinergic synapses occurs, leading to permanent saturation of the muscarinic and nicotinic receptors, which ultimately results in seizure and respiratory arrest. Depending on the class of OPNA and the administrated dose, death can occur within a few minutes.

Due to the similarity between the chemical precursors of CWAs and pesticides and the relatively simple chemistry involved in their synthesis, efforts to control the proliferation of these agents have proved to have had limited success. Therefore, the development of effective measures to counteract OPNA poisoning remains a challenging issue to protect and treat both civilian and military populations. The current treatment for OPNA poisoning consists of the administration of a combination of Atropine (antimuscarinic agent) and Diazepam (anticonvulsant drug) and a standard pyridinium oxime (Pralidoxime or 2-PAM, Trimedoxime, HI-6, Obidoxime, or HLö-7) to reactivate AChE. Oximes exert their action on OPNA-inhibited AChE by attacking the phosphorous atom of the phosphorylated serine, leading to the removal of the phosphonate and restoration of the enzyme's catalytic activity. The hybrid reactivator compounds bear a pyridinium oxime-based structure coupled to a potential ligand for the peripheral site of the enzyme termed a peripheral site ligand (PSL). Its purpose is to increase the affinity of the reactivator for AChE (Mercey G. et al., Accounts of Chemical Research, 756-766, 2012, Vol. 45, No. 5).

The efficiency of reactivators may be estimated by the second-order rate constant for reactivation $k_{r2}$, which is the ratio of the maximal reactivation rate constant ($k_r$) and the apparent dissociation constant of the reactivator-inhibited AChE complex ($K_D$).

As of today, none of the known oximes has proven equally effective against all species of OPNA-inhibited AChE.

Recently, WO2017/021319 discloses bifunctional compounds comprising a specific peripheral site ligand (PSL) moiety of the amino-quinoline functionality, which had improved affinity for poisoned hAChE (thus, a lower $K_D$), which allowed them to be potent reactivators of human AChE inhibited with any type of organophosphorous compounds. However, these bifunctional compounds comprise a hydroxyl group, which may be present in position 3 of the pyridine radical. This hydroxyl group needs to be protected and deprotected during synthesis. Moreover, said hydroxyl group may be involved in an intracyclisation of the molecule.

Thus, there remains a need for chemical compounds efficient in therapeutic applications, particularly against OPNA intoxications, which are quick and easy to synthesise, with a good yield, and at a high scale. These compounds must be stable, without any intracyclisation.

Surprisingly, the inventors have now discovered that specific pyridinaldoxime compounds, bearing a hydrogen or a specific alkoxy radical at the 3-position, fulfill these needs. They may pass through the blood brain barrier easily, notably because they are uncharged.

Indeed, such compounds are quick, simple and very easy to produce. The obtained compounds show no intramolecular cyclisation, and may be used in human therapy.

Notably, these compounds may be used as antidotes against OPNA intoxications or as detoxifying agents against organophosphorus compounds, thanks to their effective and fast reactivation of hAChE. Without being bound by any theory, these molecules seem to selectively bind to the catalytic site of hAChE. They particularly show very high reactivation efficiency of inhibited AChE. The oxime of the compounds may be regenerated, once it has dephosphorylated the serine residue: thus, the compounds may be used many times. The compounds are also agonists of adenosine 2A receptors. Consequently, they may be used in the treatment of inflammation; in the treatment of neurodegenerative diseases such as Alzheimer's or Parkinson's disease; in the treatment of cancer and notably thanks to their inhibitory activity of histone deacetylase (HDAC) in the treatment of diabetes and/or in the treatment of pain.

Thus, a first object of the present invention is a compound of formula (I):

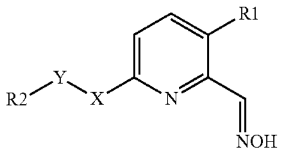

(I)

wherein the different groups are as defined in the detailed description below.

Another object of the present invention is a process for preparing the compounds of formula (I), especially by a Sonogashira reaction, as detailed below.

Another object of the present invention is a pharmaceutical composition comprising at least one compound of formula (I) and at least one pharmaceutically acceptable support.

Another object of the invention is a compound according to the invention, for use as a medicine.

A further object of the invention is a compound according to the invention for use in the treatment of a nervous and/or respiratory failure due to intoxication with at least one organophosphorous nerve agent.

A further object of this invention is a compound according to the invention for use in the treatment of inflammation.

A further object of this invention is a compound according to the invention for use in the treatment of neurological diseases such as Alzheimer's or Parkinson's disease.

A further object of this invention is a compound according to the invention for use in the treatment of cancer.

A further object of this invention is a compound according to the invention for use in the treatment of diabetes.

A further object of this invention is a compound according to the invention for use in the treatment of pain.

The first object of the present invention is a compound of formula (I), or one of its pharmaceutically acceptable salts:

(I)

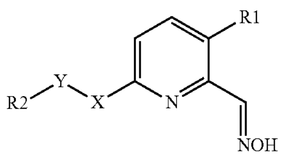

where:

R1 is H, or a linear or cyclic (preferably aromatic) C1-C7 alkoxy radical. Preferably R1 is methoxy or benzyloxy;

—X—Y— is —CH2-(CH2)n-, —C≡C—,

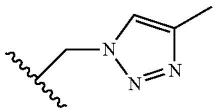 [SMILES: *Cn1cc(C)nn1]

or —X—Y— is Br and R2 does not exist;

n is an integer between 0 and 5;

R2 is a group chosen from alkyl, aryl, aralkyl, heteroaryl, —R3-N(R4)(R5), radical A, radical B, radical C and radical D, wherein radical A or radical B or radical C or radical D may be linked to —Y—X— by an alkyl group, preferably an ethyl group:

A

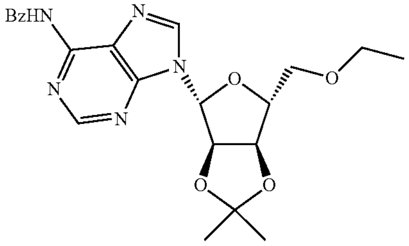

B

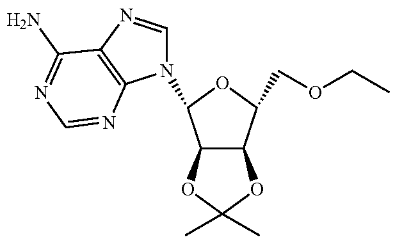

C

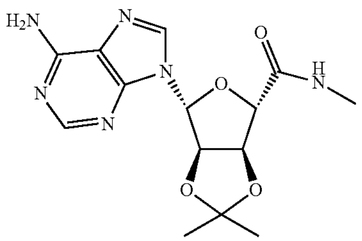

-continued

D

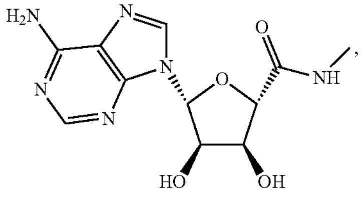

R3 is a C1-C4 alkyl group, and

R4 and R5 are identical or different and each independently represent H, a naphthyl radical, a 5-fluoroquinolin-4-yl radical, a quinolin-4-yl radical or a 8-methoxyquinolin-4-yl radical or R4 and R5 form together with the nitrogen atom a 4-benzyl-piperazin-1-yl radical or a 3,7-dimethyl-2,6-dioxo-2,3,6,7-tetrahydro-1H-purin-1-yl radical.

The attachment point of the triazole group, for the definition of —X—Y—, is indicated by a star of each side of said triazole group:

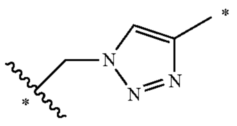 [SMILES: *Cn1cc(C)nn1]

The attachment point of any one of the moieties A to D (in the definition of R2) to the rest of the molecule of formula (I) is indicated by a star:

A

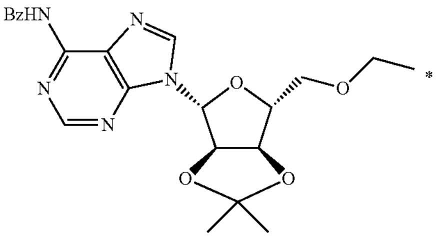

B

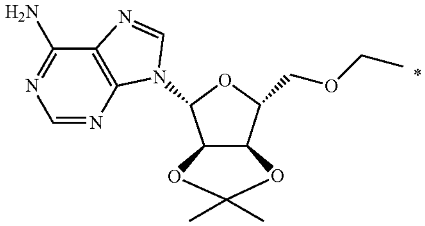

C

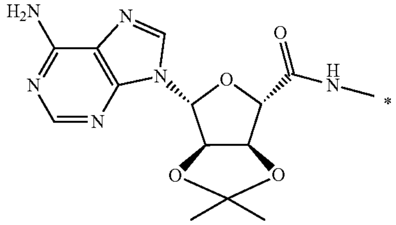

-continued

D

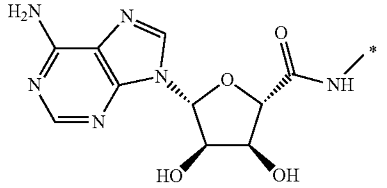

The «Bz» of Radical A means benzoyle, i.e. Ph-C(=O)—.

By "pharmaceutically acceptable salt", it is meant any salt of a compound of formula (I) with an acid or a base. The pharmaceutically acceptable salt may be the hydrochloride salt.

The salt may be obtained with the pyridine of formula (I), to give the pyridinium salt.

For example, when R4 and/or R5 are identical or different and each independently represents a 5-fluoroquinolin-4-yl radical, a quinolin-4-yl radical or a 8-methoxyquinolin-4-yl radical, said radical may be complexed with HCl, in order to give the 5-fluoro-4-quinolinium radical, the 4-quinolinium radical or the 8-methoxy-4-quinolinium radical, respectively. Preferred pharmaceutically acceptable salts are the 5-fluoro-4-quinolinium, the 4-quinolinium and the 8-methoxy-4-quinolinium radicals.

The oxime of compound of formula (I) may be labeled with one or more isotopes such as $^{15}N$, $^{18}O$, $^{2}H$ or $^{3}H$. Indeed, such a stable, non-toxic and non-radioactive isotope would allow in vivo and in vitro biological studies.

By "alkyl", it is meant a linear hydrocarbon group preferably comprising from 1 to 20 carbon atoms, in particular from 1 to 15 carbon atoms, or a branched or cyclic hydrocarbon group comprising from 3 to 20 carbon atoms. Examples of alkyl groups include methyl, ethyl, n-propyl, isopropyl, n-butyl, isobutyl, tert-butyl, n-pentyl, isopentyl, n-hexyl, n-tridecyl, cyclohexyl and cyclohexylmethyl groups, and preferably ethyl, propyl, n-hexyl, n-tridecyl, cyclohexyl or cyclohexylmethyl group.

The C1-C4 alkyl is chosen from methyl, ethyl, n-propyl, isopropyl, n-butyl, isobutyl, tert-butyl.

By "linear C1-C7 alkoxy radical", it is meant a radical Rad-O— in which Rad is a linear C1-C7 alkyl radical. Preferably the linear C1-C7 alkoxy radical is methoxy.

By "cyclic (preferably aromatic) C1-C7 alkoxy radical", it is meant a radical Rad-O— in which Rad is a cyclic, preferably aromatic, C1-C7 alkyl radical. Preferably the cyclic C1-C7 alkoxy radical is an aromatic C1-C7 alkoxy radical, and more preferably benzyloxy.

By "aryl", it is meant a monocyclic or polycyclic aromatic hydrocarbon group, which may be optionally substituted. Preferably, the aryl group is a phenyl, or a polycyclic aromatic hydrocarbon (PAH). A preferred PAH is pyrene. The aryl may be substituted by at least one alkyl group and/or by at least a cyano group (—CN). A preferred example of aryl group is phenyl.

By "aralkyl", it is meant an aryl group as described above, linked to the compound of formula (I) by an alkyl group. Preferably, the aralkyl group is a phenylpropyl. The aralkyl may be substituted on the aryl group by at least one alkyl group and/or by at least a cyano group (—CN). Preferably the aralkyl is phenylpropyl.

By "heteroaryl", it is meant an aryl group in which at least one carbon atom of the aromatic ring is substituted by a heteroatom, and which may be optionally substituted. The heteroatom may be nitrogen, oxygen, phosphorus or sulfur. Preferably the heteroatom is nitrogen. Examples of heteroaryl groups include pyrrole, thiophene, furane, pyridine, pyrimidine, pyrazine, triazine, imidazole, thiazole, oxazole, and isoxazole groups. Preferably, the heteroaryl group is a pyridine group such as 4- or 3-pyridino. The heteroaryl may be substituted by at least one alkyl group and/or by at least a cyano group (—CN). Preferably, the heteroaryl group is in salt form, preferably a pyridinium group such as 4- or 3-pyridininium.

According to a first embodiment, it is preferred in formula (I) that —X—Y— is Br and R2 does not exist.

Thus, the compounds of formula (I) or one of their pharmaceutically acceptable salts, have scaffold 1 below:

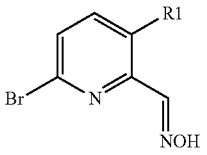

Scaffold 1 wherein R1 is as defined above.

The compounds of scaffold 1 are such that R1 is H, or a linear or cyclic (preferably aromatic) C1-C7 alkoxy radical. Preferably the compounds of scaffold 1 are such that R1 is H, methoxy or benzyloxy.

According to a second embodiment, it is preferred in formula (I) that —X—Y— is —C≡C— (scaffold 2):

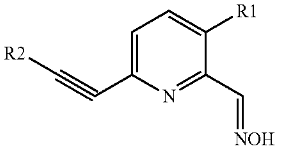

Scaffold 2 where R1 and R2 are as defined above.

The compounds of scaffold 2 are bifunctional compounds.

Preferably, the compounds of scaffold 2 are such that R1 is chosen from H and methoxy. Preferably, the compounds of scaffold 2 are such that R2 is chosen from radical A, radical B, radical C and radical D, preferably wherein radical C or radical D are linked to —Y—X— by an alkyl group, more preferably an ethyl group:

A

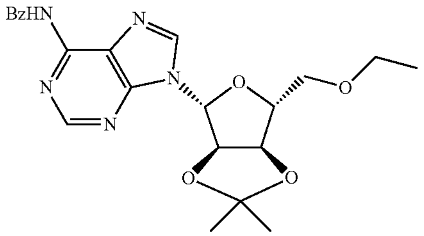

-continued

B

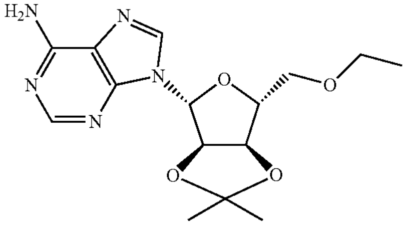

C

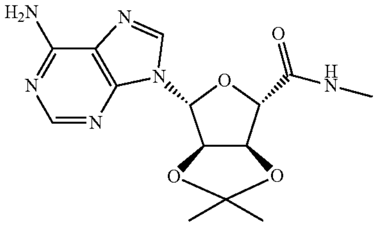

D

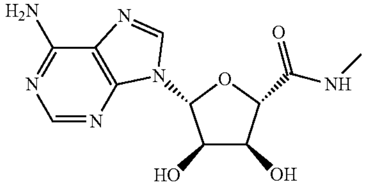

.

Alternatively, preferably, the compounds of scaffold 2 are such that R2 is alkyl, heteroaryl, aralkyl or —R3-N(R4)(R5), wherein R3 is a C1-C4 alkyl group, preferably R3 is chosen from methyl, ethyl and n-propyl, R4 is H, and R5 is chosen from a naphthyl radical, a 5-fluoroquinolin-4-yl radical, a quinolin-4-yl radical or a 8-methoxyquinolin-4-yl radical.

Alternatively, preferably, the compounds of scaffold 2 are such that R2 is —R3-N(R4)(R5), wherein R3 is a C1-C4 alkyl group, preferably R3 is chosen from methyl, ethyl and n-propyl, and R4 and R5 form together with the nitrogen atom a 4-benzyl-piperazin-1-yl radical or a 3,7-dimethyl-2,6-dioxo-2,3,6,7-tetrahydro-1H-purin-1-yl radical.

The compounds of scaffold 2 show a decreased pKa and an increased reactivation efficiency (kr2 in mM-1 min-1), due to increased affinity, as compared to compounds without the triple binding and with an —OH as R1; and as compared to reference molecules such as pralidoxime (2-PAM) and HI-6.

According to a third embodiment, it is preferred in formula (I) that —X—Y— is —CH2-(CH2)n-, where n is an integer between 0 and 5 (scaffold 3):

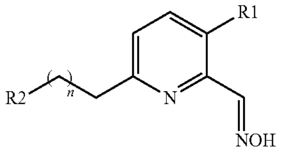

Scaffold 3 where R1 and R2 are as defined above.

The compounds of scaffold 3 are bifunctional compounds.

Preferably, the compounds of scaffold 3 are such that R1 is chosen from H and methoxy. Preferably, the compounds of scaffold 3 are such that R2 is alkyl, aryl, aralkyl or —R3-N(R4)(R5), where R3 is a C1-C4 alkyl group, preferably R3 is chosen from methyl, ethyl and n-propyl, R4 is H, and R5 is chosen from a naphthyl radical, a 5-fluoroquinolin-4-yl radical, a quinolin-4-yl radical or a 8-methoxyquinolin-4-yl radical.

Alternatively, preferably, the compounds of scaffold 3 are such that R2 is —R3-N(R4)(R5), wherein R3 is a C1-C4 alkyl group, preferably R3 is chosen from methyl, ethyl and n-propyl, and R4 and R5 form together with the nitrogen atom a 4-benzyl-piperazin-1-yl radical.

According to a fourth embodiment, it is preferred in formula (I) that —X—Y— is

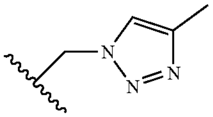

(scaffold 4)

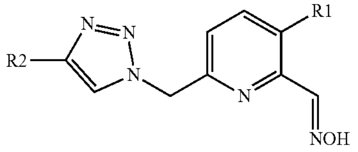

Scaffold 4 where R1 and R2 are as defined above.

The compounds of scaffold 4 are trifunctional compounds.

Preferably, the compounds of scaffold 4 are such that R1 is chosen from H, methoxy and benzyloxy; preferably R1 is H.

Preferably, the compounds of scaffold 4 are such that R2 is chosen from radical A, radical C and radical D, preferably wherein radical C or radical D are linked to —Y—X— by an alkyl group, more preferably an ethyl group:

A

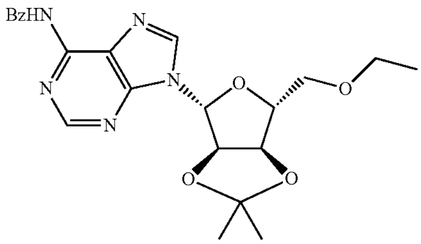

C

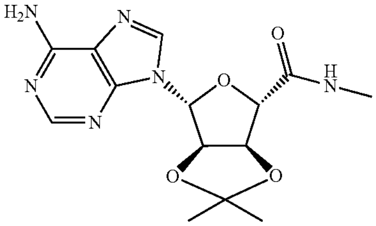

-continued

D

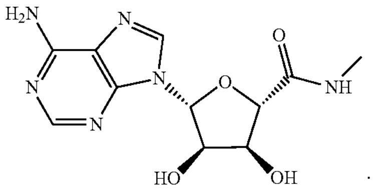

The compounds of scaffold 4 selectively target the catalytic site of hAChE and show very good reactivation kinetic.

Preferably, the compound of formula (I) is chosen among the following compounds and their pharmaceutically acceptable salts:

6-Bromopicolinaldehyde oxime 2:

2

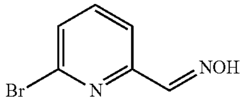

6-(5-phenylpent-1-yn-1-yl)picolinaldehyde oxime 5:

5

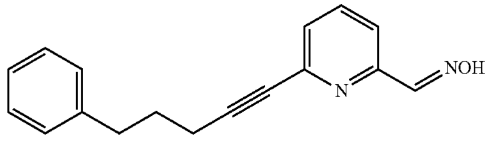

6-(5-phenylpentyl)picolinaldehyde oxime 7:

7

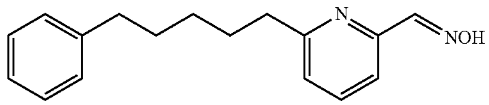

6-(pentadec-1-yn-1-yl)picolinaldehyde oxime 9:

9

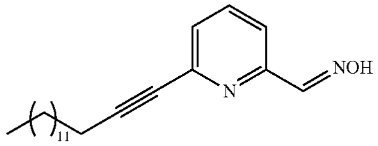

6-pentadecylpicolinaldehyde oxime 10:

10

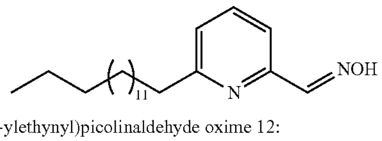

6-(pridin-3-ylethynyl)picolinaldehyde oxime 12:

12

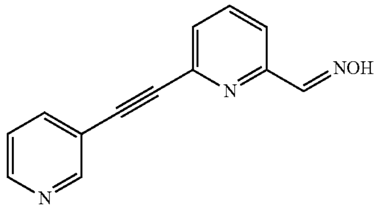

-continued 2-((hydroxyimino)methyl)-6-(pyridin-1-ium-3-ylethynyl)pyridin-1-ium chloride 13:

13

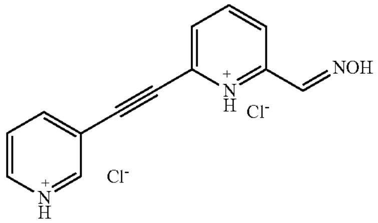

N-(4-{6-[hydroxyimino)methyl]pyridine-2-yl}but -3-yn-1-yl) naphthalene-1-amine 19:

19

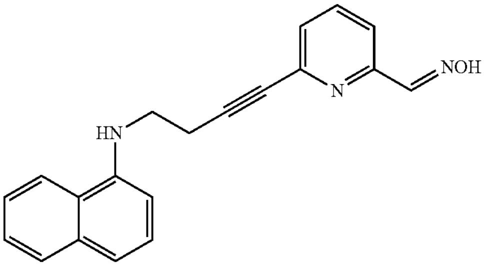

N-(4-{6-[hydroxyimino)methyl]pyridine-2-yl}but -3-yn-1-yl) naphthalene-1-amine 20:

20

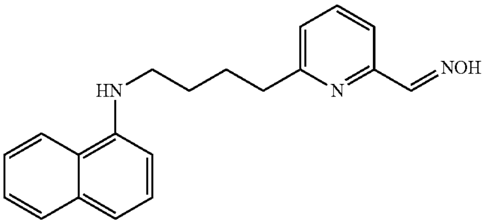

6-(4-(quinolin-4-ylamino)but-1-yn-1-yl)picolinaldehyde oxime 25:

25

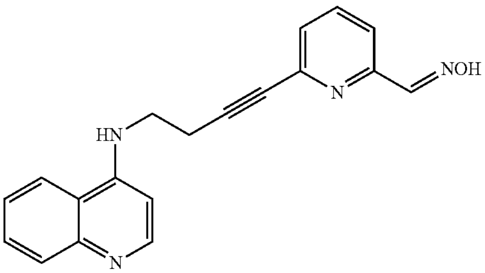

Methyl 3-hydroxy-6-(4-(quinoline-4-ylamino)butyl)picolinate 26:

26

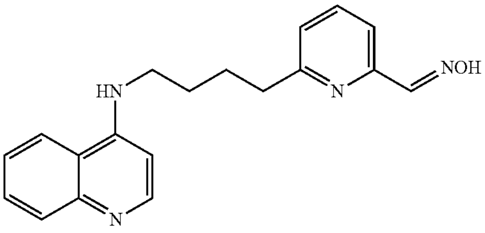

-continued 6-(4-((5-fluoroquinolin-4-yl)amino)but-1-yn-1-yl)picolinaldehyde oxime 30:

30

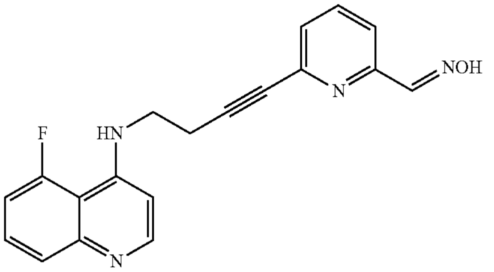

6-(4-((5-fluoroquinolin-4-yl)amino)butyl)picolinaldehyde oxime 31:

31

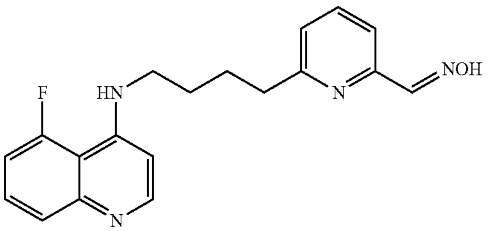

6-(4-((8-methoxyquinolin-4-yl)amino)but-1-yn-1-yl)picolinaldehyde oxime 36:

36

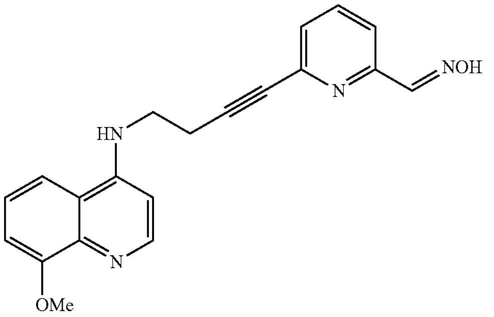

6-(4-((8-methoxyquinolin-4-yl)amino)butl)picolinaldehyde oxime 37:

37

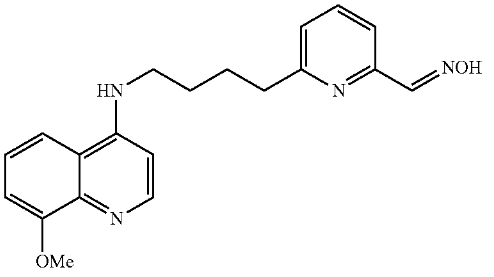

6-(3-(4-benzylpiperazin-1-yl)prop-1-yn-1-yl)picolinaldehyde oxime 42:

42

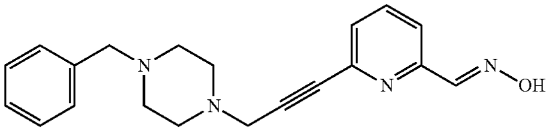

-continued 6-(3-(4-benzylpiperazin-1-yl)propyl)picolinaldehyde oxime 43:

43

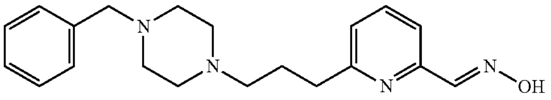

6-(4-(4-benzylpiperazin-1-yl)but-1-yn-1-yl)picolinaldehyde oxime 47:

47

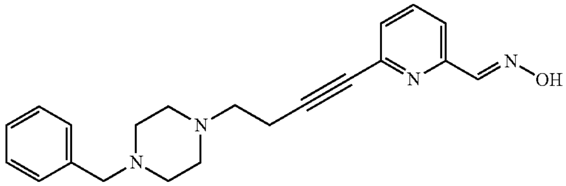

6-(4-(4-benzylpiperazin-1-yl)butl)picolinaldehyde oxime 48:

48

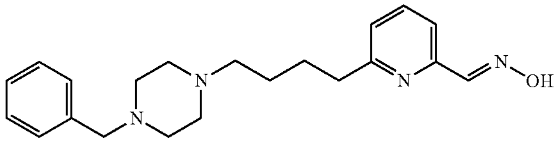

6-(4-(3,7-dimethyl-2,6-dioxo-2,3,6,7-tetrahydro-1H-purin-1-yl)but-1-yn-1-yl)picolinaldehyde oxime 51:

51

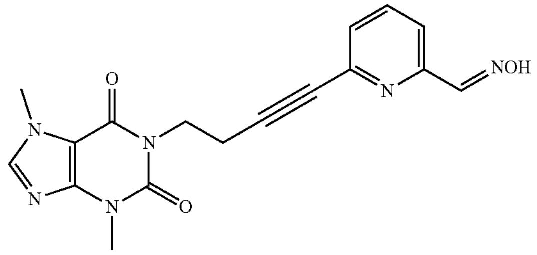

(3aS,4S,6R,6aR)-6-(6-amino-9H-purin-9-yl)-N-(4-6-(hydroxyimino)methyl)pyridin-2-yl)but-3-yn-1-yl)-2,2-dimethyltetrahydrofuro[3,4-d][1,3]dioxole-4-carboxamide 56:

56

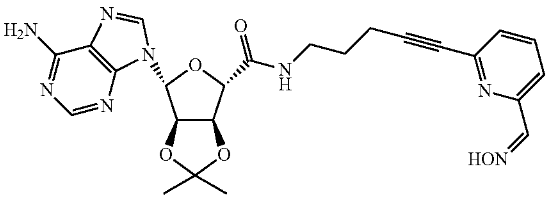

(2S,3S,4R,5R)-5-(6-amino-9H-purin-9-yl)-3,4-dihydroxy-N-(4-(6-hydroxyimino)methyl)pyridin-2-yl)but-3-yn-1-yl)tetrahydrofuran-2-carboxamide 57:

57

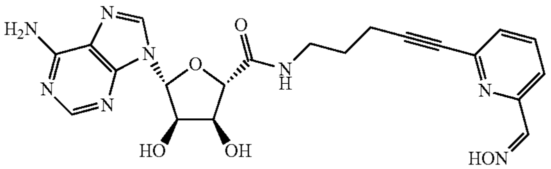

-continued

N-(9-(3aR,4R,6R,6aR)-6-(((3-(6-(hydroxyimino)methyl)pyridin-2-yl)prop-2-yn-1-yl)oxy)methyl)-2,2-dimethyltetrahydrofuro[3,4-d][1,3] dioxol-4-yl)-9H-purin-6-yl)benzamide 60:

60

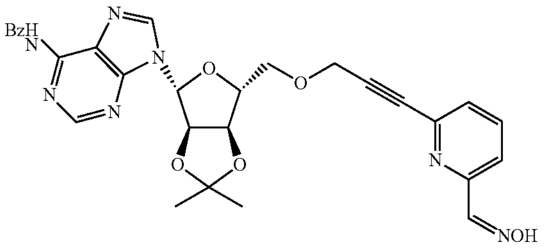

6-(3-(((3aR,4R,6R,6aR)-6-(6-amino-9H-purin-9-yl)-2,2-dimethyltetrahyrofuro[3,4-d][1,3]dioxol-4-yl)methoxy)prop-1-yn-1-yl) picolinaldehyde oxime 61:

61

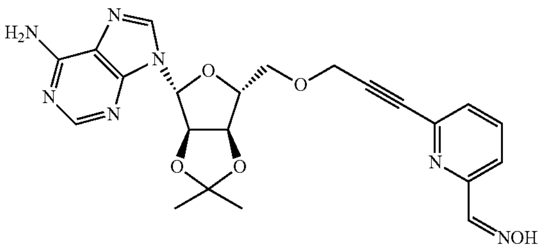

3-methoxy-6-(5-phenylpent-1-yn-1-yl)picolinaldehyde oxime 64:

64

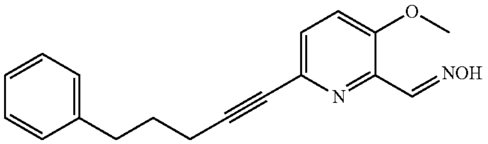

3-methoxy-6-(5-phenylpentyl)picolinaldehyde oxime 65:

65

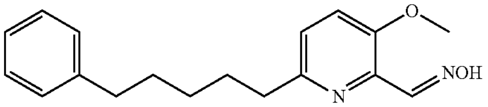

3-methoxy-6-(4-(quinolin-4-ylamino)but-1-yn-1-1yl)picolinaldehyde oxime 67:

67

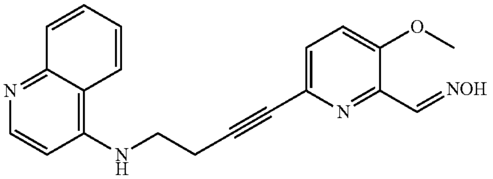

4-((4-(6-((hydroxyimino)methyl)-5-methoxypyridin-2-yl)but-3-yn-1-yl) amino)quinolin-1-ium chloride 68:

68

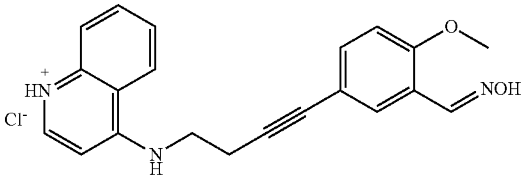

-continued 3-methoxy-6-(4-(quinolin-4-ylamino)butyl)picolinaldehyde oxime 69:

69

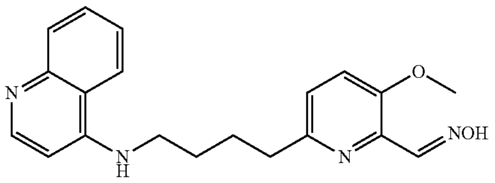

4-((4-(6-((hydroxyimino)methyl)-5-methoxypyridin-2-yl)butyl)amino) quinolin-1-ium 70:

70

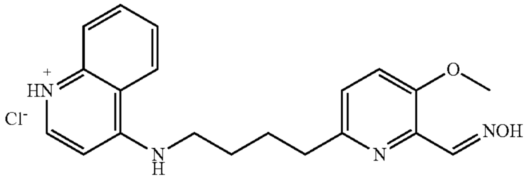

(3aS,4S,6R,6aR)-6-(6-amino-9H-purin-9-yl)-N-(4-(6-(-(hydroxyimino) methyl-5-methoxypyridin-2-yl)but-3-yn-1-yl)-2,2-dimethyltetrahydrofuro [3.4-d][1,3]dioxole-4-carboxamide 72:

72

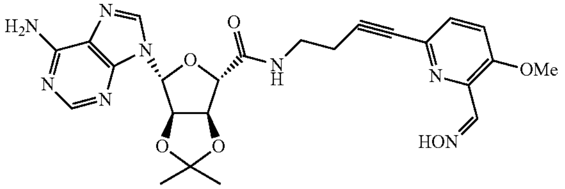

(3aS,4S,6R,6aR)-6-(6-amino-9H-purin-9-yl)-N-(2-(1-((6-(-(hydroxyimino) meth-yl)-pyridin-2-yl)methyl)-1H-1,2,3-trazol-4-yl)ethyl)-2,2-dimethyltetrahydrofuro[3.4-d][1,3]dioxole-4-carboxamide 77:

77

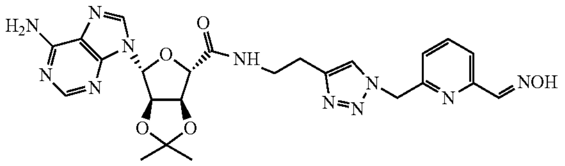

(2S,3S,4R,5R)-5-(6-amino-9H-purin-9-yl)-3,4-dihydroxy-N-(2-(1-((6-(hydroxyimino)methyl)pyridin-2-yl)methyl)-1H-1,2,3-trazol-4-yl) ethyl)tetrahydrofuran-2-carbox-amide. hydrochloride 78:

78

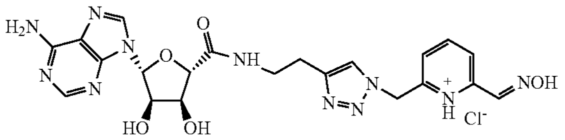

N-(9-((3aR,4R,6R,6aR)-6-(((1-((6-(-(hydroxyimino)methyl)pyridin-2-yl) methyl)-1H-1,2,3-triazol-4-yl)methoxy)methyl)-2,2-dimethyltetrahydrofuro [3,4-d][1,3]dioxol-4-yl)-9H-purin-6-yl)benzamide 79:

79

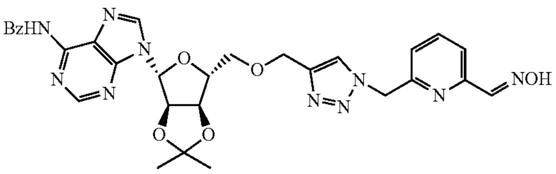

More preferably, the compound of formula (I) is chosen among the following compounds:

(2S,3S,4R,5R)-5-(6-amino-9H-purin-9-yl)-3,4-dihydroxy-N-(4-(6-(hydroxyimino)methyl)pyridin-2-yl)but-3-yn-1-yl) tetrahydrofuran-2-carboxamide 57:

57

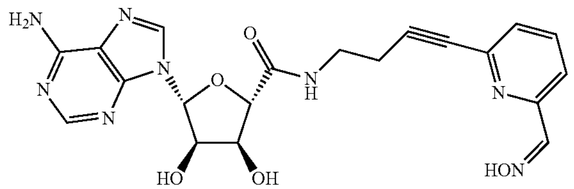

6-(4-(quinolin-4-ylamino)but-1-yn-1-yl)picolinaldehyde oxime 25:

25

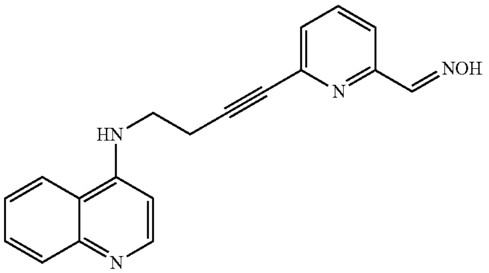

Methyl 3-hydroxy-6-(4-(quinoline-4-ylamino(butyl)picolinate 26:

26

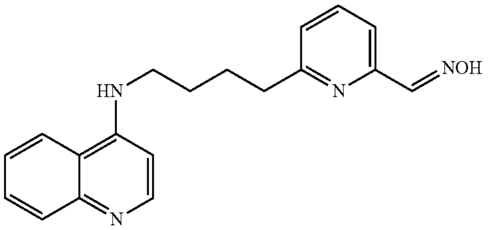

(2S,3S,4R,5R)-5-(6-amino-9H-purin-9-yl)-3,4-dihydroxy-N-(2-(1-((6-(-(hydroxyimino) methyl)pyridin-2-yl)methyl)-1H-1,2,3-triazol-4-yl)ethyl)tetrahydrofuran-2-carbox-amide. hydrochloride 78:

78

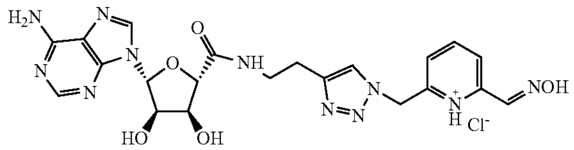

Preparation of the Compounds of Formula (I)

A compound of formula (I) or one of its pharmaceutically acceptable salts according to the invention may be synthesised by any appropriate method. For example, the compounds of formula (I) or one of its pharmaceutically acceptable salts may be prepared according to the following scheme:

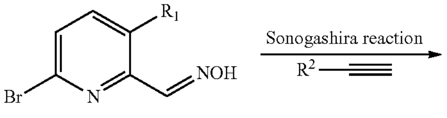

Scaffold 1

-continued

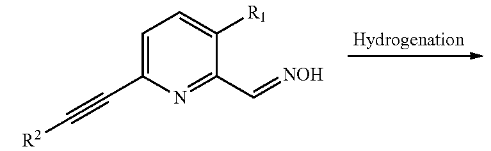

Scaffold 2

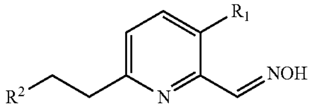

Scaffold 3

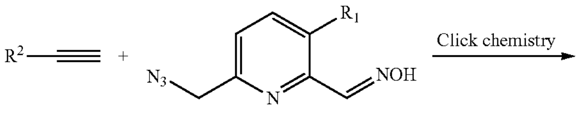

Clickable reactivator

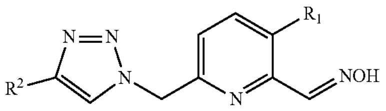

Scaffold 4

The compound of formula (I) of scaffold 1, i.e. wherein X—Y is Br, is reacted with R2-X—Y—H (where X—Y is —C≡C—), in order to obtain the compound of formula (I) of scaffold 2 wherein X—Y is —C≡C—.

Then, by selective hydrogenation (by $H_2$), one can easily obtain either the compound of formula (I) where X—Y is —CH2-CH2- (scaffold 3).

In order to obtain the compounds of scaffold 4, the alkyne R2-C≡CH is reacted by Click chemistry with the corresponding clickable reactivator.

Such methods are exemplified in the following examples.

Preparation of the Compounds of Formula (I)

A compound of formula (I) or one of its pharmaceutically acceptable salts according to the invention may be synthesised by any appropriate method known by anyone of ordinary skill in the art.

Preferably, the compounds of formula (I) are synthetised as described below. Such a process is chemoselective. Particularly, it does not necessitate any previous protection step of the oxime. Said process comprises a minimal number of steps (one or two) and is quickly performed at ambient temperature.

Scaffold 1

Particularly, the compounds of scaffold 1:

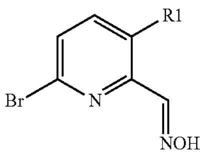

Scaffold 1 may be obtained by reaction of either the picolinaldehyde precursor or the picolinonitrile derivative with hydroxylamine hydrochloride, preferably in an organic solvent. In all cases hydroxylamine hydrochloride may be labelled with $^{15}N$ element.

Such synthesis is illustrated for 6-bromopicolinaldehyde oxime 2 in the examples.

Scaffold 2

In particular, the process for the synthesis of compounds of formula (I), scaffold (2), may comprise, preferably consists in, a late step of Sonogashira coupling reaction between a compound of scaffold 1, i.e. a 6-bromopyridinaldoxime, and a compound bearing a terminal alkyne (see scheme above).

Such a Sonogashira coupling reaction may be performed in the presence of a solvent such as tetrahydrofuran (THF), triethylamine ($Et_3N$) or preferably a mixture thereof; in the presence of a catalyst such as $Pd(PPh_3)_4$ and CuI.

Such a Sonogashira coupling is performed without any protection of the oxime moiety.

Scaffold 3

The resulting alkyne (scaffold 2) may then be reduced by reaction with hydrogen, for instance in presence of a Pd catalyst (such as Pd/C), to obtain the corresponding alkyl (scaffold 3), in a selective hydrogenation step.

Again, the hydrogenation step is performed without any protection of the oxime moiety.

Scaffold 4

As described above and illustrated in the above scheme, in order to obtain the compounds of scaffold 4, the alkyne R2-C≡CH is reacted by Click chemistry with the corresponding clickable reactivator.

Thus, an object of the invention is a process for preparing a compound of formula (I), wherein —X—Y— is —CH2-CH2- or —C≡C—, and R1 and R2 are as defined above, comprising a Sonogashira coupling reaction between a 6-bromopyridinaldoxime and a compound bearing a terminal alkyne, optionally followed by a reduction step by reaction with hydrogen.

Pharmaceutical Uses of the Compounds of the Invention

The compounds of this invention may be used in the treatment of nervous and/or respiratory failure due to intoxication with at least one organophosphorous nerve agent which may preferably be selected from warfare agents such as VX, Tabun, Sarin, Cyclosarin and Soman and pesticides such as Paraoxon, Parathion and TEPP. The compounds of the invention may be used in the treatment of nervous and/or respiratory failure due to intoxication with at least one organophosphorous nerve agent, by virtue of their reactivation potency of organophosphorous inhibited cholinesterases.

These compounds may alternatively be used in the treatment of diseases that involve a reduced production of acetylcholine, which may be overcome by the administration of acetylcholinesterase inhibitors. Examples of such diseases include in particular neurological diseases such as Alzheimer's or Parkinson's disease.

The compounds of this invention are also agonists of adenosine 2A receptors. Consequently, they may be used in the treatment of inflammation; in the treatment of cancer; in the treatment of diabetes; and/or in the treatment of pain.

The compound of this invention is usually included in a pharmaceutical composition comprising at least one compound according to the invention and a pharmaceutically acceptable support.

The amount of compound of formula (I) or one of its pharmaceutically acceptable salts in the composition according to the invention may vary in a broad range depending upon the patient, the mode of administration and the expected effect.

The compound or composition according to the invention can be administered orally or non-orally, for instance via topical, parenteral, intramuscular, intravenous, cutaneous, nasal or rectal route.

The pharmaceutical composition of the invention can present different forms including granules, powders, tablets, capsules, syrups, emulsions, suspensions, and forms used for non-oral administration, such as injections, sprays, transdermal patches or suppositories. These pharmaceutical forms can be prepared via known conventional techniques.

The preparation of an orally administered solid pharmaceutical form can be for instance performed by the following process: an excipient (for example lactose, sucrose, starch or mannitol), a desintegrant (for example calcium carbonate, calcium carboxymethylcellulose, alginic acid, sodium carboxymethylcellulose, colloidal silicon dioxide, sodium croscarmellose, crospovidone, guar gum, magnesium aluminium silicate, microcrystalline cellulose, cellulose powder, pregelatinised starch, sodium alginate or starch glycolate), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are added to the active compound and the mixture obtained is then tableted. If necessary, the tablet can be coated via the known techniques, in order to mask the taste (for example with cocoa powder, mint, borneol or cinnamon powder) or to allow enteric dissolution or sustained release of the active compounds. Coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide or quinoline yellow lake).

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, it is possible to add ethanol, propylene glycol or any other pharmaceutically acceptable non-aqueous solvent. The aqueous suspensions for oral use can be obtained by dispersing the finely divided active principle in water with a viscous product, such as a natural or synthetic gum or resin, methylcellulose or sodium carboxymethylcellulose.

The pharmaceutical forms for injection can be obtained, for example, by the following process. The active compound is dissolved, suspended or emulsified either in an aqueous medium (for example distilled water, physiological saline or Ringer's solution) or in an oily medium (for example olive oil, sesame seed oil, cottonseed oil, corn oil or propylene glycol), with a dispersant (for example Tween® 80, HCO® 60 (Nikko Chemicals), polyethylene glycol, carboxymethylcellulose or sodium alginate), a preserving agent (for example methyl p-hydroxybenzoate, propyl p-hydroxybenzoate, benzyl alcohol, chlorobutanol or phenol), an isotonicity agent (for example sodium chloride, glycerol, sorbitol or glucose) and optionally other additives, such as a solubilizing agent (for example sodium salicylate or sodium acetate) or a stabilizer (for example human serum albumin).

Pharmaceutical forms for external use (topical use) can be obtained from a solid, semi-solid or liquid composition containing the active compound. For example, to obtain a solid form, the active compound can be treated with excipients (for example lactose, mannitol, starch, microcrystalline cellulose or sucrose) and a thickener (for example natural gums, cellulose derivatives or acrylic polymers) so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator (for example carbonic acid, phosphoric acid, citric acid, hydrochloric acid or sodium hydroxide) and a preserving agent (for example a p-hydroxybenzoic acid ester, chlorobutanol or benzalkonium chloride).

A method for the treatment of a nervous and/or respiratory failure due to intoxication with at least one organophosphorous nerve agent, comprising the administration of at least one compound according to the invention is also described herein.

A method for the treatment of a neurological disease such as Alzheimer's or Parkinson's disease, comprising administering at least one compound according to the invention is also described herein.

A method for the treatment of inflammation, comprising administering at least one compound according to the invention is also described herein.

A method for the treatment of a cancer, comprising administering at least one compound according to the invention is also described herein.

A method for the treatment of diabetes, comprising administering at least one compound according to the invention is also described herein.

A method for the treatment of pain, comprising administering at least one compound according to the invention is also described herein.

Within the context of the invention, the term treatment denotes curative, symptomatic, and/or preventive treatments. In particular, it can refer to reducing the progression of the disease, reducing or suppressing at least one of its symptoms or complications, or improving in any way the state of health of patients.

The administration of the compounds or of the composition according to the invention may be performed before, during or after the exposition of the subject to the organophosphorous nerve agent.

In the present invention, the terms "subject" and "patient" are used interchangeably and designate a human subject.

The amount of compound of formula (I) or one of its pharmaceutically acceptable salts to be administered according to the invention may vary in a broad range depending upon the patient, the mode of administration and the expected effect. In particular, the amount of compound of formula (I) or one of its pharmaceutically acceptable salts may be comprised between 200 mg and 4000 mg, with up to 3 daily doses.

The compound or composition according to the invention may be co-administered with at least one other active agent, such as an antimuscarinic agent, in particular Atropine, an anticonvulsant, in particular Diazepam or one of its prodrugs, such as Avizafone, and/or a bioscavenger able to capture and/or degrade OPNAs in blood, such as human butyrylcholinesterase.

The term "co-administered" means that the administration of the compound or composition according to the invention and that of the other active agent can be simultaneous, sequential and/or separate.

Other Uses of the Compounds of the Invention

The compounds of this invention may further be used as tools for in vivo and/or in vitro biological studies. In this application, the compounds of formula (I) or one of their pharmaceutically acceptable salts may include one or more isotopes, which will allow for their detection.

The following examples are provided as illustrative, and not limitative, of the present invention.

EXAMPLES

Example 1: Synthesis of Compounds of the Invention

µI—Synthesis of Bifunctional Pyridinaldoxime Analogs

Synthesis of 6-(5-phenylpentyl)picolinaldehyde oxime

Scheme 1: Synthesis of 6-bromopicolinaldehyde oxime

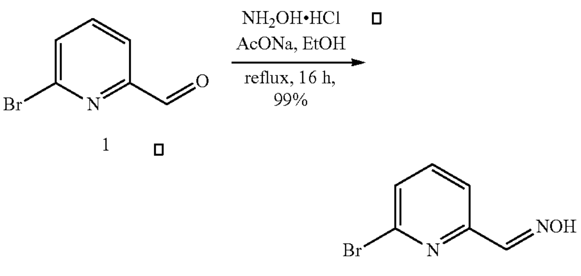

1

2

Scheme 2: Synthesis of 6-substituted picolinaldehyde oxime

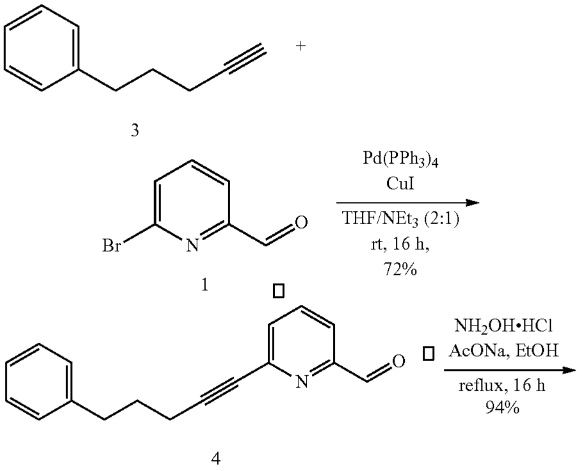

3

1

4

-continued

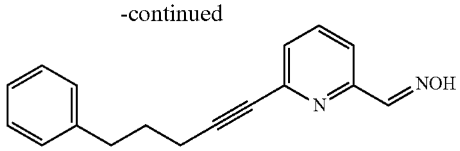

5

Scheme 3: Alternative route to 6-substituted picolinaldehyde oxime

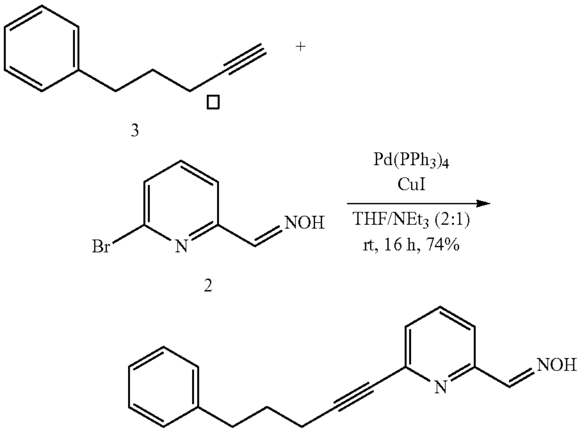

3

2

5

Scheme 4: Selective Hydrogination

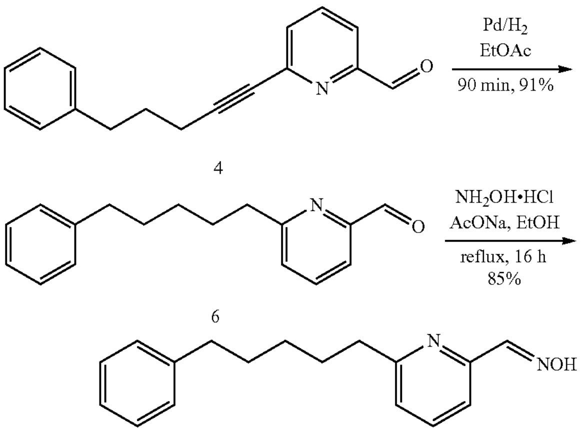

4

6

7

6-Bromopicolinaldehyde oxime 2

2

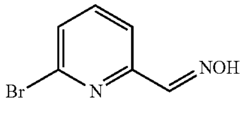

This compound was synthesized by following the work published by L. Zhang et al.[1]; To a solution of 6-bromopicolinaldehyde 1 (3.00 g, 16.1 mmol) in anhydrous EtOH (50 mL) at room temperature (rt) was added hydroxylamine hydrochloride (2.24 g, 32.3 mmol) and sodium acetate (2.65 g, 32.3 mmol). Upon addition, the colourless solution with a white suspension was stirred at 90° C. for 3 h. The solution was cooled to rt and concentrated in vacuo. The resulting white solid was dissolved in EtOAc (50 mL). The organic layer was washed with $H_2O$ (5×20 mL), dried ($MgSO_4$), filtered and concentrated in vacuo to afford the title compound 2 (3.21 g, 16.0 mmol, 99%) as a white solid. Physical and spectroscopic data are consistent with reported values.[1] mp=168-170° C. (lit.[2] 164-166° C.); IR (neat) $v_{max}$ 3203, 3084, 2912, 1546, 1158, 1119, 704 $cm^{-1}$; $^1$HNMR (400 MHz, $CDCl_3$) δ 11.90 (s, 1H, CHNOH), 8.04 (s, 1H, CHNOH), 7.82-7.74 (m, 2H, NCCHCHCH, NCCHCHCH), 7.63 (dd, J=6.8, 1.7 Hz, 1H, NCCHCHCH); $^{13}$C NMR (100 MHz, $CDCl_3$) δ 153.3, 147.5, 141.0, 140.1, 128.1, 119.3; HRMS $(ESI)^+$ m/z calcd for $C_6H_5BrN_2O^+$200.9658, found 200.9657.

REFERENCE

1. *Bioorg. Med. Chem. Lett.* 2016, 26, 778-781.

6-(5-phenylpent-1-yn-1-yl)picolinaldehyde 4

4

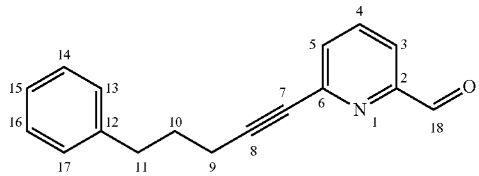

To a degassed solution of bromopiconaldehyde 1 (568 mg, 3.056 mmol, 1.1 equiv) in THF/$Et_3N$ (10 mL/30 mL), $Pd[PPh_3]_4$ (482 mg, 0.0.417 mmol, 0.15 equiv) and CuI (159 mg, 0.834 mmol, 0.3 equiv) were added. After degassing the reaction mixture for 5 min at room temperature, the alkyne 3 (400 mg, 2.78 mmol, 1 equiv) was added dropwise and the reaction mixture was stirred at the room temperature for 16 h. After completion (monitored by TLC), the reaction mixture was concentrated under reduced pressure and the residue was purified by column chromatography (EtOAc/PE 6:94 to EtOAc/PE 1:9) to afford the desired coupled piconaldehyde 4 as a colourless oil (500 mg, 72%). $R_f$ (20% EtOAc+PE) 0.65; IR (neat) $v_{max}$ 3026, 2928, 2856, 2229, 1710, 1580, 1451, 1211, 987, 805, 698, 647, 542 $cm^{-1}$; $^1$H NMR (400 MHz, $CDCl_3$) δ (ppm) 9.99 (s, 1H, $H_{18}$), 7.82-7.71 (m, 2H, $H_3$, $H_4$), 7.53 (dd, J=7.5 Hz, 1H, $H_5$), 7.26-7.10 (m, 5H, $H_{13}$-$H_{17}$), 2.74 (t, J=7.5 Hz, 2H, $H_{11}$), 2.43 (t, J=7.1 Hz, 2H, $H_9$), 1.92 (quintet, J=7.1, 7.5 Hz, 2H, $H_{10}$); $^{13}$C NMR (100 MHz, $CDCl_3$) δ (ppm) 193.09 (C18), 152.76 (C2), 144.43 (C6), 141.21 (C12), 137.21 (C4), 130.92 (C5), 128.47 (C14, C16), 128.41 (C13, C17), 126.02 (C15), 119.94 (C3), 92.32 (C7), 79.93 (C8), 34.90 (C11), 29.74 (C10), 18.81 (C9); HRMS ($ESI^+$) m/z calcd for $C_{17}H_{16}NO^+$250.1226 found 250.1239.

6-(5-phenylpent-1-yn-1-yl)picolinaldehyde oxime 5

5

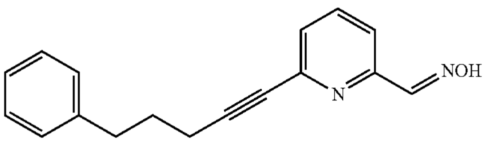

Method 1:

A solution of aldehyde 4 (100 mg, 0.402 mmol, 1 equiv), hydroxylamine hydrochloride (56 mg, 0.803 mmol, 2 equiv), and $CH_3CO_2Na$ (100 mg, 1.206 mmol, 3 equiv) in dry ethanol (6 mL) was stirred at reflux during 16 h. Upon completion (monitored by TLC), the solids were removed by filtration through a short celite pad, the solvent was evaporated, and the residue was purified by column chromatography (EtOAc/PE 1:9) to afford the oxime 5 as a white solid (100 mg, 94%). $R_f$ (20% EtOAc+PE) 0.35; IR (neat) $v_{max}$ 3177, 3005, 2933, 2876, 2226, 1568, 1495, 1445, 1257, 1159, 985, 807, 734, 703, 657, 576, 490 $cm^{-1}$; $^1H$ NMR (400 MHz, $CDCl_3$) δ (ppm) 8.85 (s, 1H, OH), 8.24 (s, 1H, $H_{18}$), 7.68 (dd, J=0.7, 7.8 Hz, 1H, $H_3$), 7.56 (t, J=7.8 Hz, 1H, $H_4$), 7.29 (dd, J=0.7, 7.7 Hz, 1H, $H_5$), 7.29-7.08 (m, 5H, $H_{13}$-$H_{17}$), 2.71 (t, J=7.5 Hz, 2H, $H_{11}$), 2.39 (t, J=7.1 Hz, 2H, $H_9$), 1.89 (quintet, J=7.1, 7.5 Hz, 2H, $H_{10}$); $^{13}C$ NMR (100 MHz, $CDCl_3$) δ (ppm) 151.95 (C2), 150.51 (C18), 144.46 (C6), 141.33 (C12), 136.73 (C4), 128.50 (C14, C16), 128.35 (C13, C17), 127.13 (C5), 125.92 (C15), 119.23 (C3), 91.47 (C7), 80.19 (C8), 34.84 (C11), 29.78 (C10), 18.77 (C9); HRMS ($ESI^+$) m/z calcd for $C_{17}H_{17}N_2O_1^+$ 265.1335 found 265.1360.

Method 2:

To a degassed solution of oxime 2 (77 mg, 0.381 mmol, 1.1 equiv) in THF/$Et_3N$ (5 mL/2 mL), $Pd[PPh_3]_4$ (60 mg, 0.052 mmol, 0.15 equiv) and CuI (20 mg, 0.104 mmol, 0.3 equiv) were added. After degassing the reaction mixture for 5 min at room temperature, the alkyne 3 (50 mg, 0.347 mmol, 1 equiv) was added dropwise and the reaction mixture was stirred at room temperature for 16 h. After completion (monitored by TLC), the reaction mixture was concentrated under reduced pressure and the residue was purified by column chromatography (EtOAc/PE 1:9) to afford the desired coupled oxime 5 as a white solid (68 mg, 74%).

6-(5-phenylpentyl)picolinaldehyde 6

6

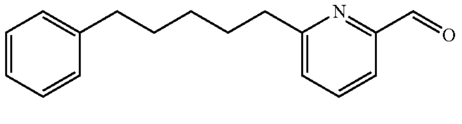

To a degassed solution of 6-substituted piconaldehyde 4 (200 mg, 0.802 mmol, 1 equiv) in dry EtOAc (4 mL), 10% Pd/C (21 mg, 0.201 mmol, 0.25 equiv) was added. After flushing with $H_2$ three times, the reaction mixture was stirred at room temperature under $H_2$ (1 atm.) for 90 min. Upon completion (monitored by TLC), the catalyst was removed by filtration through a short column of celite, the solvent was evaporated, and the residue was purified by column chromatography (EtOAc/PE 1:9) to afford oxime 6 as a colourless liquid (185 mg, 91%); $R_f$ (20% EtOAc+PE) 0.70; IR (neat) $v_{max}$ 3026, 2929, 2856, 1709, 1591, 1455, 1213, 1089, 745, 689, 646, 570, 496 $cm^{-1}$; $^1H$ NMR (400 MHz, $CDCl_3$) δ (ppm) 9.97 (s, 1H, $H_{18}$), 7.73-7.63 (m, 2H, $H_3$, $H_4$), 7.26 (dd, J=1.5, 7.7 Hz, 1H, $H_5$), 7.24-7.05 (m, 5H, $H_{13}$-$H_{17}$), 2.80 (t, J=7.7 Hz, 2H, $H_7$), 2.54 (t, J=7.7 Hz, 2H, $H_{11}$), 1.73 (quintet, J=7.7 Hz, 2H, $H_8$), 1.60 (quintet, J=7.7 Hz, 2H, $H_{10}$), 1.35 (quintet, J=7.3, 7.8 Hz, 2H, $H_9$); $^{13}C$ NMR (100 MHz, $CDCl_3$) δ (ppm) 193.87 (C18), 163.12 (C6), 152.35 (C2), 142.50 (C12), 137.08 (C4), 128.33 (C14, C16), 128.20 (C13, C17), 127.04 (C5), 125.60 (C15), 119.08 (C3), 37.99 (C7), 35.74 (C11), 31.20 (C10), 29.59 (C8), 28.84 (C9); HRMS ($ESI^+$) m/z calcd for $C_{17}H_{20}NO^+$ 254.1537 found 254.1539.

6-(5-phenylpentyl)picolinaldehyde oxime 7

7

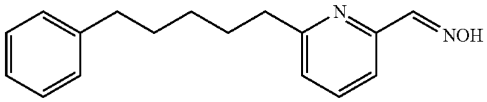

A solution of aldehyde 6 (150 mg, 0.592 mmol, 1 equiv), hydroxylamine hydrochloride (82 mg, 1.184 mmol, 2 equiv), and $CH_3CO_2Na$ (146 mg, 1.776 mmol, 3 equiv) in dry ethanol (12 mL) was stirred at reflux during 16 h. Upon completion (monitored by TLC), the solids were removed by filtration through a short celite pad, the solvent was evaporated, and the residue was purified by column chromatography (EtOAc/PE 1:9) to afford the desired oxime 7 as a white solid (135 mg, 85%). $R_f$ (20% EtOAc+PE) 0.40; IR (neat) $v_{max}$ 3080, 2926, 2856, 1720, 1575, 1452, 1269, 986, 780, 699, 658, 569, 458 $cm^{-1}$; $^1H$ NMR (400 MHz, $CDCl_3$) δ (ppm) 10.20 (br s, 1H, —OH), 8.30 (s, 1H, $H_{18}$), 7.59 (br d, J=8.0 Hz, 1H, $H_3$), 7.50 (t, J=7.8 Hz, 1H, $H_4$), 7.27-6.93 (m, 6H, $H_5$, $H_{13}$-$H_{17}$), 2.74 (t, J=7.8 Hz, 2H, $H_7$), 2.50 (t, J=7.5 Hz, 2H, $H_{11}$), 1.68 (quintet, J=7.5, 7.8 Hz, 2H, $H_8$), 1.57 (quintet, J=7.5 Hz, 2H, $H_{10}$), 1.32 (quintet, J=7.1, 7.8 Hz, 2H, $H_9$); $^{13}C$ NMR (100 MHz, $CDCl_3$) δ (ppm) 162.23, *160.10 (C6), 151.36, *150.73 (C2), 150.40 (C18), 142.61, *142.23 (C12), *138.33, 136.97 (C4), *129.46, 128.33 (C14, C16), 128.16 (C13, C17), 125.61, *125.53 (C5), *124.23, 123.01 (C15), *120.84, 118.112 (C3), 37.86, *37.29 (C7), 35.75 (C11), 31.22, *31.10 (C10), 29.82 (C8), 28.91, *28.69 (C9) (*cis and trans mixture); HRMS ($ESI^+$) m/z calcd for $C_{17}H_{21}N_2O^+$ 269.1648 found 269.1670.

Synthesis of 6-pentadecylpicolinaldehyde oxime 10

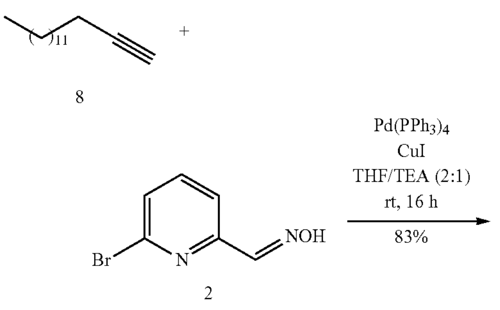

-continued

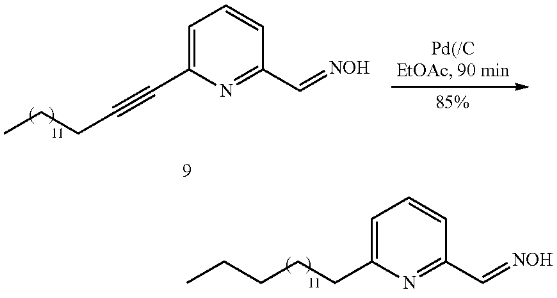

9

10

6-(pentadec-1-yn-1-yl)picolinaldehyde oxime 9

9

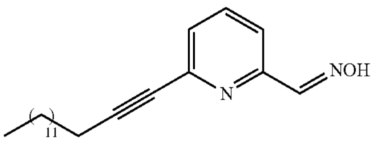

To a degassed solution of oxime 2 (51 mg, 0.252 mmol, 1.05 equiv) in THF/$Et_3N$ (4 mL/2 mL), $Pd[PPh_3]_4$ (42 mg, 0.036 mmol, 0.15 equiv) and CuI (14 mg, 0.072 mmol, 0.3 equiv) were added. After degassing the reaction mixture for 5 min at room temperature, the alkyne 8 (50 mg, 0.240 mmol, 1 equiv) was added dropwise and the reaction mixture was stirred at room temperature for 16 h. After completion (monitored by TLC), the reaction mixture was concentrated under reduced pressure and the residue was purified by column chromatography (EtOAc/PE 6:94) to afford the desired coupled oxime 9 as a white solid (65 mg, 83%). $R_f$ (20% EtOAc+PE) 0.55; IR (neat) $v_{max}$ 3179, 3092, 2914, 2850, 2226, 1722, 1567, 1450, 1268, 1160, 992, 809, 733, 709, 657, 640, 549, 496 $cm^{-1}$; $^1H$ NMR (400 MHz, $CDCl_3$) δ (ppm) 8.50 (s, 1H, OH), 8.26 (s, 1H, $H_{22}$), 7.72 (br d, J=7.8 Hz, 1H, $H_3$), 7.61 (t, J=7.8 Hz, 1H, $H_4$), 7.23 (br d, J=7.7 Hz, 1H, $H_5$), 2.41 (t, J=7.2 Hz, 2H, $H_9$), 1.61 (quintet, J=7.2 Hz, 2H, $H_{10}$), 1.41 (m, 2H, $H_{11}$), 1.24 (s, 18H, $H_{12}$-$H_{20}$), 0.85 (t, J=6.5 Hz, 3H, $H_{21}$); $^{13}C$ NMR (100 MHz, $CDCl_3$) δ (ppm) 151.89 (C2), 150.73 (C22), 143.69 (C6), 136.64 (C4), 127.13 (C5), 125.92 (C15), 119.12 (C3), 92.10 (C7), 79.76 (C8), 31.91, 29.64, 29.49, 29.35, 29.13, 29.00, 28.31, 22.68, 19.40, 14.11 (C9-C21); HRMS ($ESI^+$) m/z calcd for $C_{21}H_{33}N_2O_1^+$329.2587 found 329.2549.

6-pentadecylpicolinaldehyde oxime 10

10

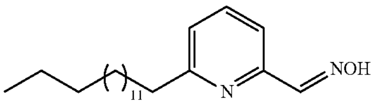

To a degassed solution of oxime 9 (35 mg, 0.107 mmol, 1 equiv) in dry EtOAc (2 mL), 10% Pd/C (3 mg, 0.027 mmol, 0.25 equiv) was added. After flushing with $H_2$ three times, the reaction mixture was stirred at room temperature under $H_2$ (1 atm.) for 2 h. Upon completion, the catalyst was removed by filtration through a short column of celite, the solvent was evaporated, and the residue was purified by column chromatography (EtOAc/PE 6:94) to afford oxime 3 as a white solid (30 mg, 85%); $R_f$(20% EtOAc+PE) 0.65; IR (neat) $v_{max}$ 3187, 3083, 2914, 2849, 1575, 1457, 1160, 985, 777, 718, 656, 517, 479 $cm^{-1}$; $^1H$ NMR (400 MHz, $CDCl_3$) δ (ppm) 8.36 (br s, 1H, OH), 8.25 (s, 1H, $H_{22}$), 7.61-6.54 (m, 2H, $H_3$, $H_4$), 7.11 (dd, J=2.5, 6.1 Hz, 1H, $H_5$), 2.78 (t, J=7.2 Hz, 2H, $H_7$), 1.70 (m, 2H, $H_8$), 1.24 (s, 24H, $H_{12}$-$H_{20}$), 0.86 (t, J=6.6 Hz, 1H, $H_{21}$); $^{13}C$ NMR (100 MHz, $CDCl_3$) δ (ppm) 162.71 (C6), 151.12 (C2), 151.02 (C23), 136.73 (C4), 123.09 (C5), 118.21 (C3), 38.28, 31.92, 29.99, 29.69, 29.56, 29.49, 29.41, 29.36, 22.69, 14.12 (C7-C22). HRMS ($ESI^+$) m/z calcd for $C_{21}H_{37}N_2O^+$333.2900 found 333.2918.

Synthesis of 2-((hydroxyimino)methyl)-6-(Pyridin-1-ium-3-ylethynyl)pyridin-1-ium chloride 13

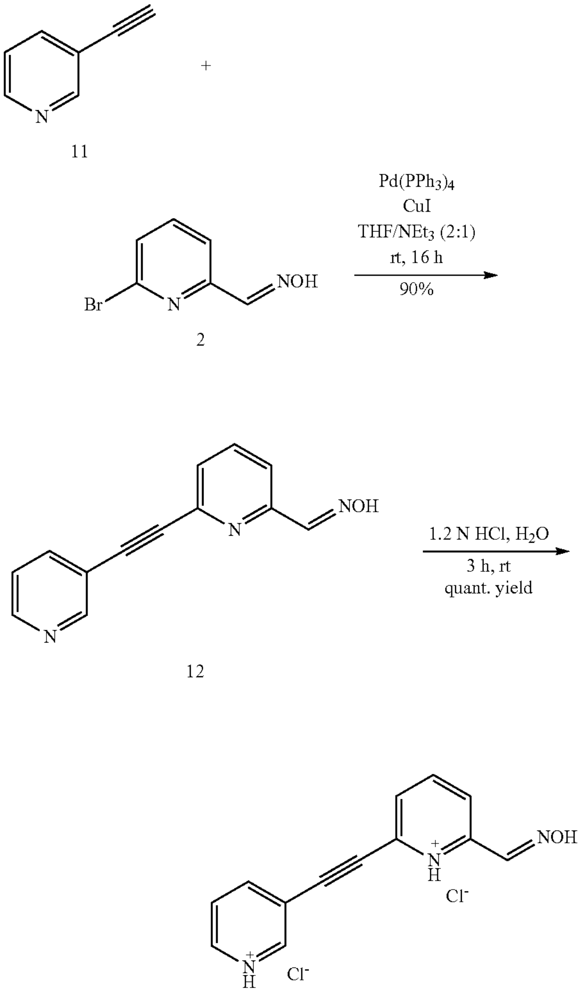

11

2

12

13

3-fluoro-6-(pyridin-3-ylethynyl)picolinaldehyde oxime 12

12

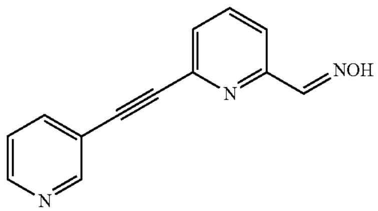

To a degassed solution of oxime 2 (211 mg, 1.05 mmol, 1.05 equiv) in THF/$Et_3N$ (3 mL/3 mL), Pd[$PPh_3$]$_4$ (173 mg, 0.15 mmol, 0.15 equiv) and CuI (57 mg, 0.30 mmol, 0.3 equiv) were added. After degassing the reaction mixture for 5 min at room temperature, the degassed alkyne 11 (103 mg, 1 mmol, 1 equiv) in dry THF (3 mL) was added dropwise and the reaction mixture was stirred at room temperature for 16 h. After completion (monitored by TLC), the reaction mixture was concentrated under reduced pressure and the residue was purified by column chromatography (EtOAc/PE 45:55) to afford the desired coupled oxime 12 as a white solid (200 mg, 90%). $R_f$ (60% EtOAc+PE) 0.35; IR (neat) $v_{max}$ 3065, 2764, 1578, 1561, 1443, 1288, 1143, 1042, 990, 981, 798, 697, 637, 563, 499 $cm^{-1}$; $^1H$ NMR (400 MHz, DMSO-d6) δ (ppm) 11.84 (s, 1H, OH), 8.83 (br s, 1H, $H_{14}$), 8.65 (br s, 1H, $H_{12}$), 8.11-8.04 (m, 2H, $H_{10}$, $H_{15}$), 7.91 (br t, J=7.8 Hz, 1H, $H_4$), 7.83 (br d, J=7.8 Hz, 1H, $H_3$), 7.68 (br d, J=7.8 Hz, 1H, $H_5$), 7.50 (dd, J=4.8, 7.8 Hz, 1H, $H_{11}$); $^{13}C$ NMR (100 MHz, DMSO-d6) δ (ppm) 152.855 (C2), 151.93 (C14), 149.70 (C12), 148.34 (C15), 141.51 (C6), 139.03 (C10), 137.65 (C4), 127.50 (C5), 123.78 (C11), 119.84 (C3), 118.48 (C9), 91.27 (C7), 85.48 (C8); HRMS ($ESI^+$) m/z calcd for $C_{13}H_{10}N_3O^+$224.0818 found 224.0840.

2-((hydroxyimino)methyl)-6-(pyridin-1-ium-3-yl-ethynyl)pyridin-1-ium chloride 13

13

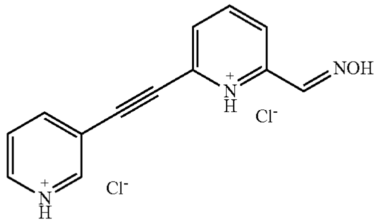

To a compound 12 (40 mg) in water (1 mL), was added 1.2 N HCl (1 mL) and agitated for 2 min and stirred it for 3 h at rt. The reaction mixture was concentrated under reduced pressure to afford HCl salt 13 as a white solid in quantitative yield. IR (neat) $v_{max}$ 3018, 2970, 2502, 2080, 1561, 1465, 1290, 1005, 813, 726, 674, 548, 499 $cm^{-1}$; $^1H$ NMR (400 MHz, $D_2O$) δ (ppm) 9.05 (br s, 1H), 8.83 (br d, J=5.8 Hz, 1H), 8.75 (dt d, J=1.6, 8.3 Hz, 1H), 8.19 (s, 1H), 8.15-8.04 (m, 2H), 7.87 (dd, J=0.6, 8.0 Hz, 1H), 7.81 (br d, J=0.6, 7.8 Hz, 1H); $^{13}C$ NMR (100 MHz, $D_2O$) δ (ppm) 150.85, 149.74, 148.30, 144.75, 142.04, 141.28, 139.9, 130.03, 128.12, 123.99, 122.81, 92.14, 85.20; HRMS ($ESI^+$) m/z calcd for $C_{13}H_{10}N_3O^+$224.0818 found 224.0826.

Synthesis of 6-(4-(naphthalen-1-ylamino)butyl)picolinaldehyde oxime 20

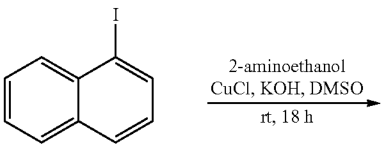

14

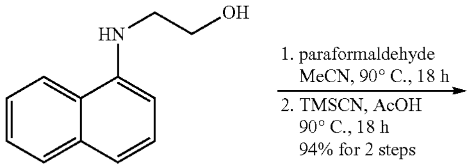

15

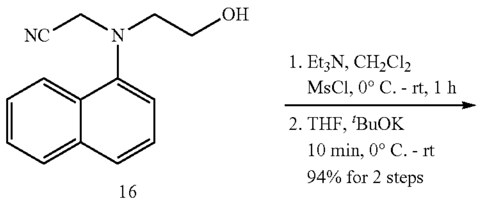

16

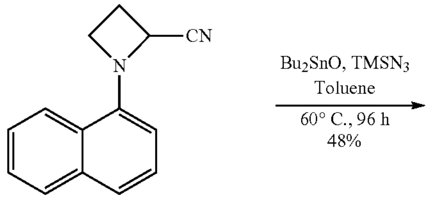

17

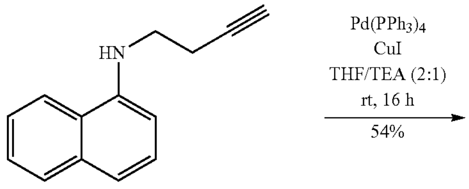

18

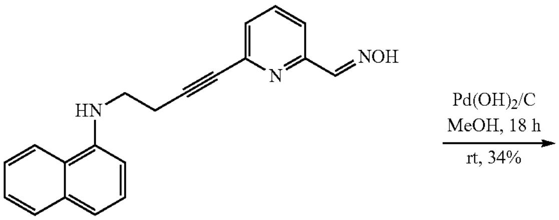

19

-continued

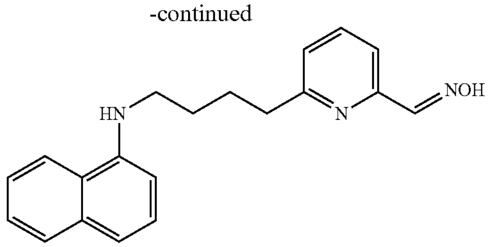

20

2-(Naphthylamino)-ethanol 15

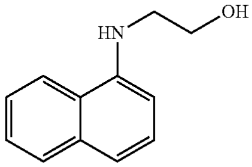

15

Following the procedure from Couty et al.[1] for the synthesis of substituted aromatic amines; To a solution of 1-iodonaphthalene 14 (2.50 g, 9.8 mmol), 2-aminoethanol (1.78 mL, 29.5 mmol), copper chloride (132 mg, 1.0 mmol) and freshly crushed KOH (1.10 g, 19.7 mmol) in DMSO (2 mL) was stirred at rt for 18 h. To the maroon solution was added a saturated aqueous solution of $NH_4Cl$ (5 mL) and the solution was extracted (EtOAc, 3×20 mL). The combined extracts were washed (brine, 20 mL), dried ($MgSO_4$), filtered and concentrated in vacuo. Chromatography on silica gel (30% EtOAc in light petroleum ether) afforded the title compound 15 (1.68 g, 9.0 mmol) as a beige oil. IR (neat) $v_{max}$ 3404, 3051, 2973, 2869, 1581, 785 $cm^{-1}$; $^1$HNMR (400 MHz, $CDCl_3$) δ (ppm) 7.93-7.76 (m, 2H, ArH), 7.52-7.29 (m, 4H, ArH), 6.67 (d, J=7.3 Hz, 1H, CHCNH), 4.01 (t, J=5.1 Hz, 2H, $NHCH_2CH_2OH$), 3.49 (t, J=5.1 Hz, 2H, $NHCH_2CH_2OH$); $^{13}$C NMR (101 MHz, $CDCl_3$) δ (ppm) 142.8, 134.6, 128.7, 126.4, 125.9, 125.0, 123.9, 120.0, 118.5, 105.5, 61.0, 46.6.

2-[(2-Hydroxyethyl)(naphthalen-1-yl)amino]acetonitrile 16

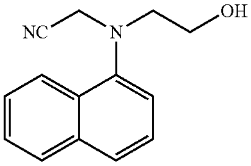

16

Following a procedure from Couty et al.[1] for the N-cyanomethylation of aromatic aminoethanols; To a solution of 2-(naphthylamino)-ethanol 15 (745 mg, 4.0 mmol) and paraformaldehyde (717 mg, 8.0 mmol) in MeCN (20 mL) heated to 90° C. for 18 h. The white suspension was cooled to rt and to the reaction was added TMSCN (1.06 mL, 8.0 mmol) and AcOH (0.46 mL, 8.0 mmol) and the pale yellow reaction solution was stirred for 18 h at 90° C. The reaction was cooled to rt, $H_2O$ (40 mL) was added and the aqueous mixture was extracted ($CH_2Cl_2$, 10 mL). The organic extract was washed with aq. NaOH (1 M, 20 mL), brine (10 mL), dried ($MgSO_4$), filtered and concentrated in vacuo. Chromatography on silica gel (30% EtOAc in light petroleum ether) afforded the title compound 16 (850 mg, 3.8 mmol, 94% over two steps) as a colourless solid. mp=70-71° C. (lit[1]=71-73° C.); IR (neat) $v_{max}$ 3422, 3050, 2956, 2236, 1705, 1418, 802 $cm^{-1}$; $^1$HNMR (400 MHz, $CDCl_3$) δ (ppm) 8.17 (d, J=8.3 Hz, 1H, 8-CH), 7.91 (d, J=7.6 Hz, 1H, 2-CH), 7.75 (d, J=7.6 Hz, 1H, 4-CH), 7.61-7.42 (m, 4H, ArH), 4.17 (s, 2H, $CH_2CN$), 3.78 (br t, J=5.0, 2H, $NCH_2CH_2OH$), 3.54 (t, J=5.0 Hz, 2H, $NCH_2CH_2OH$); $^{13}$C NMR (101 MHz, $CDCl_3$) δ (ppm) 145.8, 134.8, 129.7, 128.5, 126.2, 126.1, 125.8, 125.7, 122.9, 119.1, 116.0, 61.1, 55.1, 44.7.

1-(Naphthalen-1-yl)azetidine-2-carbonitrile 17

17

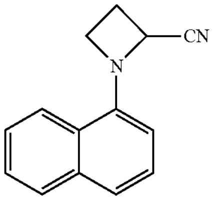

Following a procedure from Couty et al.[1] for formation of aromatic azetidines; To a solution of 2-[(2-hydroxyethyl)(naphthalen-1-yl)amino]acetonitrile 16 (500 mg, 2.2 mmol) and $Et_3N$ (0.77 mL, 5.5 mmol) in $CH_2Cl_2$ (10 mL) at 0° C. was added dropwise MsCl (0.21 mL, 2.6 mmol). The colourless reaction solution was stirred at 0° C. for 30 min and slowly warmed to rt. The reaction was stirred for an additional 30 min at rt. $H_2O$ (20 mL) was added, the organic layer was separated and the aqueous layer was extracted ($CH_2Cl_2$, 20 mL). The combined extracts were washed with aq. HCl (2 M, 10 mL) and brine (10 mL) before being dried ($MgSO_4$), filtered and concentrated in vacuo. The pale yellow residue was directly subjected to the next step and was taken up in anhydrous THF (15 mL). To the solution, at 0° C., was added $^t$BuOK (297 mg, 2.6 mol). The reaction was allowed to slowly warm to rt and $H_2O$ (20 mL) was added. The solution was extracted (EtOAc, 3×20 mL) and the combined organics were washed with brine (20 mL), dried ($MgSO_4$), filtered and concentrated in vacuo. Chromatography on silica gel (10% EtOAc in light petroleum ether) afforded the title compound 17 (850 mg, 3.8 mmol, 94% over two steps) as a colourless solid. mp=129-131° C. (lit[1]=130-131° C.); IR (neat) $v_{max}$ 3433, 3045, 2958, 2248, 1577, 788 $cm^{-1}$; $^1$HNMR (400 MHz, $CDCl_3$) δ (ppm) 7.96-7.82 (m, 2H, ArH), 7.56-7.38 (m, 4H, ArH), 6.75 (d, J=7.3 Hz, 1H, 2-CH), 4.93 (dd, J=8.3, 6.6 Hz, 1H, $NCH_2CH_2CHCN$), 4.51 (ddd, J=8.3, 6.6, 4.9 Hz, 1H, $NCHHCH_2CHCN$), 3.88 (dt, J=8.3, 6.8 Hz, 1H, $NCHHCH_2CHCN$), 2.91-2.80 (m, 1H, 2H, $NCH_2CHHCHCN$), 2.78-2.66 (m, 1H, $NCH_2CHHCHCN$); $^{13}$C NMR (101 MHz, $CDCl_3$) δ (ppm) 145.0, 134.7, 128.6, 126.1, 125.6, 125.2, 125.1, 122.9, 122.5, 118.4, 109.5, 54.3, 51.0, 22.7.

N-(3-Butyn-1-yl)naphthylamine 18

18

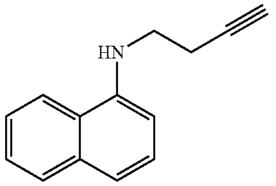

Following a procedure from Couty et al.[2] for formation of aromatic homopropargyl amines from aromatic azetidines; To a solution of 1-(naphthalene-1-yl)azetidine-2-carbonitrile 17 (1.00 g, 4.8 mmol) in toluene (15 mL) was added dibutyltin oxide (298 mg, 1.2 mmol) and $TMSN_3$ (0.95 mL, 7.2 mmol) and the reaction was stirred at 60° C. for 96 h. The brown reaction solution was cooled to rt and concentrated in vacuo. Chromatography on silica gel (2% EtOAc in hexanes) afforded the title compound 18 (454 mg, 2.3 mmol, 48%) as a colourless oil. IR (neat) $v_{max}$ 3293, 3050, 2975, 2117, 1690, 767 $cm^{-1}$; $^1$HNMR (400 MHz, $CDCl_3$) δ (ppm) 7.90-7.79 (m, 2H, 5-CH, 8-CH), 7.57-7.29 (m, 4H, 3-CH, 4-CH, 6-CH, 7-CH), 6.66 (d, J=7.3 Hz, 1H, 2-CH), 3.50 (t, J=6.5 Hz, 2H, $NHCH_2CH_2CCH$), 2.69 (td, J=6.5, 2.7 Hz, 2H, $NHCH_2CH_2CCH$), 2.11 (t, J=2.7, 1H, $NHCH_2CH_2CCH$); $^{13}$C NMR (101 MHz, $CDCl_3$) δ (ppm) 146.7, 134.4, 128.7, 126.4, 125.9, 125.0, 123.8, 121.0, 119.9, 118.3, 85.2, 70.4, 27.4, 18.9.

N-(4-{6-[(hydroxyimino)methyl]pyridine-2-yl}but-3-yn-1-yl)naphthalene-1-amine 19

19

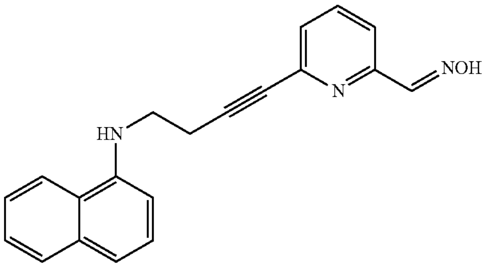

To a degassed solution of N-(3-Butyn-1-yl)naphthylamine 18 (400 mg, 2.0 mmol) in anhydrous THF/$Et_3N$ (7 mL/3 mL) was added $Pd(PPh_3)_4$ (238 mg, 0.2 mmol) and CuI (78 mg, 0.4 mmol). To the resulting orange reaction mixture was added dropwise a degassed solution of 6-bromopicolinaldehyde oxime 2 (453 mg, 2.2 mmol) in anhydrous THF (20 mL). The brown solution was stirred for 16 h at rt. The reaction was concentrated in vacuo. Chromatography on silica gel (hexanes to 10% EtOAc in hexanes) afforded the title compound 19 (350 mg, 54%) as an orange solid: mp=143-144° C.; $^1$HNMR (400 MHz, $CDCl_3$) δ (ppm) 8.28 (s, 1H, NOH), 7.95-7.73 (m, 4H, ArH), 7.67 (t, J=7.8 Hz, 1H, 3-CH), 7.53-7.33 (m, 4H, ArH), 6.70 (d, J=7.8 Hz, 1H, 2-CH), 3.66 (t, J=6.7 Hz, 2H, $NHCH_2CH_2$), 2.96 (t, J=6.7 Hz, 2H, $NHCH_2CH_2$); $^{13}$C NMR (101 MHz, $CDCl_3$) δ (ppm) 152.0, 150.5, 143.1, 142.1, 136.8, 134.4, 128.7, 127.8, 127.3, 126.4, 125.9, 125.0, 123.8, 120.0, 119.8, 105.2, 88.6, 81.4, 42.6, 19.8; IR (neat) v 3350, 3152, 3047, 2864, 2645, 2200 $cm^{-1}$, HRMS (ESI)$^+$ m/z for $C_{20}H_{18}N_3O^+$ calculated 316.1444, found 316.1445.

N-(4-{6-[(hydroxyimino)methyl]pyridine-2-yl}but-3-yn-1-yl)naphthalene-1-amine 20

20

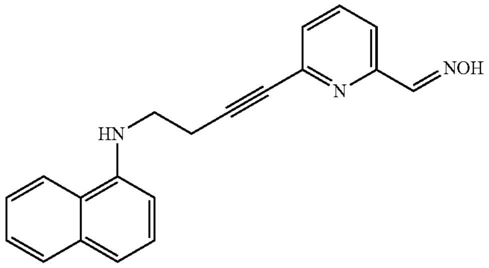

To a degassed suspension of N-(4-{6-[(1E)-(hydroxyimino)methyl]pyridine-2-yl}but-3-yn-1-yl)naphthalene-1-amine 19 (173 mg, 0.5 mmol) in anhydrous methanol (10 mL), was added Pearlman's catalyst (77 mg, 0.5 mmol). The reaction vessel was evacuated and flushed with hydrogen gas five times. The black reaction mixture was stirred for 18 h at rt. The catalyst was removed by filtration through Celite and the solvent was removed in vacuo. Chromatography on silica gel (50% EtOAc in hexanes) to afford the title compound 20 (60 mg, 34%) as a colourless solid: mp=151-152° C.; IR (neat) $v_{max}$ 3351, 3047, 2867, 2642, I $cm^{-1}$; $^1$HNMR (400 MHz, $CDCl_3$) δ (ppm) 8.21 (s, 1H, NOH), 7.77-7.67 (m, 2H, ArH), 7.60-7.49 (m, 2H, ArH), 7.41-7.30 (m, 2H, ArH), 7.26 (t, J=8.2 Hz, 1H, NCCHCHCH), 7.15 (d, J=8.2 Hz, 1H, NCCHCHCH), 7.09 (dd, J=7.1, 1.7 Hz, 1H, 7-CH), 6.53 (d, J=7.5 Hz, 1H, 2-CH), 3.26 (t, J=6.9 Hz, 2H, $NHCH_2CH_2CH_2CH_2$), 2.85 (t, J=6.7 Hz, 2H, $NHCH_2CH_2CH_2CH_2$), 2.00-1.65 (m, 4H, $NHCH_2CH_2CH_2CH_2$); $^{13}$C NMR (101 MHz, $CDCl_3$) δ (ppm) 162.0, 151.1, 151.0, 143.4, 137.1, 134.3, 128.6, 126.6, 125.7, 124.7, 123.4, 123.3, 119.9, 118.6, 117.3, 104.4, 44.1, 37.7, 28.8, 27.6; HRMS (ESI)$^+$ m/z for $C_{20}H_{22}N_3O^+$ calculated 320.1757, found 320.1759.

REFERENCES

1. Couty et al. J. Org. Chem. 2016, 81, 2899-2910

2. Couty et al. Chem. Comms. 2016, 52, 10072-10075

Synthesis of methyl 3-hydroxy-6-(4-(quinoline-4-ylamino)butyl)picolinate 26

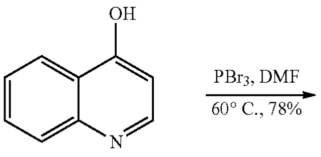

21

-continued

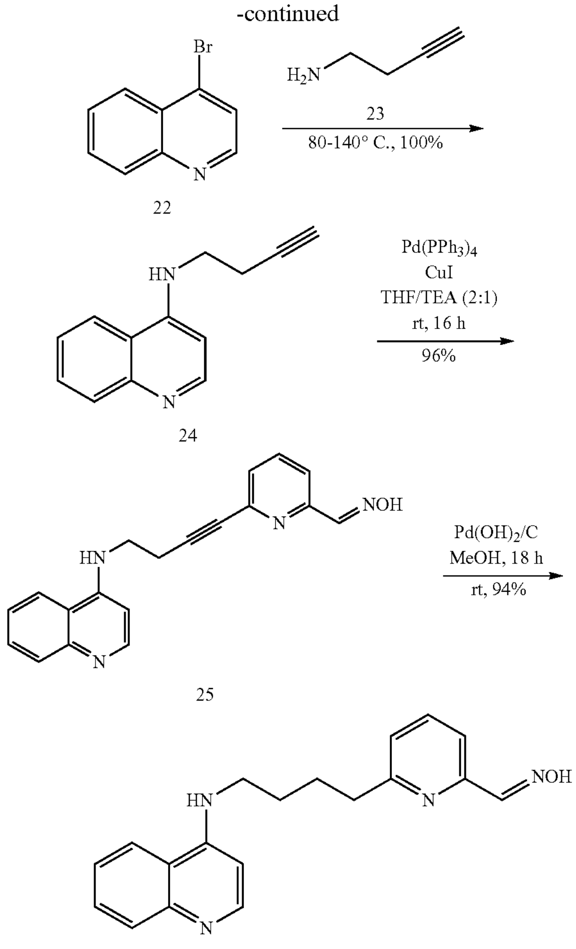

22

24

25

26

4-Bromoquinoline 22

22

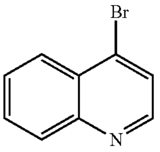

Following the procedure from Margolis et al.[1] for the synthesis of bromoquinolines; To a solution of 4-quinolinol 21 (5.00 g, 34.4 mmol) in DMF (50 mL) at 60° C. was added dropwise $PBr_3$ (3.34 mL, 35.5 mmol). Upon addition, a colour change was observed from yellow to vivid orange, with effervescence. The orange reaction mixture was stirred at 45° C. for 45 min. The solution was cooled to rt and diluted with $H_2O$ (20 mL) and a saturated solution of aqueous $NaHCO_3$ was slowly added to basify the reaction mixture to pH 10. The solution was extracted with $CH_2Cl_2$ (5×20 mL), then the organic solutions were combined and washed with $H_2O$ (20 mL), dried ($MgSO_4$), filtered and concentrated in vacuo. Chromatography on silica gel (EtOAc) afforded the title compound 22 (5.56 g, 26.7 mmol, 78%) as a cream solid. Physical and spectroscopic data are consistent with reported values.[2] mp=28-29° C. (lit.[2] 29.5-30.5° C.); IR (neat) ν 3062, 1615, 1058 $cm^{-1}$; $^1$HNMR (400 MHz, $CDCl_3$) δ 8.68 (d, J=4.6 Hz, 1H, NCH), 8.20 (dd, J=8.4, 0.9 Hz, 1H, NCCHCHCHCH), 8.11 (d, J=8.4 Hz, 1H, NCCHCHCHCH), 7.78 (ddd, J=8.4, 7.0, 1.4 Hz, 1H, NCCHCH), 7.71 (d, J=4.6 Hz, 1H, NCHCH), 7.66 (ddd, J=8.4, 7.0, 1.4 Hz, 1H, NCCHCHCHCH); $^{13}$C NMR (100 MHz, $CDCl_3$) δ 149.9, 149.0, 134.2, 130.4, 129.9, 127.9, 127.9, 126.8, 125.1.

N-(But-3-yn-1-yl)quinolin-4-amine 24

24

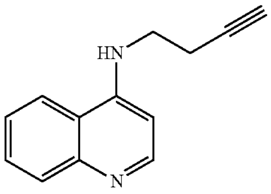

Following a procedure adapted from Musonda et al.[3] for the synthesis of alkylated quinolines; Commercially available 3-butyn-1-amine 23 (4.72 mL, 57.7 mmol) was added to 4-bromoquinoline 22 (3.00 g, 14.4 mmol) to form a thin cream-coloured paste. The paste was heated to 80° C. for 1 h without stirring. The temperature was increased to 140° C. and the paste was heated for 18 h with stirring. The viscous, brown reaction mixture was cooled to rt and purified by chromatography on silica gel (20% MeOH in EtOAc) to afford the title compound 24 (2.82 g, 14.4 mmol, 100%) as a cream solid: mp=165-166° C.; IR (neat) $\nu_{max}$ 3281, 3169, 3067, 1573, 1151 $cm^{-1}$; $^1$H NMR (400 MHz, DMSO-$d_6$) δ 8.45 (d, J=5.9 Hz, 1H, NCH), 8.30 (dd, J=8.3, 1.2 Hz, 1H, NCCHCHCHCH), 7.93 (br. s, 1H, NH), 7.82 (dd, J=8.3, 1.2 Hz, 1H, NCCHCHCHCH), 7.71 (ddd, J=8.3, 7.0, 1.2 Hz, 1H, NCCHCHCHCH), 7.51 (ddd, J=8.3, 7.0, 1.2 Hz, 1H, NCCHCHCHCH), 6.63 (d, J=5.9 Hz, 1H, NCHCH), 3.54 (q, J=7.0 Hz, 2H, $NHCH_2CH_2CCH$), 2.91 (t, J=2.7 Hz, 1H, $NHCH_2CH_2CCH$), 2.58 (td, J=6.8, 2.7 Hz, 2H, $NHCH_2CH_2CCH$); $^{13}$C NMR (100 MHz, DMSO-$d_6$) δ 151.3, 148.2, 145.1, 130.2, 126.4, 124.7, 122.1, 118.1, 98.3, 82.1, 72.6, 41.4, 17.8; HRMS (ESI)$^+$ m/z calcd for $C_{13}H_{13}N_2^+$197.1073, found 197.1072.

6-(4-(quinolin-4-ylamino)but-1-yn-1-yl)picolinaldehyde oxime 25

25

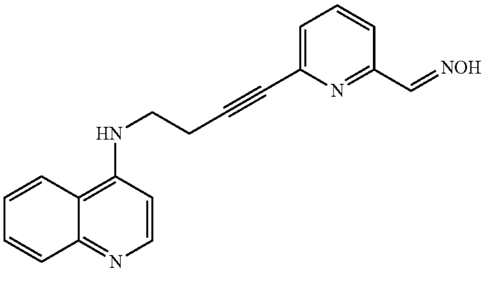

To a degassed solution of N-(but-3-yn-1-yl)quinoline-4-amine 24 (1.00 g, 5.1 mmol) in anhydrous THF/$Et_3N$ (50 mL/15 mL) was added $Pd(PPh_3)_4$ (588 mg, 0.5 mmol) and CuI (194 mg, 1.0 mmol). To the resulting orange reaction mixture was added dropwise a degassed solution of 6-bromopicolinaldehyde oxime 2 (1.13 g, 5.6 mmol) in anhydrous THF (20 mL). The brown solution was stirred for 18 h at rt. The reaction was concentrated in vacuo. Chromatography on silica gel (20% MeOH in EtOAc) afforded the title compound 25 (1.55 g, 4.9 mmol, 96%) as an orange solid: mp=202-203° C. (decomposed); IR (neat) $v_{max}$ 3291, 3068, 2947, 2241, 1617, 1222, 1051 $cm^{-1}$; $^{1}H$ NMR (400 MHz, DMSO-$d_6$) δ 11.90-11.69 (m, 1H, CHNOH), 8.43 (br d, J=5.4 Hz, 1H, NCH), 8.23 (d, J=8.3 Hz, 1H, NCCH), 8.03 (s, 1H, CHNOH), 7.85-7.65 (m, 4H, ArH), 7.52-7.38 (m, 3H, ArH), 6.60 (d, J=5.4 Hz, 1H, NCHCH), 3.61 (q, J=6.7 Hz, 2H, $NHCH_2CH_2$), 2.88 (t, J=6.7 Hz, 2H, $NHCH_2CH_2$); $^{13}C$ NMR (100 MHz, DMSO-$d_6$) δ 152.5, 150.3, 149.8, 148.4, 147.8, 142.4, 137.8, 129.0, 128.6, 126.8, 124.1, 121.7, 118.9, 118.7, 98.5, 88.7, 81.1, 48.6, 18.6; HRMS $(ESI)^+$ m/z calcd for $C_{19}H_{17}N_4O^+$317.1397, found 317.1396.

Methyl 3-hydroxy-6-(4-(quinoline-4-ylamino)butyl) picolinate 26

26

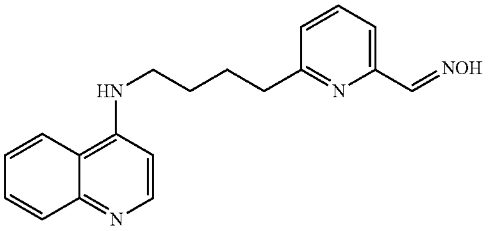

To a degassed suspension of (E)-6-(4-(quinolin-4-ylamino)but-1-yn-1-yl)picolinaldehyde oxime 25 (575 mg, 1.8 mmol) in anhydrous methanol (20 mL), was added Pearlman's catalyst (255 mg, 1.8 mmol). The reaction vessel was evacuated and flushed with hydrogen gas five times. The black reaction mixture was stirred for 18 h at rt. The catalyst was removed by filtration through Celite and the solvent was removed in vacuo to afford the title compound 26 (550 mg, 1.7 mmol, 94%) as a cream solid: mp=218-219° C.; IR (neat) $v_{max}$ 3145, 3026, 2985, 1593, 1224, 1026, 658 $cm^{-1}$; $^{1}H$ NMR (400 MHz, $D_2O$) δ 8.15 (s, 1H, CHNOH), 8.01 (d, J=7.1 Hz, 1H, NCH), 7.89-7.49 (m, 7H, ArH), 6.62 (d, J=7.1 Hz, 1H, NCHCH), 3.54 (t, J=6.6 Hz, 2H, $NHCH_2CH_2CH_2CH_2$), 3.09 (t, J=7.2 Hz, 2H, $NHCH_2CH_2CH_2CH_2$), 1.99-1.76 (m, 4H, $NHCH_2CH_2CH_2CH_2$); $^{13}C$ NMR (100 MHz, $D_2O$) δ 156.1, 146.7, 145.0, 142.7, 141.7, 137.6, 134.1, 127.5, 127.4, 123.2, 122.3, 122.1, 120.2, 116.8, 98.2, 42.9, 33.1, 26.1, 17.2; HRMS $(ESI)^+$ m/z calcd for $C_{19}H_{21}N_4O^+$321.1710, found 3321.1713.

REFERENCES

1. Margolis, B. J. et al. *J. Org. Chem.* 2007, 72, 2232-2235.
2. Charette, A. B., et al. *J. Org. Chem.* 2017, 82, 5046-5067
3. Musonda, C. C et al. *Bioorg. Med. Chem. Lett.* 2007, 17, 4733-4736.

Synthesis of 6-(4-((5-fluoroquinolin-4-yl)amino) butyl)picolinaldehyde oxime 31

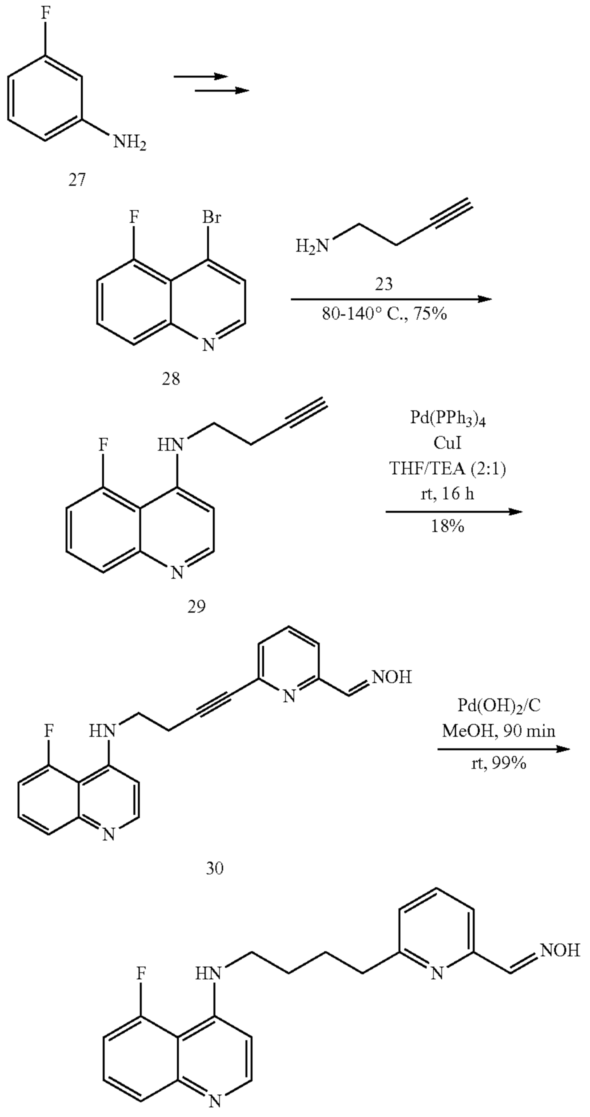

27 28 29 30 31

4-Bromo-5-fluoroquinoline 28

28

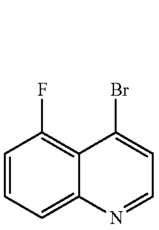

Following an adapted procedure from Kilpin Guy et al.[1] for the synthesis of substituted quinolines from anilines and Pulley et al.[2] for the synthesis of bromo-quinolines from quinolinols; to a solution of m-fluoroaniline 27 (6.00 g, 54.0 mmol) in EtOH (100 mL) at rt was added Meldrum's acid (9.49 g, 65.9 mmol) and triethyl orthoformate (21.3 mL, 128.0 mmol). The yellow solution was stirred at 90° C. for 2.5 h. The solution was cooled to 0° C. and the resulting yellow solid was filtered and washed with cold EtOH (20 mL). The resulting pale yellow solid was dried and added slowly over 5 min into refluxing diphenyl ether (50 mL) at 280° C. Upon addition, large quantities of white gas were observed and the colourless solution turned orange/brown. Reflux was maintained for 5 min and the reaction mixture was cooled to rt. The solution developed a much darker brown colour during this time. Petroleum ether (50 mL) was added to the solution and the resulting brown crystals that were evolved, were separated by filtration. Chromatography on silica gel (10% MeOH in EtOAc) afforded an inseparable mixture of 5-fluoroquinolin-4-ol and 7-fluoroquinolin-4-ol (approximately 9:1 by $^{19}$FNMR, 7.76 g, 47.5 mmol). This mixture was directly subjected to the next step.

To a solution of the inseparable mixture of regioisomers of 5-fluoroquinolin-4-ol and 7-fluoroquinolin-4-ol (4.00 g, 24.5 mmol) in DMF (30 mL) was added phosphorus tribromide (1.86 mL, 19.7 mmol) at 60° C. and the mixture was stirred at 45° C. for 45 min. After cooling to rt, $H_2O$ (25 mL) was added and a saturated solution of aqueous $Na_2CO_3$ was added to adjust the pH of the solution to 10. The resulting crystals were washed with $H_2O$ (10 mL). Chromatography on silica gel (25% EtOAc in hexanes) gave only 4-bromo-5-fluoroquinoline 28 (2.50 g, 11.1 mmol, 61% over three steps) as an orange solid. mp=89-90° C.; IR (neat) ν 3091, 3041, 1621 cm$^{-1}$; $^1$HNMR (400 MHz, $CDCl_3$) δ 8.67 (d, J=4.6 Hz, 1H, NCH), 8.22 (dd, J=9.2, 5.9 Hz, 1H, NCCH), 7.75 (dd, J=9.2, 2.7 Hz, 1H, NCCHCHCH), 7.68 (d, J=4.6 Hz, 1H, NCHCH), 7.44 (ddd, J=9.2, 5.9, 2.7 Hz, 1H, NCCHCH); $^{13}$C NMR (100 MHz, $CDCl_3$) δ 161.9, 150.6, 149.6, 133.7, 128.9, 124.7, 124.1, 118.0, 113.1; $^{19}$FNMR (376 MHz, $CDCl_3$) δ 108.7; HRMS (ESI)$^+$ m/z for $C_9H_6BrFN^+$ calculated 225.9662, found 225.9658.

N-(but-3-yn-1-yl)-5-fluoroquinolin-4-amine 29

29

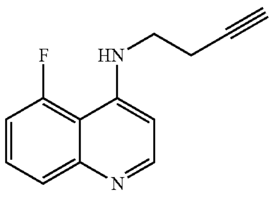

Following a procedure adapted from Musonda et al. for the synthesis of alkylated quinolines;[3] 3-butyn-1-amine 23 (0.55 mL, 6.6 mmol) was added to 4-bromo-5-fluoroquinoline 28 (1.50 g, 6.6 mmol) to form a thin orange-coloured paste. The paste was heated to 100° C. for 18 h with stirring. The reaction was heated to 120° C. for a further 2 h. The viscous, brown reaction mixture was cooled to rt and purified by chromatography on silica gel (100% EtOAc to 20% MeOH in EtOAc) to afford the title compound 29 (1.06 g, 4.9 mmol, 75%) as a cream solid. mp=225-226° C.; IR (neat) $ν_{max}$ 3079, 2911, 2240, 1966 cm$^{-1}$; $^1$HNMR (400 MHz, DMSO-$d_6$) δ 8.39 (d, J=5.4 Hz, 1H, NCH), 8.27 (dd, J=10.8, 8.3 Hz, 1H, NCCH), 7.47 (dd, J=10.8, 2.5 Hz, 1H, NCCHCHCH), 7.44-7.39 (m, 1H, $NHCH_2CH_2CCH$), 7.35 (ddd, J=10.8, 8.3, 2.5 Hz, 1H, NCCHCHCH), 6.49 (d, J=5.4 Hz, 1H, NCHCH), 3.45 (q, J=7.1 Hz, 2H, $NHCH_2CH_2CCH$), 2.88 (t, J=2.7 Hz, 1H, $NHCH_2CH_2CCH$), 2.55 (td, J=7.1, 2.7 Hz, 2H, $NHCH_2CH_2CCH$); $^{13}$C NMR (100 MHz, DMSO-$d_6$) δ 163.4, 160.9, 151.9, 149.7, 124.5, 115.8, 113.5, 112.2, 98.2, 82.2, 72.4, 41.2, 17.7; $^{19}$FNMR (376 MHz, DMSO-$d_6$) δ 112.1; HRMS (ESI)$^+$ m/z calcd for $C_{13}H_{12}FN_2^+$215.0979, found 215.0983 Da.

6-(4-((5-fluoroquinolin-4-yl)amino)but-1-yn-1-yl) picolinaldehyde oxime 30

30

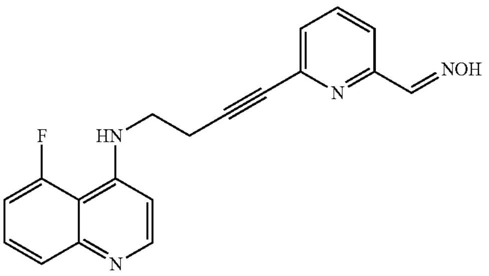

To a degassed solution of N-(but-3-yn-1-yl)-5-fluoroquinolin-4-amine 29 (0.50 g, 2.3 mmol) in anhydrous THF/$Et_3N$ (7 mL/3 mL) was added $Pd(PPh_3)_4$ (270 mg, 0.2 mmol) and CuI (89 mg, 0.4 mmol). To the resulting orange reaction mixture was added dropwise a degassed solution of 6-bromopicolinaldehyde oxime 2 (516 mg, 2.6 mmol) in anhydrous THF (20 mL). The brown solution was stirred for 16 h at rt. The reaction was concentrated in vacuo. Chromatography on silica gel (EtOAc) afforded the title compound 30 (140 mg, 0.4 mmol, 18%) as pale cream solid: mp=168-169° C.; IR (neat) $ν_{max}$ 3500, 3435, 3034, 2960, 2239, 1966, 1599, 991 cm$^{-1}$; $^1$H NMR (400 MHz, DMSO-$d_6$) δ 11.79 (s, 1H, CHNOH), 8.42 (d, J=5.4 Hz, 1H, NCHCH), 8.30 (dd, J=9.2, 7.1 Hz, 1H, NCCHCHCHCF), 8.02 (s, 1H, CHNOH), 7.83-7.69 (m, 2H, ArH), 7.53 (t, J=5.6 Hz, 1H, $NHCH_2CH_2$), 7.48 (dd, J=10.8, 2.7 Hz, 1H, NCCHCHCH), 7.41 (d, J=7.1 Hz, 1H, NCCHCHCHCF), 7.35 (td, J=8.7, 2.7 Hz, 1H, NCCHCHCH), 6.58 (d, J=5.4 Hz, 1H, NCHCH), 3.66-3.51 (m, 2H, $NHCH_2CH_2$), 2.86 (t, J=7.0 Hz, 2H, $NHCH_2CH_2$); $^{13}$C NMR (100 MHz, DMSO-$d_6$) δ 163.4, 160.9, 152.4, 151.9, 149.8, 148.4, 142.4, 137.3, 126.9, 124.5, 119.0, 115.9, 113.5, 112.2, 98.4, 88.7, 81.1, 41.0, 18.6; $^{19}$FNMR (376 MHz, DMSO-$d_6$) δ 111.9; HRMS (ESI)$^+$ m/z calcd for $C_{19}H_{16}FN_4O^+$335.1303, found 335.1298.

6-(4-((5-fluoroquinolin-4-yl)amino)butyl)picolinaldehyde oxime 31

31

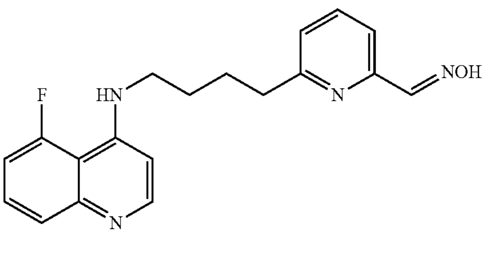

To a degassed suspension of 6-(4-((5-fluoroquinolin-4-yl) amino)but-1-yn-1-yl)picolinaldehyde oxime 30 (50 mg, 0.1 mmol) in anhydrous methanol (5 mL), was added Pearlman's catalyst (21 mg, 0.1 mmol). The reaction vessel was evacuated and flushed with hydrogen gas five times. The black reaction mixture was stirred for 18 h at rt. The catalyst was removed by filtration through Celite and the solvent was removed in vacuo to afford the title compound 31 (50 mg, 0.1 mmol, 99%) as a cream solid: mp=206-207° C.; IR (neat) $v_{max}$ 3247, 2935, 2859, 1978, 1584, 806 $cm^{-1}$; $^{1}H$ NMR (400 MHz, $D_2O$) δ 8.44 (t, J=8.1 Hz, 1H, NCCHCHCH), 8.19 (d, J=7.3 Hz, 1H, NCHCH), 8.16-8.13 (m, 2H, CHNOH, $NHCH_2CH_2CH_2CH_2$), 7.91-7.81 (m, 2H, NCCHCHCHCF, NCCHCHCHCF), 7.70 (d, J=8.1 Hz, 1H, NCCHCHCH), 7.42-7.32 (m, 2H, NCCHCHCH), 6.70 (d, J=7.3 Hz, NCHCH), 3.58 (t, J=6.8 Hz, 2H, $NHCH_2CH_2CH_2CH_2$), 3.12 (t, J=7.7 Hz, 2H, $NHCH_2CH_2CH_2CH_2$), 2.01-1.76 (m, 4H, $NHCH_2CH_2CH_2CH_2$); $^{13}C$ NMR (100 MHz, $D_2O$) δ 166.0, 136.5, 161.5, 159.1, 155.8, 146.5, 141.9, 139.0, 127.0, 125.6, 124.0, 116.2, 113.5, 105.1, 98.0, 42.8, 39.9, 26.9, 25.9; $^{19}F$NMR (376 MHz, $D_2O$) δ 103.1; HRMS $(ESI)^+$ m/z calcd for $C_{19}H_{22}FN_4O^+$339.1980, found 339.1980.

REFERENCES

1. Kiplin Guy, R. et al. *Bioorg. Med. Chem. Lett.* 2005, 15, 1015-1018
2. Pulley et al. *J. Org. Chem.* 2007, 72, 2232-2235
3. Musonda, C. C. et al. *Bioorg. Med. Chem. Lett.* 2007, 17, 4733-4736

Synthesis of 6-(4-((8-methoxyquinolin-4-yl)amino) butyl)picolinaldehyde oxime 37

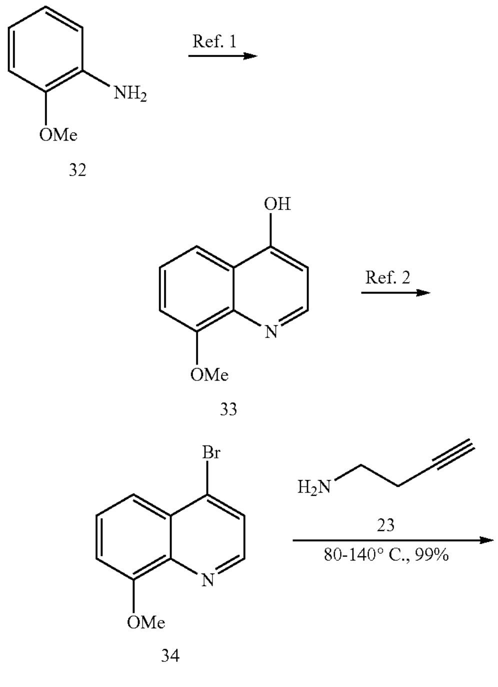

32

33

23

34

-continued

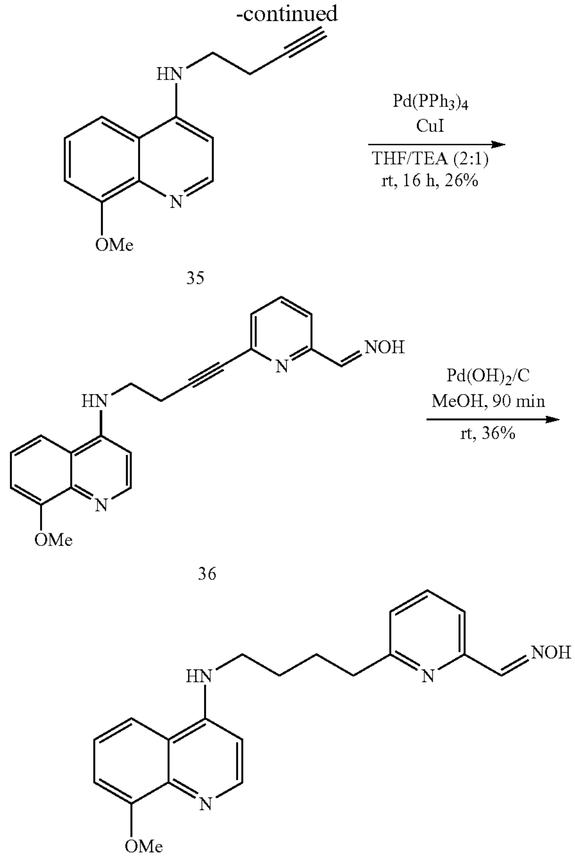

35

36

37

8-Methoxyquinolin-4-ol 33

33

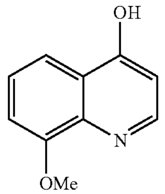

Following an adapted procedure from Kilpin Guy et al.[1] for the synthesis of substituted quinolines from anilines; to a solution of o-anisidine 32 (2.50 g, 20.3 mmol) in EtOH (20 mL) at rt was added Meldrum's acid (3.57 g, 24.8 mmol) and triethyl orthoformate (8.00 mL, 48.0 mmol). The yellow solution was stirred at 90° C. for 2.5 h. The solution was cooled to 0° C. and the resulting yellow solid was filtered and washed with cold EtOH (20 mL). The resulting pale yellow solid was dried and added slowly over 5 min into refluxing diphenyl ether (50 mL) at 280° C. Upon addition, large quantities of white gas were observed and the colourless solution turned orange/brown. Reflux was maintained for 5 min and the reaction mixture was cooled to rt. The solution developed a much darker brown colour during this time. Petroleum ether (50 mL) was added to the solution and the resulting yellow crystals that were evolved, were separated by filtration. Chromatography on silica gel (5% MeOH in EtOAc) afforded 8-methoxyquinolin-4-ol 33 (7.76 g, 47.5 mmol) as a pale orange solid: mp=168° C. (lit[2]: 168-169° C.); IR (neat) ν 2921, 2851, 1272, 1041 $cm^{-1}$; $^1$HNMR (400 MHz, DMSO-$d_6$) δ (ppm) 11.35 (s, 1H, OH), 7.58-7.70 (m, 1H, NCH), 7.38-7.43 (m, 1H, ArH), 7.23-7.27 (m, 2H, OHCCCH, OMeCCH), 6.95-7.08 (m, 1H, OHCCH), 3.99 (s, 3H, OMe); $^{13}$C NMR (101 MHz, DMSO-$d_6$) δ (ppm) 177.1, 149.0, 139.3, 130.5, 123.2, 119.1, 116.7, 111.4, 109.6, 56.6; HRMS (ESI)$^+$ m/z for $C_{10}H_{10}NO_2^+$ calculated 176.0706, found 176.0707.

4-Bromo-8-methoxyquinoline 34

34

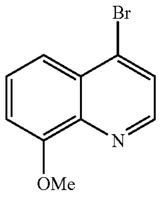

Following an adapted procedure from Pulley et al.[3] for the synthesis of bromo-quinolines from quinolinols; to a solution of 8-methoxyquinolin-4-ol 33 (2.50 g, 14.3 mmol) in DMF (20 mL) was added phosphorus tribromide (1.54 mL, 16.4 mmol) at 60° C. and the mixture was stirred at 45° C. for 45 min. After cooling to rt, $H_2O$ (25 mL) was added and a saturated solution of aqueous $Na_2CO_3$ was added to adjust the pH of the solution to 10. The resulting cream-coloured crystals were filtered and washed with $H_2O$ (10 mL) giving 4-bromo-5-fluoroquinoline 34 (2.58 g, 10.8 mmol, 76%) as cream solid. mp=99-101° C.; IR (neat) $v_{max}$ 1252, 1085 $cm^{-1}$; $^1$HNMR (400 MHz, $CDCl_3$) δ (ppm) 8.69 (d, J=4.6 Hz, 1H, NCH), 7.78 (d, J=8.1 Hz, 1H, BrCCCH), 7.75 (d, J=4.8 Hz, 1H, BrCCH), 7.58 (t, J=8.2 Hz, 1H, ArH), 7.14 (d, J=8.0 Hz, 1H, ArH), 4.12 (s, 3H, OMe); $^{13}$C NMR (101 MHz, $CDCl_3$) δ (ppm) 155.5, 148.5, 134.1, 129.0, 128.0, 125.8, 118.5, 108.5, 56.3; HRMS (ESI)$^+$ m/z for $C_{10}H_9BrNO^+$ calculated 237.9862, found 237.9865.

N-(but-3-yn-1-yl)-8-methoxyquinolin-4-amine 35

35

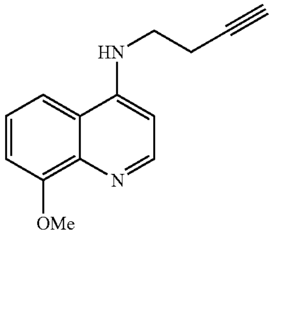

Following a procedure adapted from Musonda et al. for the synthesis of alkylated quinolines;[4] 3-butyn-1-amine 23 (1.20 mL, 14.7 mmol) was added to 4-bromo-8-methoxyquinoline 34 (0.70 g, 2.9 mmol) to form a orange/yellow-coloured paste. The paste was heated to 80° C. for 1 h without stirring. The temperature was increased to 100° C. for 18 h with stirring. The viscous, brown reaction mixture was cooled to rt and purified by chromatography on alumina (basic) gel (10% MeOH in EtOAc) to afford the title compound 35 (0.80 g, 2.9 mmol, 99%) as a pale orange solid. mp=154-155° C.; IR (neat) $v_{max}$ 3279, 2938, 2240, 753 $cm^{-1}$; $^1$HNMR (400 MHz, DMSO-$d_6$) δ (ppm) 8.36 (d, J=5.4 Hz, 1H, NCH), 7.73 (d, J=7.8 Hz, 1H, MeOC-CHCHCH), 7.35 (t, J=8.1 Hz, 1H, MeOCCHCH), 7.10 (d, J=7.3 Hz, 1H, OMeCCH), 6.55 (d, J=5.4 Hz, 1H, NCHCH), 3.91 (s, 3H, OMe), 3.39-3.53 (m, 2H, $CH_2CH_2$CCH), 2.89 (t, J=2.6 Hz, 1H, $CH_2CH_2$CCH), 2.56 (td, J=7.1, 2.7 Hz, 2H, $CH_2CH_2$CCH); $^{13}$C NMR (101 MHz, DMSO-$d_6$) δ (ppm) 155.2, 149.9, 148.8, 139.6, 124.3, 119.6, 113.3, 108.5, 99.1, 82.5, 72.6, 55.8, 41.5, 18.0; HRMS (ESI)$^+$ m/z calcd for $C_{14}H_{15}N_2O^+$227.1179, found 227.1183.

6-(4-((8-methoxyquinolin-4-yl)amino)but-1-yn-1-yl) picolinaldehyde oxime 36

36

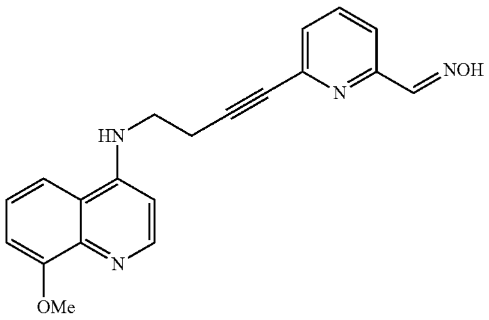

To a degassed solution of N-(but-3-yn-1-yl)-8-methoxy-quinolin-4-amine 35 (1.00 g, 4.4 mmol) in anhydrous THF/$Et_3N$ (7 mL/3 mL) was added $Pd(PPh_3)_4$ (511 mg, 0.4 mmol) and CuI (168 mg, 0.9 mmol). To the resulting orange reaction mixture was added dropwise a degassed solution of 6-bromopicolinaldehyde oxime 2 (977 mg, 4.8 mmol) in anhydrous THF (20 mL). The brown solution was stirred for 16 h at rt. The reaction was concentrated in vacuo. Chromatography on alumina (basic) gel (10% MeOH in EtOAc) afforded the title compound 36 (400 mg, 1.1 mmol, 26%) as yellow solid: mp=171-172° C.; IR (neat) $v_{max}$ 3084, 2900, 2236, 1617, 1277, 745 $cm^{-1}$; $^1$H NMR (400 MHz, DMSO-$d_6$) δ 11.79 (s, 1H, CHNOH), 8.35 (d, J=6.1 Hz, 1H, NCHCH), 7.98 (m, 2H, NCC(OMe)CHCHCH, CHNOH), 7.78 (t, J=7.8 Hz, 1H, NCCHCHCH), 7.72 (d, J=7.8 Hz, 1H, NCCHCHCH), 7.49 (d, J=8.2 Hz, 1H, NCC(OMe)CHCHCH), 7.39 (d, J=7.8 Hz, 1H, NCCHCHCH), 7.29 (d, J=8.2 Hz, 1H, NCC(OMe)CHCHCH), 6.84 (d, J=6.1 Hz, 1H, NCHCH), 3.99 (s, 3H, OMe), 3.71 (br t, J=7.0, 2H, $NHCH_2CH_2$), 2.90 (t, J=7.0 Hz, 2H, $NHCH_2CH_2$); $^{13}$C NMR (100 MHz, DMSO-$d_6$) δ 152.6, 152.5, 152.1, 148.3, 145.1, 142.3, 137.3, 134.2, 126.8, 125.4, 119.0, 118.5, 113.7, 110.3, 99.0, 88.3, 81.3, 56.1, 48.5, 18.7; HRMS (ESI)$^+$ m/z calcd for $C_{20}H_{19}N_4O_2^+$347.1503, found 347.1506.

6-(4-((8-methoxyquinolin-4-yl)amino)butyl)picolinaldehyde oxime 37

37

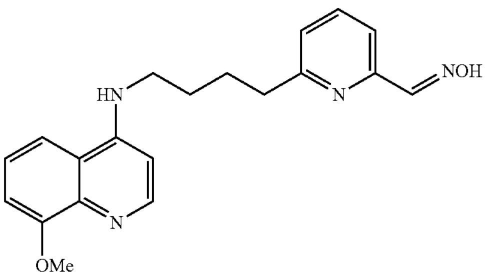

To a degassed suspension of 6-(4-((8-methoxyquinolin-4-yl)amino)but-1-yn-1-yl)picolinaldehyde oxime 36 (110 mg, 0.3 mmol) in anhydrous methanol (10 mL), was added Pearlman's catalyst (9 mg, 0.1 mmol). The reaction vessel was evacuated and flushed with hydrogen gas five times. The black reaction mixture was stirred for 18 h at rt. The catalyst was removed by filtration through Celite and the solvent was removed in vacuo to afford the title compound 37 (40 mg, 0.1 mmol, 36%) as a cream solid: mp=107-108° C.; IR (neat) $v_{max}$ 2927, 1617, 1581, 980 $cm^{-1}$; $^1H$ NMR (400 MHz, MeOD-$d_6$) δ 8.29 (d, J=5.6 Hz, 1H, NCHCH), 8.08 (s, 1H, CHNOH), 7.71-7.57 (m, 3H, ArH), 7.34 (t, J=8.2 Hz, 1H, NCC(OMe)CHCHCH), 7.24-7.19 (m, 1H, NCC(OMe)CHCHCH), 7.08 (d, J=7.8 Hz, 1H, NCCHCHCH), 6.48 (d, J=5.6 Hz, NCHCH), 3.98 (s, 3H, OMe), 3.36 (t, J=7.1 Hz, 2H, $NHCH_2CH_2CH_2CH_2$), 2.83 (t, J=7.1 Hz, 2H, $NHCH_2CH_2CH_2CH_2$), 1.94-1.66 (m, 4H, $NHCH_2CH_2CH_2CH_2$); $^{13}C$ NMR (100 MHz, MeOD-$d_6$) δ 163.2, 156.2, 153.3, 152.7, 150.0, 149.6, 140.4, 138.8, 125.8, 124.5, 121.1, 119.3, 113.8, 109.3, 99.9, 56.4, 43.8, 38.4, 28.9, 28.7; HRMS $(ESI)^+$ m/z calcd for $C_{20}H_{23}N_4O_2^+$ 351.1816, found 351.1817.

REFERENCES

2. Kiplin Guy, R. et al. *Bioorg. Med. Chem. Lett.* 2005, 15, 1015-1018.
3. Lauer et al. *J. Am. Chem. Soc.*, 1946, 68, 1268.
4. Pulley et al. *J. Org. Chem.* 2007, 72, 2232-2235.
5. Musonda, C. C.; Little, S.; Yardley, V.; Chibale, K. *Bioorg. Med. Chem. Lett.* 2007, 17, 4733-4736

Synthesis of 6-(3-(4-benzylpiperazin-1-yl)propyl) picolinaldehyde oxime 43

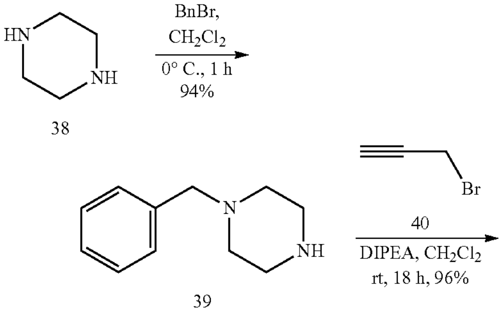

-continued

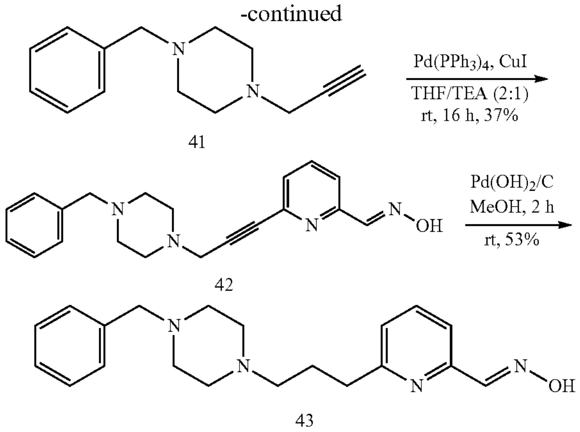

N-Benzylpiperazine 39

39

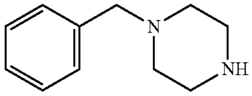

Following the procedure from Bozell and Biannic.[1] for the synthesis of benzylpiperazine; To a solution of piperazine 38 (12.9 g, 149.0 mmol) in anhydrous $CH_2Cl_2$ (100 mL) was added dropwise at 0° C., benzyl bromide (3.56 mL, 29.8 mmol). The reaction was stirred for 1 h at 0° C. The pale yellow solution was washed with a saturated aqueous solution of $NaHCO_3$ (2×50 mL), dried ($Na_2SO_4$), filtered and concentrated in vacuo. Absolute EtOH was added and a white precipitate was filtered from the solution. The solution was concentrated in vacuo to afford the title compound 39 (24.8 g, 141.0 mmol, 94%) as a viscous yellow oil. IR (neat) $v_{max}$ 3289, 2990, 2960, 2120, 1120 $cm^{-1}$; $^1H$NMR (400 MHz, $CDCl_3$) δ (ppm) 7.36-7.28 (m, 5H, ArH), 3.50 (s, 2H, $CH_2Ph$), 2.90 (t, J=4.9 Hz, 4H, $CH_2N(Bn)CH_2$), 2.55-2.30 (m, 5H, $CH_2NHCH_2$); $^{13}C$ NMR (101 MHz, $CDCl_3$) δ (ppm) 138.1, 129.2, 128.2, 127.0, 63.7, 54.5, 46.1.

1-Benzyl-4-propargyl piperazine 41

41

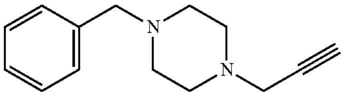

Following a procedure from Corey, M.[2] for the propargyl substitution of piperazines; To a solution of N-benzylpiperazine 39 (1.75 g, 9.93 mmol), propargyl bromide 40 (80% in toluene) (1.28 mL, 14.9 mmol) and DIPEA (3.28 mL, 19.9 mmol) in $CH_2Cl_2$ (50 mL) was stirred for 18 h at rt. $H_2O$ (30 mL) was added and the aqueous phase was separated and extracted (3×20 mL). The combined organic layers were washed (brine, 30 mL), dried ($Na_2SO_4$), filtered and concentrated in vacuo. Chromatography on silica gel (50% EtOAc in hexanes) gave the title compound 41 (2.04 g, 9.5 mmol, 96%) as an orange oil. IR (neat) $v_{max}$ 3290, 3026, 2933, 2807, 2117, 697 $cm^{-1}$; $^{1}$HNMR (400 MHz, $CDCl_3$) δ (ppm) 7.37-7.28 (m, 5H, ArH), 3.56 (s, 2H, $PhCH_2$), 3.30 (d, J=2.5 Hz, 2H, $NCH_2CCH$), 2.73-2.44 (m, 8H, $PizCH_2$), 2.25 (t, J=2.5 Hz, 1H, $NCH_2CCH$); $^{13}$CNMR (101 MHz, $CDCl_3$) δ (ppm) 129.5, 129.3, 128.3, 127.2, 78.9, 73.20, 62.8, 52.8, 51.7, 46.8; HRMS $(ESI)^+$ m/z for $C_xH_xN_x^+$ calculated 215.1543, found 215.1542.

6-(3-(4-benzylpiperazin-1-yl)prop-1-yn-1-yl)picolinaldehyde oxime 42

42

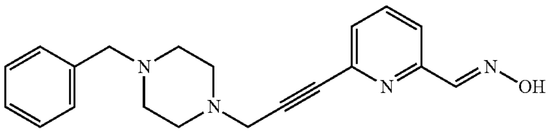

To a degassed solution of 1-benzyl-4-propargyl piperazine 41 (1.30 g, 6.1 mmol) in anhydrous THF/$Et_3N$ (7 mL/3 mL) was added $Pd(PPh_3)_4$ (0.70 g, 0.6 mmol) and CuI (0.23 g, 1.2 mmol). To the resulting orange reaction mixture was added dropwise a degassed solution of 6-bromopicolinaldehyde oxime 2 (1.34 g, 6.7 mmol) in anhydrous THF (20 mL). The brown solution was stirred for 18 h at rt. The reaction was concentrated in vacuo. Chromatography on silica gel (EtOAc) afforded the title compound 42 (750 mg, 2.2 mmol, 37%) as a cream solid: mp=143-145° C.; IR (neat) $v_{max}$ 3150, 3048, 2944, 2808, 2364, 734 $cm^{-1}$; $^{1}$HNMR (400 MHz, $CDCl_3$) δ (ppm) 12.17 (s, 1H, NOH), 7.99 (s, 1H, CHNOH), 7.71 (dd, J=8.0, 1.0 Hz, 1H, NCCHCHCH), 7.53 (t, J=8.0 Hz, 1H, NCCHCHCH), 7.43-7.20 (m, 6H, ArH), 3.70 (s, 2H, $NCH_2CC$), 3.63 (s, 2H, $PhCH_2$), 3.08-2.36 (m, 8H, $PizCH_2$); $^{13}$C NMR (101 MHz, $CDCl_3$) δ (ppm) 152.7, 149.0, 142.2, 136.4, 136.3, 129.9, 128.4, 127.6, 127.1, 119.1, 85.3, 84.3, 63.2, 52.9, 50.5, 47.2; HRMS (ESI)+m/z for $C_{20}H_{23}N_4O^+$ calculated 335.1866, found 335.1863.

6-(3-(4-benzylpiperazin-1-yl)propyl)picolinaldehyde oxime 43

43

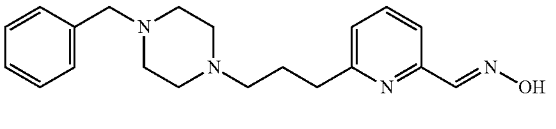

To a degassed suspension of 6-(3-(4-benzylpiperazin-1-yl)prop-1-yn-1-yl)picolinaldehyde oxime 42 (200 mg, 0.6 mmol) in anhydrous methanol (10 mL), was added Pearlman's catalyst (44 mg, 0.3 mmol). The reaction vessel was evacuated and flushed with hydrogen gas five times. The black reaction mixture was stirred for 2 h at rt. The catalyst was removed by filtration through Celite and the solvent was removed in vacuo. Chromatography on silica gel ($CH_2Cl_2$ to 10% MeOH in $CH_2Cl_2$) afforded the title compound 43 as a pale yellow oil (53%). IR (neat) $v_{max}$ 3162, 3057, 2939, 2816, 808 $cm^{-1}$; $^{1}$HNMR (400 MHz, $CDCl_3$) δ (ppm) 8.19 (s, 1H, CHNOH), 7.58-7.51 (m, 2H, ArH), 7.36-7.27 (m, 5H, ArH), 7.10 (dd, J=6.5, 2.2 Hz, 1H, NCCHCHCH), 3.55

(s, 2H, $PhCH_2$), 2.82 (t, J=7.8 Hz, 1H, $NCH_2CH_2CH_2$), 2.72-2.35 (m, 10H, $PizCH_2$, $NCH_2CH_2CH_2$), 2.02 (quin, J=7.8 Hz, $NCH_2CH_2CH_2$); $^{13}$C NMR (101 MHz, $CDCl_3$) δ (ppm) 161.3, 151.8, 150.3, 137.6, 136.6, 129.4, 128.3, 127.2, 122.8, 118.0, 62.9, 57.7, 25.8, 25.5, 35.8, 26.3; HRMS $(ESI)^+$ m/z for $C_{20}H_{27}N_4O^+$ calculated 339.2179, found 339.2176.

REFERENCES

1. Bozell. J. J. et al. *Org. Lett.* 2013, 15, 2730-2733.
2. Corey, M., et al. WO2017/184996 A1 (2017).

Synthesis of 6-(3-(4-benzylpiperazin-1-yl)propyl) picolinaldehyde oxime 48

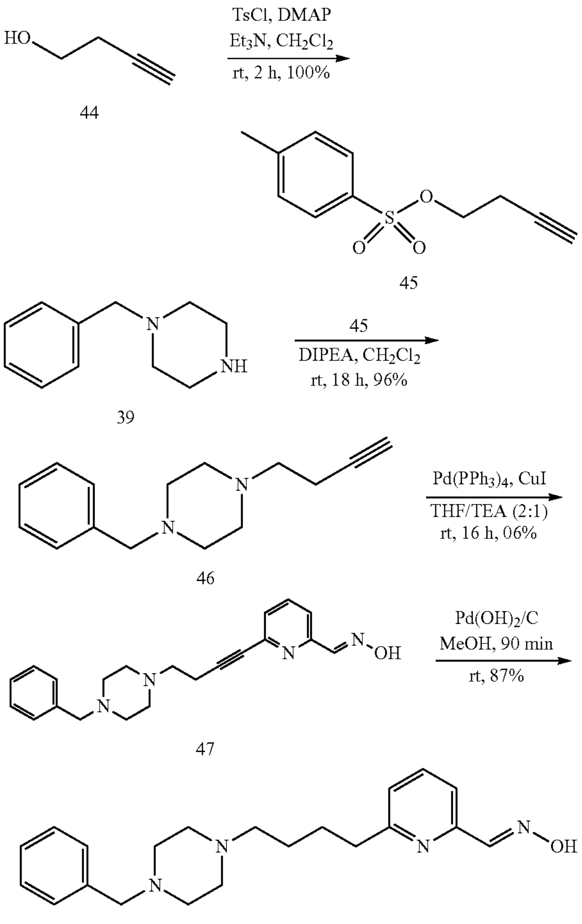

44

45

39

46

47

48

3-Butynyl p-toluenesulfonate 45

45

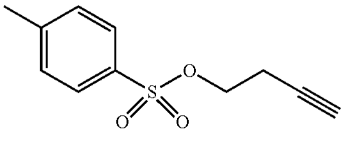

Following a procedure from Winssinger et al.[1] for the formation of p-tolunesulfonyl protected alcohols; To a solution of 3-butyn-1-ol 44 (3.00 g, 42.8 mmol), DMAP (522 mg, 4.3 mmol) and $Et_3N$ (55.6 mL, 7.70 mL mmol) in $CH_2Cl_2$ (15 mL) at 0° C. was added dropwise a solution of TsCl (8.98 g, 47.1 mmol). The yellow reaction solution was allowed to warm to rt and stirred for 2 h. $H_2O$ (30 mL) was added and the reaction was stirred for 20 min at rt. The organic layer was separated and the aqueous layer was extracted ($CH_2Cl_2$, 5×40 mL). The combined extracts were dried ($Na_2SO_4$), filtered and concentrated in vacuo. This afforded the title compound 45 (9.60 g, 42.8 mmol, 100%) as a red/brown oil. IR (neat) $v_{max}$ 3433, 3045, 2958, 2248, 1577, 788 $cm^{-1}$; $^1$HNMR (400 MHz, $CDCl_3$) δ (ppm) 7.81 (d, J=8.3 Hz, 2H, ArH), 7.36 (d, J=8.3 Hz, 2H, ArH), 4.11 (t, J=7.1 Hz, 2H, $TsOCH_2CH_2CCH$), 2.56 (td, J=7.1, 2.7 Hz, 2H, $TsOCH_2$ $TsOCH_2CH_2CCH$), 2.46 (s, 3H, $PhCH_3$), 1.98 (t, J=2.7 Hz, 1H, $TsOCH_2CH_2CCH$); $^{13}$CNMR (101 MHz, $CDCl_3$) δ (ppm) 145.0, 132.8, 129.9, 128.0, 78.3, 70.7, 67.4, 21.6, 19.4.

1-Benzyl-4-(buty-3-yn-1-yl)piperazine 46

46

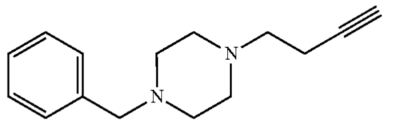

Following a procedure from Guarna et al.[2] for the formation of alkylated piperazines; To a solution of 3-butynyl p-tolunesulfonate 45 (2.30 mL, 10.3 mmol) in DMF (60 mL) was added $Na_2CO_3$ (1.20 g, 11.3 mmol) and N-benzylpiperazine 39 (2.00 g, 11.3 mmol). The orange solution was stirred overnight at 80° C. The reaction mixture was quenched with $H_2O$ (10 mL) and ether (10 mL) was added. The organic layer was separated and washed with $H_2O$ (5×10 mL), brine (10 mL) and dried ($Na_2SO_4$), filtered and concentrated in vacuo. Chromatography on silica gel (100% $CH_2Cl_2$ to 10% MeOH in $CH_2Cl_2$) afforded the title compound 46 (1.70 g, 7.4 mmol, 72%) as an orange oil. IR (neat) $v_{max}$ 3291, 3026, 2939, 2807, 2119, 1676, 697 $cm^{-1}$; $^1$HNMR (400 MHz, $CDCl_3$) δ (ppm) 7.35-7.28 (m, 5H, ArH), 3.52 (s, 2H, $PhCH_2$), 2.61 (t, J=7.6 Hz, 2H, $NCH_2CH_2CCH$), 2.58-2.42 (m, 8H, $PizCH_2$), 2.41-2.34 (m, 2H, $NCH_2CH_2CCH$), 1.97 (t, J=2.7 Hz, 1H, $NCH_2CH_2CCH$); $^{13}$CNMR (101 MHz, $CDCl_3$) δ (ppm) 138.1, 129.2, 128.2, 127.0, 82.8, 69.0, 63.0, 57.0, 52.9, 52.8, 16.8; HRMS (ESI)$^+$ m/z for $C_xH_xN_x^+$ calculated 229.1699, found 229.1695.

6-(4-(4-benzylpiperazin-1-yl)but-1-yn-1-yl)picolinaldehyde oxime 47

47

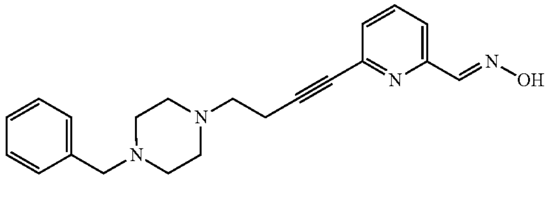

To a degassed solution of 1-benzyl-4-(buty-3-yn-1-yl) piperazine 46 (1.55 g, 6.8 mmol) in anhydrous THF/$Et_3N$ (7 mL/3 mL) was added $Pd(PPh_3)_4$ (1.16 g, 0.7 mmol) and CuI (0.19 g, 1.4 mmol). To the resulting orange reaction mixture was added dropwise a degassed solution of 6-bromopicolinaldehyde oxime 2 (1.50 g, 7.47 mmol) in anhydrous THF (20 mL). The brown solution was stirred for 18 h at rt. The reaction was concentrated in vacuo. Chromatography on silica gel (50% EtOAc in hexanes to EtOAc) afforded the title compound 47 (150 mg, 0.4 mmol, 6%) as a cream solid. mp=134-136° C.; IR (neat) $v_{max}$ 3161, 3060, 2954, 2808, 2231, 740 $cm^{-1}$; $^1$HNMR (400 MHz, $CDCl_3$) δ (ppm) 11.48 (s, 1H, NOH), 8.20 (s, 1H, CHNOH), 7.76 (dd, J=8.0, 1.0 Hz, 1H, NCCHCHCH), 7.59 (t, J=8.0 Hz, 1H, NCCHCHCH), 7.35-7.27 (m, 6H, ArH), 3.56 (s, 2H, $PhCH_2$), 2.82-2.41 (m, 12H, $PizCH_2$, $NCH_2CH_2CC$); $^{13}$C NMR (101 MHz, $CDCl_3$) δ (ppm) 152.9, 149.7, 143.1, 137.4, 136.5, 129.5, 128.3, 127.3, 126.7, 119.1, 89.1, 80.8, 63.0, 56.6, 52.6, 52.5, 17.4; HRMS (ESI)$^+$ m/z for $C_{21}H_{25}N_4O^+$ calculated 349.2023, found 349.2018.

REFERENCES

1. Winssinger et al. *Chem. Comms.* 2010, 46, 5476-5478.
2. Guarna et al. *J. Med. Chem.* 2010, 53, 7119-7128.

6-(4-(4-benzylpiperazin-1-yl)butyl)picolinaldehyde oxime 48

48

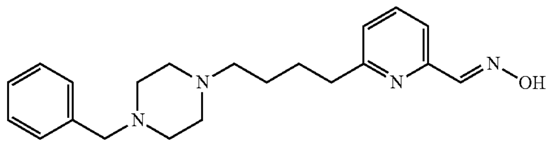

To a degassed suspension of 6-(4-(4-benzylpiperazin-1-yl)but-1-yn-1-yl)picolinaldehyde oxime 47 (60 mg, 0.2 mmol) in anhydrous methanol (5 mL), was added palladium (10% on carbon, 4 mg, 0.04 mmol). The reaction vessel was evacuated and flushed with hydrogen gas five times. The black reaction mixture was stirred for 1.5 h at rt. The catalyst was removed by filtration through Celite and the solvent was removed in vacuo, to afford the title compound 48 (53 mg, 0.2 mmol, 87%) as a yellow oil. IR (neat) $v_{max}$ 3181, 3060, 2938, 2818, 791 $cm^{-1}$, $^1$HNMR (400 MHz, $CDCl_3$) δ (ppm) 8.18 (s, 1H, CHNOH), 7.62-7.50 (m, 2H, ArH), 7.34-7.29 (m, 5H, ArH), 7.11 (dd, J=7.3, 1.4 Hz, 1H, NCCHCHCH), 5.31 (s, 2H, $PhCH_2$), 2.82 (t, J=7.3 Hz, 2H, $NCH_2CH_2CH_2CH_2$), 2.59-2.31 (m, 10H, $PizCH_2$, $NCH_2CH_2CH_2CH_2$), 1.76 (quin, J=7.3 Hz, $NCH_2CH_2CH_2CH_2$), 1.58 (br s, 2H, $NCH_2CH_2CH_2CH_2$); $^{13}$C NMR (101 MHz, $CDCl_3$) δ (ppm) 161.9, 151.5, 150.6, 136.7, 136.6, 129.3, 128.2, 127.1, 122.9, 118.1, 63.0, 58.4, 53.0, 52.7, 37.9, 27.6, 26.1; HRMS (ESI)$^+$ m/z for $C_{20}H_{27}N_4O^+$ calculated 353.2336, found 353.2332.

Synthesis of 6-(4-(3,7-dimethyl-2,6-dioxo-2,3,6,7-tetrahydro-1H-Purin-1-yl)but-1-yn-1-yl)picolinaldehyde oxime 51

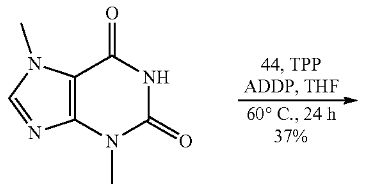

49

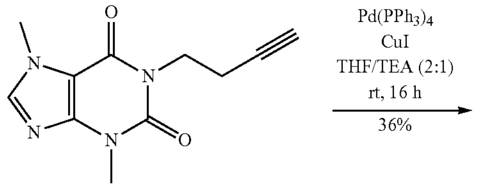

50

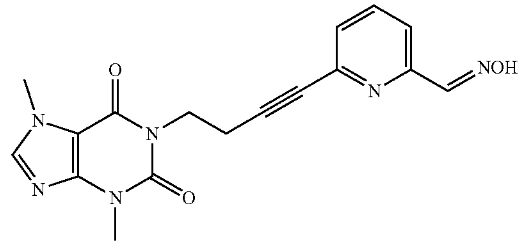

51

1-(But-3-yn-1-yl)-3,7-dimethyl-dihydro-1H-purine-2,6-dione 50

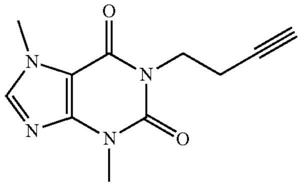

Following an adapted procedure from Itô et al.[1] for the synthesis of substituted amines by Mitsunobu reaction; To a solution of 3-butyn-1-ol 44 (0.10 mL, 1.4 mmol), theobromine 49 (500 mg, 2.8 mmol) and triphenyl phosphine (728 mg, 2.8 mmol) in THF (15 mL) at rt was added ADDP (700 mg, 2.8 mmol). The yellow reaction was heated to 60° C. for 24 h. The cream-coloured reaction solution was diluted ($H_2O$, 50 mL), and the aqueous solution was extracted (EtOAc, 3×20 mL). The combined organic layers were dried ($MgSO_4$), filtered and concentrated in vacuo. The white residue was purified by chromatography on silica gel (EtOAc) to afford 1-(but-3-yn-1-yl)-3,7-dimethyl-dihydro-1H-purine-2,6-dione 50 (120 mg, 0.5 mmol, 37%) as a white solid: mp=192-193° C.; IR (neat) $v_{max}$ 3228, 3107, 2951, 1697, 1651 $cm^{-1}$; $^1$HNMR (400 MHz, DMSO-$d_6$) δ (ppm) 8.00 (s, 1H, NCHN), 3.99 (t, J=7.6 Hz, 2H, $NCH_2CH_2CCH$), 3.87 (s, 3H, $NCHN(CH_3)$), 3.40 (s, 3H, $NCON(CH_3)$), 2.84 (t, J=2.7 Hz, 1H, $NCH_2CH_2CCH$), 2.45 (td, J=7.6, 2.7 Hz, 1H, $NCH_2CH_2CCH$); $^{13}$C NMR (101 MHz, DMSO-$d_6$) δ (ppm) 154.6, 151.1, 148.7, 143.5, 107.0, 81.5, 73.0, 40.6, 33.6, 29.8, 17.3; HRMS (ESI)$^+$ m/z for $C_{11}H_{13}N_4O_2^+$ calculated 233.1033, found 233.1035 and m/z for $C_{11}H_{12}N_4NaO_2^+$ calculated 255.0852, found 255.0857.

6-(4-(3,7-dimethyl-2,6-dioxo-2,3,6,7-tetrahydro-1H-purin-1-yl)but-1-yn-1-yl)picolinaldehyde oxime 51

51

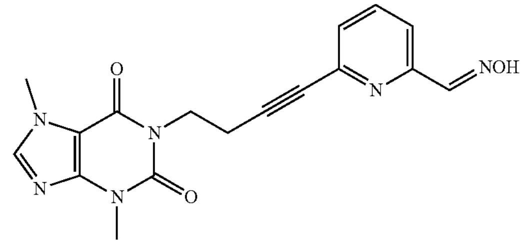

To a degassed solution of 1-(but-3-yn-1-yl) 3,7-dimethyl-dihydro-1H-purine-2,6-dione 50 (200 mg, 0.9 mmol) in anhydrous THF/$Et_3N$ (7 mL/3 mL) was added $Pd(PPh_3)_4$ (99 mg, 0.1 mmol) and CuI (33 mg, 0.2 mmol). To the resulting orange reaction mixture was added dropwise a degassed solution of 6-bromopicolinaldehyde oxime 2 (190 mg, 1.0 mmol) in anhydrous THF (10 mL). The brown solution was stirred for 16 h at rt. The reaction was concentrated in vacuo giving an orange solid as the crude product. Chromatography on silica gel (EtOAc to 10% MeOH in EtOAc) afforded the title compound 51 (111 mg, 0.3 mmol, 36%) as a colourless: mp=210-211° C.; IR (neat) $v_{max}$ 3178, 3087, 2872, 2230, 1700, 1647, 759 $cm^{-1}$, $^1$H NMR (400 MHz, DMSO-$d_6$) δ 11.75 (s, 1H, CHNOH), 8.03 (s, 1H, CHNOH), 8.00 (s, 1H, NCHN), 7.79 (t, J=8.1 Hz, 1H, NCCHCHCH), 7.73 (dd, J=8.1, 1.0 Hz, 1H, NCCHCHCH), 7.39 (dd, J=8.1, 1.0 Hz, 1H, NCCHCHCH), 4.12 (t, J=7.5 Hz, 2H, $NHCH_2CH_2$), 3.88 (s, 3H, $NCHN(CH_3)$, 3.42 (s, 3H, NCON (CH3), 2.75 (t, J=7.5 Hz, 2H, $NHCH_2CH_2$); $^{13}$C NMR (100 MHz, DMSO-$d_6$) δ 154.2, 152.4, 150.7, 148.4, 148.3, 143.1, 142.3, 137.3, 126.8, 119.0, 118.9, 106.5, 87.4, 81.3, 33.2, 29.4, 17.7; HRMS (ESI)$^+$ m/z for $C_{17}H_{17}N_6O_3^+$ calculated 353.1357, found 353.1358.

REFERENCES
1. Itô, S. et al. *Tet. Letts.,* 1993, 34, 1639-1642.
µII—Synthesis of Bifunctional Neca Analogs
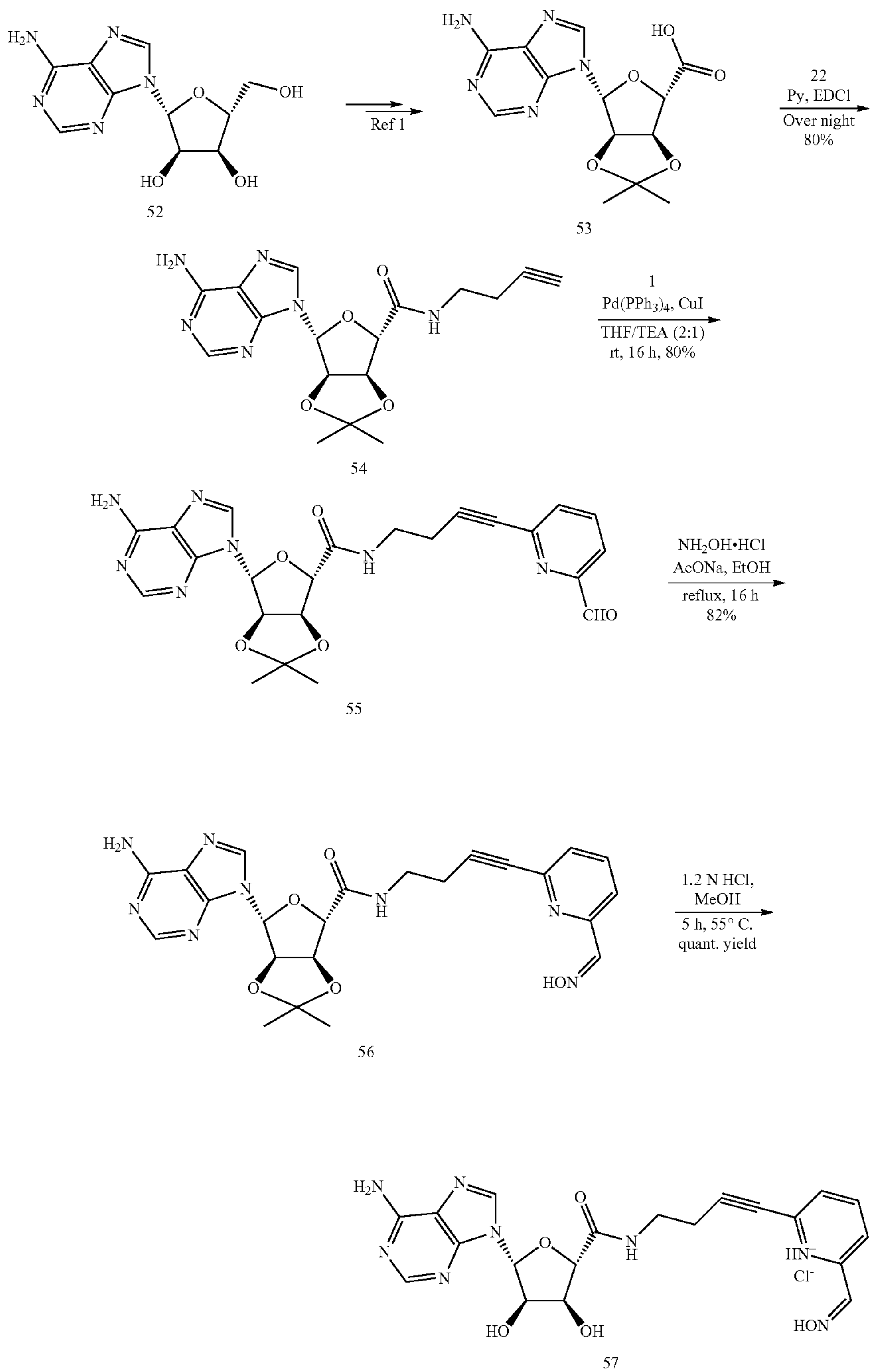
52
53
54
55
56
57

(3aS,4S,6R,6aR)-6-(6-amino-9H-purin-9-yl)-N-(but-3-yn-1-yl)-2,2-dimethyltetrahydrofuro[3,4-d][1,3]dioxole-4-carboxamide 54

54

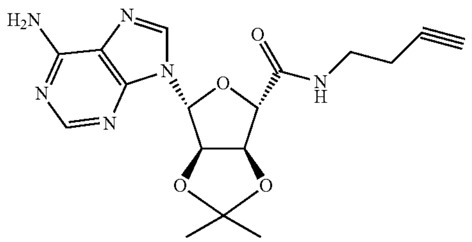

The synthesis of (3aS,4S,6R,6aR)-6-(6-amino-9H-purin-9-yl)-2,2-dimethyltetrahydrofuro[3,4-d][1,3]dioxole-4-carboxylic acid 53 was achieved by using an adapted procedure from Debnath, J. et al.[1].

To a stirred solution of acid 53 (500 mg, 1.56 mmol, 1 equiv) in dry pyridine (15 mL), 1-amino-3-butyne 22 (140 μL, 1.71 mmol, 1.1 equiv), and EDCI (598 mg, 3.12 mmol, 2 equiv) were successively added and the reaction mixture was stirred at room temperature under a nitrogen atmosphere for overnight. After completion, the reaction mixture was directly concentrated under reduced pressure and the residue was purified by column chromatography (EtOAc to EtOAc/MeOH 95:5) to afford the desired amide 54 as light yellow solid (500 mg, 80%). $R_f$ (pure EtOAc) 0.18; IR (neat) $v_{max}$ 3289, 3142, 1672, 1601, 1526, 1206, 1090, 1058, 868, 789, 645, 514 $cm^{-1}$; $^1H$ NMR (400 MHz, $CDCl_3$) δ (ppm) 8.32 (s, 1H), 7.89 (s, 1H), 7.28 (m, 1H), 6.33 (s, 2H), 6.13 (d, J=2.5 Hz, 1H), 5.47 (dd, J=2.1, 6.2 Hz, 1H), 5.39 (dd, J=2.5, 6.2 Hz, 1H), 4.74 (d, J=2.1 Hz, 1H), 3.21 (m, 2H), 2.21 (m, 1H), 2.10 (m, 1H), 1.82 (t, J=2.6 Hz, 1H), 1.63 (s, 3H), 1.40 (s, 3H); $^{13}C$ NMR (100 MHz, $CDCl_3$) δ (ppm) 168.98, 155.86, 153.11, 148.99, 139.82, 120.21, 114.37, 91.70, 86.33, 83.59, 82.88, 80.81, 69.83, 37.49, 26.95, 25.07, 18.85; HRMS ($ESI^+$) m/z calcd for $C_{17}H_{21}N_6O_4^+$373.1575 found 373.1619.

(3aS,4S,6R,6aR)-6-(6-amino-9H-purin-9-yl)-N-(4-(6-formylpyridin-2-yl)but-3-yn-1-yl)-2,2-dimethyltetrahydrofuro[3,4-d][1,3]dioxole-4-carboxamide 55

55

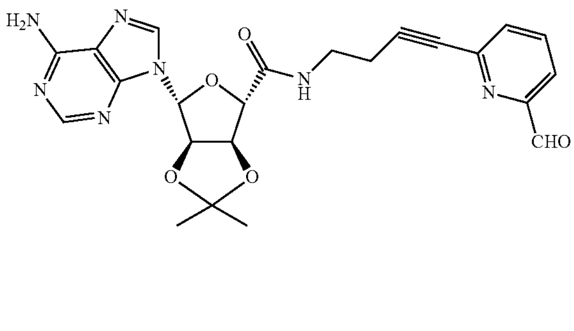

To a degassed solution of methyl 6-bromopicolinaldehyde 1 (275 mg, 1.478 mmol, 1.1 equiv) in THF/$Et_3N$ (10 mL/8 mL), $Pd[PPh_3]_4$ (233 mg, 0.202 mmol, 0.15 equiv) and CuI (77 mg, 0.403 mmol, 0.3 equiv) were added. After degassing the reaction mixture for 5 min at room temperature, a degassed solution of alkyne 54 (500 mg, 1.344 mmol, 1 equiv) in THF (10 mL) was added dropwise and the reaction mixture was stirred at room temperature for 16 h. After completion, the reaction mixture was concentrated under reduced pressure and the residue was purified by column chromatography (pure EtOAc to EtOAc/MeOH 9:1) to afford the desired coupled picolinaldehyde 55 as thick syrup (510 mg, 80%). IR (neat) $v_{max}$ 3318, 1638, 1582, 1452, 1209, 1078, 868, 797, 646, 509 $cm^{-1}$; $^1H$ NMR (400 MHz, $CDCl_3$) δ (ppm) 9.90 (s, 1H), 8.24 (s, 1H), 7.85-7.65 (m, 3H), 7.38 (m, 1H), 6.40 (s, 1H), 6.02 (s, 1H), 5.33 (s, 2H), 4.70 (s, 1H), 3.35 (m, 2H), 2.60-2.32 (m, 2H), 1.57 (s, 3H), 1.31 (s, 3H); $^{13}C$ NMR (100 MHz, $CDCl_3$) δ (ppm) 192.88, 169.13, 155.67, 153.12, 152.63, 148.97, 143.63, 139.87, 137.20, 130.85, 120.19, 114.62, 91.94, 88.87, 85.74, 83.55, 82.54, 80.66, 37.41, 27.09, 25.11, 20.08; HRMS ($ESI^+$) m/z calcd for $C_{23}H_{24}N_7O_5^+$ 478.1806 found 478.1833.

(3aS,4S,6R,6aR)-6-(6-amino-9H-purin-9-yl)-N-(4-(6-(hydroxyimino)methyl)pyridin-2-yl)but-3-yn-1-yl)-2,2-dimethyltetrahydrofuro[3,4-d][1,3]dioxole-4-carboxamide 56

56

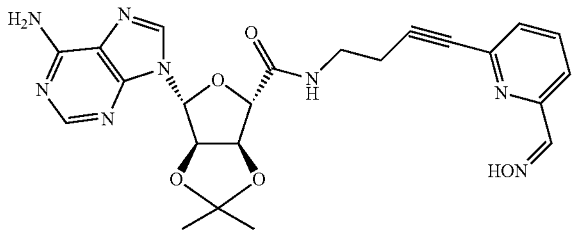

A solution of picolinaldehyde 55 (80 mg, 0.168 mmol, 1 equiv), hydroxylamine hydrochloride (23 mg, 0.336 mmol, 2 equiv), and $CH_3CO_2Na$ (41 mg, 0.503 mmol, 3 equiv) in dry ethanol (5 mL) was stirred at reflux during 16 h. After concentration under reduced pressure, the crude product was washed with $CH_2Cl_2$ (5*10 mL) to remove all the impurities. The existing compound in the round bottom flask was picolinaldehyde oxime 56, which was dried in high vacuo (82 mg, quant. yield) and confirmed by $^1H$ NMR. $R_f$ (EtOAc); IR (neat) $v_{max}$ 3186, 2925, 1643, 1579, 1207, 1089, 980, 867, 797, 726, 649, 509 $cm^{-1}$; $^1H$ NMR (400 MHz, $CDCl_3$) δ (ppm) 8.20 (s, 1H), 8.11 (s, 1H), 7.92 (m, 2H), 7.46 (m, 2H), 7.02 (m, 3H), 6.05 (d, J=2.7 Hz, 1H), 5.35 (dd, J=2.0, 6.2 Hz, 1H), 5.29 (dd, J=2.7, 6.2 Hz, 1H), 4.74 (d, J=2.0 Hz, 1H), 3.41 (m, 2H), 2.57-2.33 (m, 2H), 1.59 (s, 3H), 1.433 (s, 3H); $^{13}C$ NMR (100 MHz, $CDCl_3$) δ (ppm) 169.14, 155.54, 152.89, 152.05, 149.16, 148.60, 142.61, 139.82, 136.66, 126.72, 119.58, 119.47, 114.74, 91.86, 88.15, 85.78, 83.45, 82.68, 81.13, 37.45, 27.11, 25.14, 20.21; HRMS ($ESI^+$) m/z calcd for $C_{23}H_{25}N_8O_5^+$ 493.1901 found 493.1942. (2S,3S,4R,5R)-5-(6-amino-9H-purin-9-yl)-3,4-dihydroxy-N-(4-(6-(hydroxyimino) methyl) pyridin-2-yl)but-3-yn-1-yl)tetrahydrofuran-2-carboxamide 57:

57

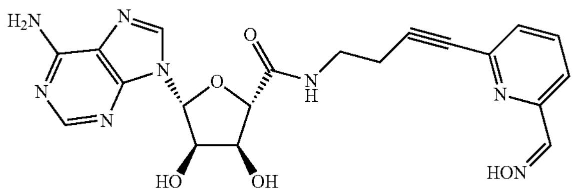

To a stirred solution of oxime 56 (30 mg, 0.061 mmol, 1 equiv) in dry MeOH (5 mL), 1.2 N HCl (185 μL, 0.610 mmol, 10 equiv) was added and the reaction mixture was stirred at 55° C. for 5 h. After completion, the reaction mixture was directly concentrated under reduced pressure and the residue was purified by reverse phase column chromatography ($MeOH/H_2O$ 1:4) to afford the salt 57 as a white solid in quantitative yield. IR (neat) $\nu_{max}$ 3192, 2927, 1644, 1580, 1448, 1305, 1254, 1045, 989, 808, 726, 642, 533 $cm^{-1}$; $^1H$ NMR (400 MHz, $CD_3OD$) δ (ppm) 8.26 (s, 1H), 8.25 (s, 1H), 7.90 (s, 1H), 7.68 (br d, J=7.8 Hz, 1H), 7.0 (t, J=7.8 Hz, 1H), 7.13 (d, J=7.5 Hz, 1H), 6.30 (d, J=7.9 Hz, 1H), 4.85 (s, 1H), 4.54 (s, 1H), 4.39 (br d, J=4.3 Hz, 1H), 3.63 (m, 2H), 2.74 (m, 2H); $^{13}C$ NMR (100 MHz, $CD_3OD$) δ (ppm) 172.76, 157.47, 154.03, 153.96, 150.15, 149.49, 143.97, 142.67, 138.49, 128.24, 121.22, 120.73, 90.84, 89.91, 86.78, 82.11, 75.30, 73.56, 38.93, 21.02; HRMS ($ESI^+$) m/z calcd for $C_{23}H_{25}N_8O_5^+$ 493.1901 found 493.1942.

REFERENCES

1. Debnath, J. et al. *Bioorg. Med. Chem.* 2010, 18, 8257-8263.

III—Synthesis of Bifunctional Pseudo Neca Analog

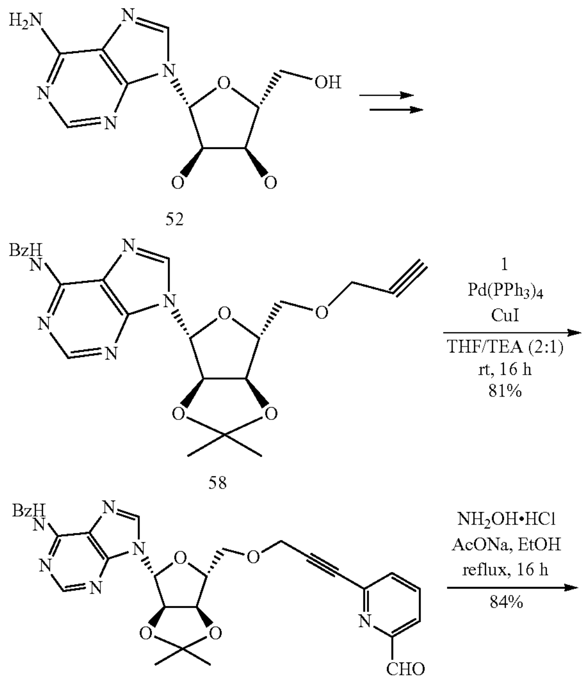

52

58

59

-continued

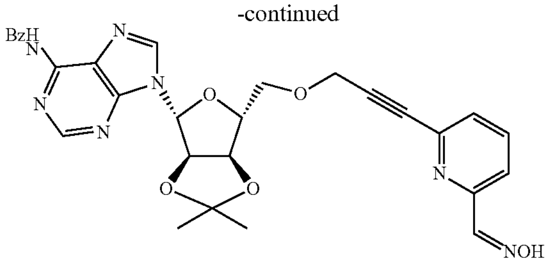

+

60 39%

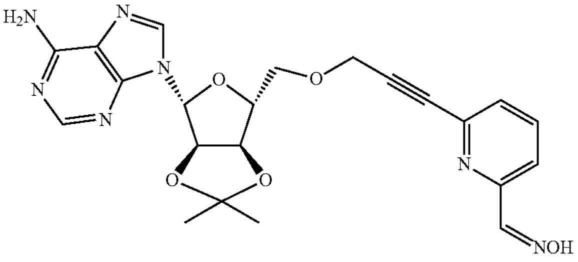

61 45%

N-(9-((3aR,4R,6R,6aR)-6-(((3-(6-formylpyridin-2-yl)prop-2-yn-1-yl)oxy)methyl)-2,2-dimethyltetrahydrofuro[3,4-d][1,3]dioxol-4-yl)-9H-purin-6-yl)benzamide 59

59

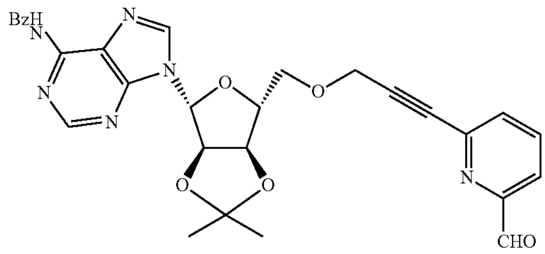

The synthesis of N-(9-((3aR,4R,6R,6aR)-2,2-dimethyl-6-((prop-2-yn-1-yloxy)methyl)-tetrahydrofuro[3,4-d][1,3]dioxol-4-yl)-9H-purin-6-yl)benzamide 58 was achieved by using a known procedure from Silvia, F. et al.[1].

To a degassed solution of 6-bromopicolinaldehyde 1 (91 mg, 0.490 mmol, 1.1 equiv) in $THF/Et_3N$ (3 mL/2 mL), $Pd[PPh_3]_4$ (77 mg, 0.067 mmol, 0.15 equiv) and CuI (25 mg, 0.134 mmol, 0.3 equiv) were added. After degassing the reaction mixture for 5 min at room temperature, a degassed solution of alkyne 58 (200 mg, 0.445 mmol, 1 equiv) in THF (3 mL) was added dropwise and the reaction mixture was stirred at the room temperature for 16 h. After completion, the reaction mixture was concentrated under reduced pressure and the residue was purified by column chromatography (EtOAc/petroleum ether 4:1) to afford the desired coupled picolinaldehyde 59 as a thick syrup (200 mg, 81%). IR (neat) $\nu_{max}$ 2935, 1704, 1609, 1580, 1452, 1248, 1210, 1074, 864, 709, 645, 541 $cm^{-1}$; $^1H$ NMR (400 MHz, $CDCl_3$) δ (ppm) 9.97 (s, 1H), 8.76 (s, 1H), 8.32 (s, 1H), 7.94 (d, J=7.6 Hz, 2H), 7.85-7.77 (m, 2H), 7.63-7.51 (m, 2H), 7.45 (t, J=7.6 Hz, 2H), 6.25 (d, J=2.1 Hz, 2H), 5.32 (dd, J=2.1, 6.2 Hz, 1H), 5.03 (dd, J=2.1, 6.2 Hz, 1H), 4.56 (q, J=2.9 Hz, 1H), 4.37 (s, 2H), 3.89-3.77 (m, 2H), 1.61 (s, 3H), 1.37 (s, 3H); $^{13}C$ NMR (100 MHz, $CDCl_3$) δ (ppm) 192.58, 164.85, 152.75, 152.59, 151.49, 149.28, 142.85, 141.91, 137.53, 13335, 132.81, 131.23, 128.78, 127.81, 123.24, 120.91, 114.32, 91.61, 85.94, 85.47, 85.20, 84.55, 70.32, 59.09, 27.12, 25.28; HRMS ($ESI^+$) m/z calcd for $C_{29}H_{27}N_6O_6^+$ 555.2005 found 555.1987.

N-(9-((3aR,4R,6R,6aR)-6-(((3-(6-(hydroxyimino)methyl)pyridin-2-yl)prop-2-yn-1-yl)oxy)methyl)-2,2-dimethyltetrahydrofuro[3,4-d][1,3]dioxol-4-yl)-9H-purin-6-yl)benzamide 60 and 6-(3-(((3aR,4R,6R,6aR)-6-(6-amino-9H-purin-9-yl)-2,2-dimethyltetrahydrofuro[3,4-d][1,3]dioxol-4-yl)methoxy)prop-1-yn-1-yl)picolinaldehyde oxime 61

60

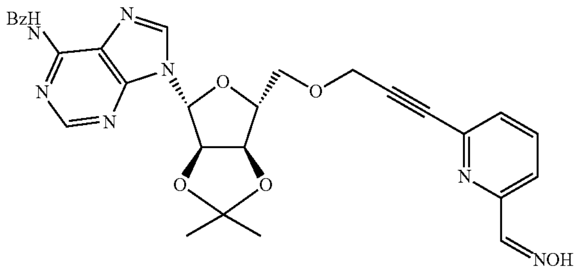

61

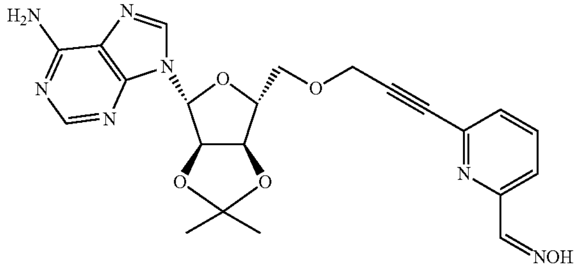

A solution of picolinaldehyde 59 (200 mg, 0.361 mmol, 1 equiv), hydroxylamine hydrochloride (50 mg, 0.722 mmol, 2 equiv), and $CH_3CO_2Na$ (89 mg, 1.083 mmol, 3 equiv) in dry ethanol (10 mL) was stirred at reflux during 16 h. After completion, the reaction mixture was concentrated under reduced pressure and the residue was purified by column chromatography and elution first with DCM to MeOH/DCM (2:98) gave the 60 as a white solid (80 mg, 39%). IR (neat) $v_{max}$ 3196, 2924, 1698, 1610, 1581, 1453, 1246, 1210, 1075, 907, 727, 644, 551 $cm^{-1}$; $^1H$ NMR (400 MHz, $CDCl_3$) δ (ppm) 8.83 (s, 1H), 8.38 (s, 1H), 8.11 (s, 1H), 7.99-7.89 (m, 2H), 7.54-7.27 (m, 6H), 6.27 (d, J=2.3 Hz, 2H), 5.31 (dd, J=2.3, 6.0 Hz, 1H), 5.03 (dd, J=2.3, 6.1 Hz, 1H), 4.48 (br q, J=3.4 Hz, 1H), 4.37, 4.30 (2d, J=16.1 Hz, 2H), 3.88 (dd, J=3.4, 10.3 Hz, 1H), 3.76 (dd, J=4.0, 10.3 Hz, 1H), 1.62 (s, 3H), 1.38 (s, 3H); $^{13}C$ NMR (100 MHz, $CDCl_3$) δ (ppm) 165.11, 152.73, 152.22, 151.35, 149.67, 149.37, 141.87, 136.74, 133.45, 132.69, 128.63, 127.92, 127.22, 122.87, 120.30, 114.28, 91.87, 86.05, 85.03, 84.34, 81.89, 70.23, 59.17, 27.11, 25.26; HRMS ($ESI^+$) m/z calcd for $C_{29}H_{28}N_7O_6^+$ 570.2075 found 570.2096.

Further elution (MeOH/DCM 5:95) afforded 61 as a white solid (75 mg, 45%). IR (neat) $v_{max}$ 3176, 2925, 1639, 1450, 1374, 1207, 1077, 978, 865, 796, 717, 648, 510 $cm^{-1}$; $^1H$ NMR (400 MHz, $CDCl_3$) δ (ppm) 8.30 (s, 1H), 8.21 (s, 1H), 8.15 (s, 1H), 7.64-7.52 (m, 2H), 7.26 (s, 1H), 7.01-6.87 (m, 2H), 6.20 (d, J=1.8 Hz, 2H), 5.35 (m, 1H), 5.03 (m, 1H), 4.57 (m, 1H), 4.35 (m, 2H), 3.88-3.76 (m, 2H), 1.61 (s, 3H), 1.38 (s, 3H); $^{13}C$ NMR (100 MHz, $CDCl_3$) δ (ppm) 155.35, 152.55, 152.47, 149.34, 149.08, 141.96, 139.32, 136.75, 132.82, 127.10, 119.93, 114.13, 91.70, 86.10, 85.72, 84.86, 84.38, 81.88, 70.21, 59.11, 27.07, 25.27; HRMS ($ESI^+$) m/z calcd for $C_{22}H_{24}N_7O_5^+$ 466.1812 found 466.1833.

REFERENCES

1. Silvia, F. et al. *J. Med. Chem.* 2015, 58, 8269-8284

IV—Synthesis of Bifunctional 3-Methoxy Pyridinaldoxime Analogs

Synthesis of 3-methoxy-6-(5-phenylpentyl)picolinaldehyde oxime 65

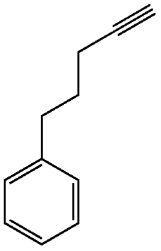

3

+

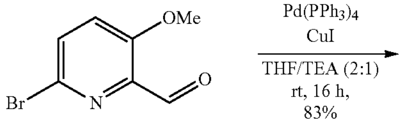

62

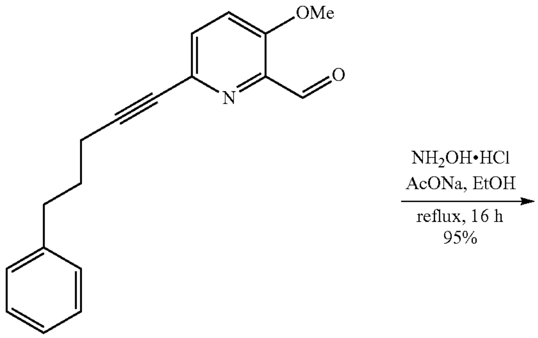

63

-continued

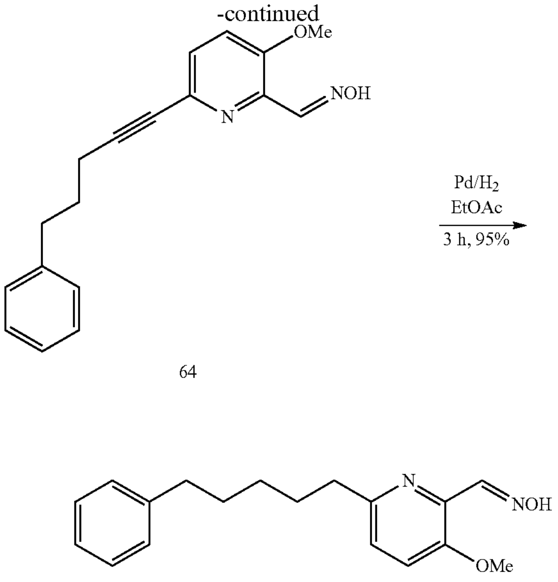

64

65

3-methoxy-6-(5-phenylpent-1-yn-1-yl)picolinaldehyde 63

63

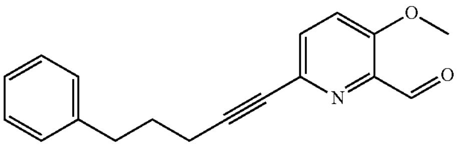

To a degassed solution of commercial 6-bromo-3-methoxypicolinaldehyde 62 (75 mg, 0.347 mmol, 1.0 equiv) in THF/$Et_3N$ (4 mL/2 mL), $Pd[PPh_3]_4$ (60 mg, 0.052 mmol, 0.15 equiv) and CuI (20 mg, 0.104 mmol, 0.3 equiv) were added. After degassing the reaction mixture for 5 min at room temperature, alkyne 3 (50 mg, 0.347 mmol, 1 equiv) was added dropwise and the reaction mixture was stirred at room temperature for 16 h. After completion (monitored by TLC), the reaction mixture was concentrated under reduced pressure and the residue was purified by column chromatography (EtOAc/PE 1:4) to afford the desired coupled methoxy piconaldehyde 63 as a colourless liquid (80 mg, 83%). $R_f$(30% EtOAc+PE) 0.25; IR (neat) $v_{max}$ 2941, 2230, 1709, 1552, 1466, 1267, 1007, 747, 699, 542 $cm^{-1}$; $^1H$ NMR (400 MHz, $CDCl_3$) δ (ppm) 10.21 (s, 1H, $H_{18}$), 7.52 (d, J=8.8 Hz, 1H, $H_4$), 7.33 (d, J=8.8 Hz, 1H, $H_5$), 7.28-7.13 (m, 5H, $H_{13}$-$H_{17}$), 3.93 (s, 3H, –OMe), 2.74 (t, J=7.5 Hz, 2H, $H_{11}$), 2.39 (t, J=7.1 Hz, 2H, $H_9$), 1.91 (quintet, J=7.1, 7.5 Hz, 2H, $H_{10}$); $^{13}C$ NMR (100 MHz, $CDCl_3$) δ (ppm) 195.52 (C18), 156.25, 141.28, 140.73, 136.02, 132.0, 128.44, 128.32, 125.91, 120.41 (Ar), 90.27 (C7), 79.44 (C8), 56.03 (–OMe), 34.86 (C11), 29.76 (C10), 18.72 (C9); HRMS ($ESI^+$) m/z calcd for $C_{18}H_{18}N_1O_2{}^+$280.1332 found 280.1348.

3-methoxy-6-(5-phenylpent-1-yn-1-yl)picolinaldehyde oxime 64

64

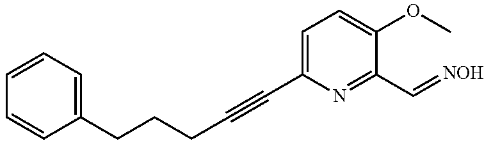

A solution of aldehyde 63 (45 mg, 0.161 mmol, 1 equiv), hydroxylamine hydrochloride (22 mg, 0.322 mmol, 2 equiv), and $CH_3CO_2Na$ (40 mg, 0.483 mmol, 3 equiv) in dry ethanol (3 mL) was stirred at reflux for 16 h. Upon completion (monitored by TLC), the solids were removed by filtration through a short celite pad, the solvent was evaporated under reduced pressure, and the residue was purified by column chromatography (EtOAc/PE 3:7) to afford oxime 64 as a white solid (45 mg, 95%). $R_f$(50% EtOAc+PE) 0.35; IR (neat) $v_{max}$ 3247, 2938, 2234, 1564, 1463, 1263, 975, 828, 745, 698, 649, 487 $cm^{-1}$; *$^1H$ NMR (400 MHz, $CDCl_3$) δ (ppm) 10.42 (br s, 1H, OH), 8.42, 8.10 (2s, 1.2H, $H_{18}$, $H_{18'}$), 7.46-7.19 (m, 7.6H, Ar), 3.94, 3.91 (2s, 3.6H, –OMe), 2.81, 2.80 (2t, J=7.5 Hz, 2.4H, $H_{11}$, $H_{11'}$), 2.47, 2.44 (2t, J=7.1 Hz, 2.4H, $H_9$, $H_{9'}$), 2.02-1.92 (m, 2.4H, $H_{10}$, $H_{10'}$); *$^{13}C$ NMR (100 MHz, $CDCl_3$) δ (ppm) 153.54, 151.66, 147.87, 141.41, 141.17, 140.65, 140.23, 136.37, 135.53, 131.86, 129.18, 128.47, 128.34, 128.29, 127.83, 125.93, 125.84, 119.29, 118.69 (Ar), 90.98, 89.24 (C7), 79.93, 78.76 (C8), 55.93, 55.70 (–OMe), 34.85, 34.76 (C11), 29.86, 29.73 (C10), 18.74, 18.57 (C9) (*1:5 ratio of cis-trans isomers); HRMS ($ESI^+$) m/z calcd for $C_{18}H_{18}N_2NaO_2{}^+$317.1260 found 317.1256.

3-methoxy-6-(5-phenylpentyl)picolinaldehyde oxime 65

65

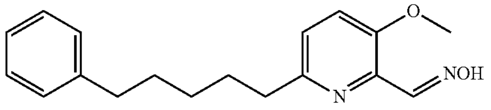

To a degassed solution of methoxy pyridinaldoxime 64 (25 mg, 0.085 mmol, 1 equiv) in dry EtOAc (2 mL), 10% Pd/C (4.5 mg, 0.042 mmol, 0.5 equiv) was added. After flushing with $H_2$ three times, the reaction mixture was stirred at room temperature under $H_2$ (1 atm.) for 3 h. Upon completion (monitored by TLC), the catalyst was removed by filtration through a short column of celite, the solvent was evaporated, and the residue was purified by column chromatography (EtOAc/PE 1:9) to afford oxime 65 as a colourless liquid (24 mg, 95%); $R_f$ (50% EtOAc+PE) 0.40; IR (neat) $v_{max}$ 3253, 2927, 2855, 1570, 1464, 1269, 1127, 975, 746, 698 $cm^{-1}$; $^1H$ NMR (400 MHz, $CDCl_3$) δ (ppm) 8.40, 8.02 (2s, 1.2H, $H_{18}$, $H_{18}$), 7.24-6.96 (m, 9.4H, Ar), 3.79, 3.78 (2s, 3.6H, –OMe), 2.70-2.62 (m, 2.5H, $H_{11}$, $H_{11'}$), 2.55-2.49 (m, 2.5H, $H_7$, $H_{7'}$), 1.68-1.52 (m, 5H, $H_8$, $H_{8'}$, $H_{10}$, $H_{10'}$), 1.35-1.28 (m, 2.5H, $H_9$, $H_{9'}$); *13C NMR (100 MHz, $CDCl_3$) δ (ppm) 154.25, 152.57, 150.87, 150.67, 146.82, 142.71, 142.47, 140.12, 139.24, 137.09, 128.35, 128.21, 128.16, 125.59, 125.51, 125.06, 123.58, 119.91, 119.18

(Ar), 55.82, 55.63 (-OMe), 37.23, 36.25 (C11), 35.78, 35.73 (C7), 31.25, 31.12 (C10), 29.85, 29.67 (C9), 28.90, 28.65 (C8) (*1:4 ratio of cis-trans isomers); HRMS ($ESI^+$) m/z calcd for $C_{18}H_{23}N_2O_2^+$299.1754 found 299.1740.

V—Synthesis of Quinoline Derived Methoxy Pyridinaldoxime Analogs

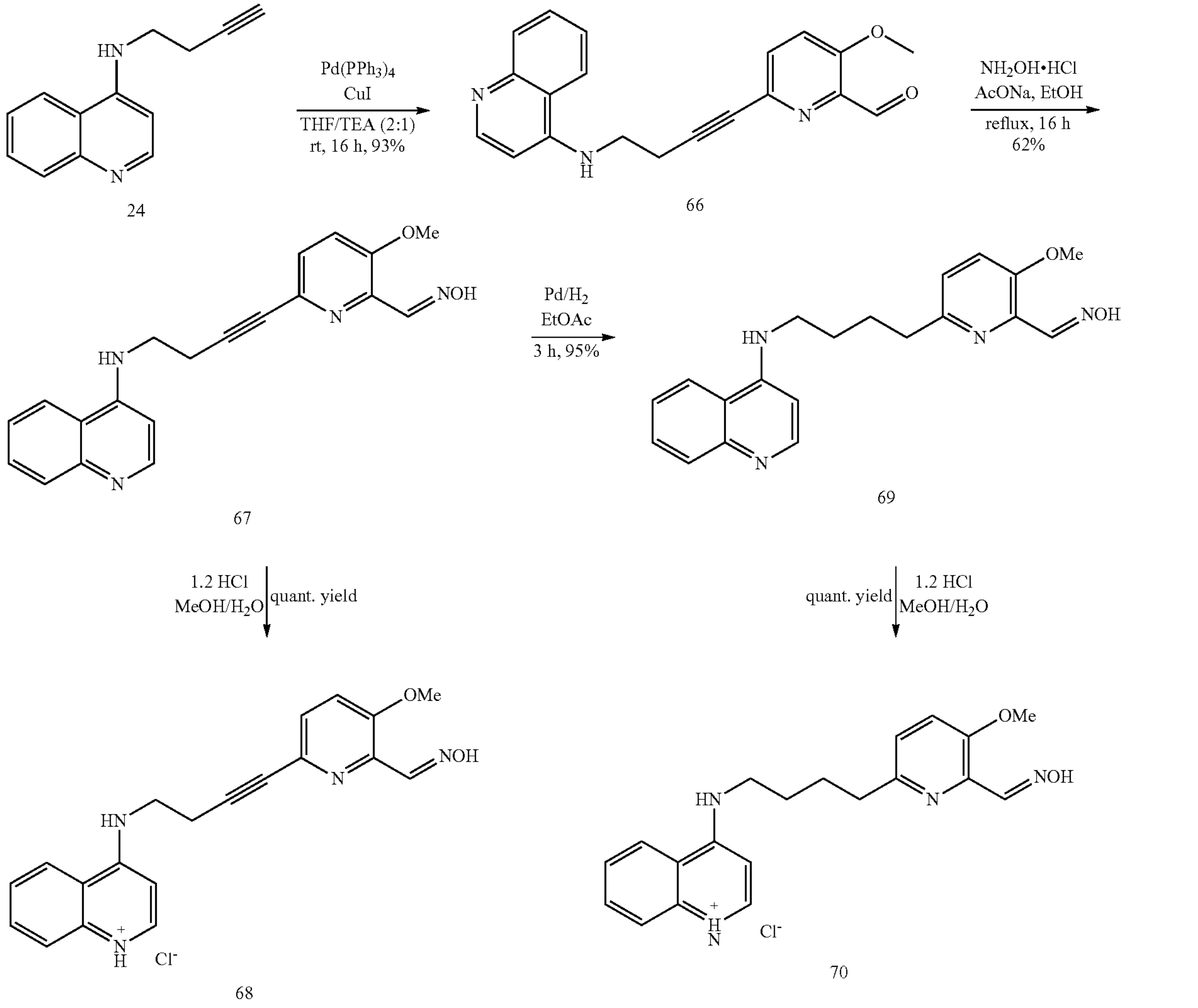

3-methoxy-6-(4-(quinolin-4-ylamino)but-1-yn-1-yl) picolinaldehyde 6

66

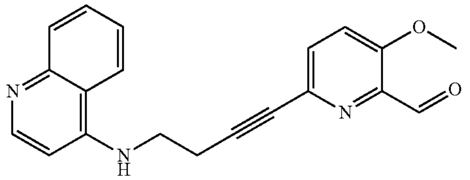

To a degassed solution of commercially available 6-bromo-3-methoxypicolinaldehyde 62 (97 mg, 0.448 mmol, 1.1 equiv) in THF/$Et_3N$ (3 mL/3 mL), $Pd[PPh_3]_4$ (71 mg, 0.061 mmol, 0.15 equiv) and CuI (23 mg, 0.122 mmol, 0.3 equiv) were added. After degassing the reaction mixture for 5 min at room temperature, alkyne 24 (80 mg, 0.408 mmol, 1 equiv) in THF (3 mL) was added dropwise and the reaction mixture was stirred at room temperature for 16 h. After completion (monitored by TLC), the reaction mixture was concentrated under reduced pressure and the residue was purified by column chromatography (MeOH/EtOAc 1:9) to afford the desired coupled methoxy piconaldehyde 66 as a light yellow solid (126 mg, 93%). $R_f$ (30% MeOH+EtOAc) 0.25; IR (neat) $v_{max}$ 3281, 2926, 2233, 1704, 1582, 1434, 1267, 1126, 1009, 763, 694, 521, 494 $cm^{-1}$; $^1H$ NMR (400 MHz, $CDCl_3$) δ (ppm) 10.21 (s, 1H, $H_{18}$), 7.52 (d, J=8.8 Hz, 1H, $H_4$), 7.33 (d, J=8.8 Hz, 1H, $H_5$), 7.28-7.13 (m, 5H, $H_{13}$-$H_{17}$), 3.93 (s, 3H, -OMe), 2.74 (t, J=7.5 Hz, 2H, $H_{11}$), 2.39 (t, J=7.1 Hz, 2H, $H_9$), 1.91 (quintet, J=7.1, 7.5 Hz, 2H, $H_{10}$); $^{13}C$ NMR (100 MHz, $CDCl_3$) δ (ppm) 195.52 (C18), 156.25, 141.28, 140.73, 136.02, 132.0, 128.44, 128.32, 125.91, 120.41 (Ar), 90.27 (C7), 79.44 (C8), 56.03 (-OMe), 34.86 (C11), 29.76 (C10), 18.72 (C9); HRMS ($ESI^+$) m/z calcd for $C_{18}H_{18}N_1O_2^+$280.1332 found 280.1348.

3-methoxy-6-(4-(quinolin-4-ylamino)but-1-yn-1-yl) picolinaldehyde oxime 67

67

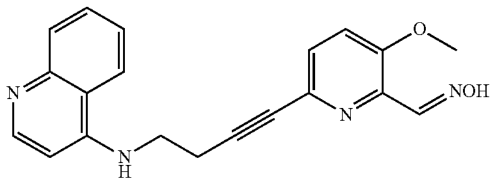

A solution of aldehyde 66 (100 mg, 0.362 mmol, 1 equiv), hydroxylamine hydrochloride (50 mg, 0.724 mmol, 2 equiv), and $CH_3CO_2Na$ (89 mg, 1.086 mmol, 3 equiv) in dry ethanol (5 mL) was stirred at reflux for 16 h. Upon completion (monitored by TLC), the solids were removed by filtration through a short celite pad, the solvent was evaporated under reduced pressure, and the residue was purified by column chromatography (MeOH/EtOAc 1:9) to afford the oxime 67 as a white solid (65 mg, 62%). $R_f$ (30% MeOH+EtOAc) 0.2; IR (neat) $v_{max}$ 3319, 2924, 1897, 1586, 1460, 1242, 1115, 982, 829, 760, 649, 524 $cm^{-1}$; $^1H$ NMR (500 MHz, DMSO-d6) δ (ppm) 11.63 (br s, 1H, OH), 8.41 (d, J=5.2 Hz, 1H, Ar), 8.22 (s, 1H, —C—NOH), 8.21 (d, J=8.5 Hz, 1H, Ar), 7.79 (d, J=8.5 Hz, 1H, Ar), 7.61 (t, J=7.6 Hz, 1H, Ar), 7.50-7.36 (m, 4H, Ar), 6.58 (d, J=5.4 Hz, 1H, Ar), 3.85 (s, 3H, -OMe), 3.58 (q, J=5.9, 7.1 Hz, 2H, $H_{10}$), 2.83 (t, J=7.1 Hz, 2H, $H_9$); $^{13}C$ NMR (125 MHz, DMSO-d6) δ (ppm) 153.77, 151.22, 149.97, 148.83, 145.06, 140.87, 134.59, 129.57, 129.24, 128.54, 124.42, 122.07, 120.24, 119.30, 98.94, (Ar), 87.06 (C8), 81.50 (C7), 56.46 (-OMe), 41.75 (C10), 19.08 (C9); HRMS ($ESI^+$) m/z calcd for $C_{20}H_{19}N_4O_2^+$ 347.1503 found 347.1491.

4-((4-(6-((hydroxyimino)methyl)-5-methoxypyridin-2-yl)but-3-yn-1-yl)amino)quinolin-1-ium chloride 68

68

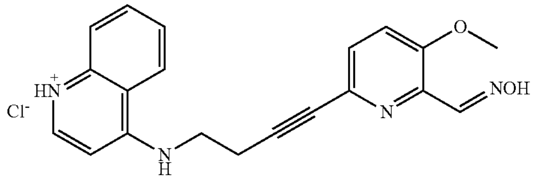

To compound 67 (9.5 mg) in MeOH/$H_2O$ (0.5 mL/0.5 mL), 1.2 N HCl (0.1 mL) was added and agitated for 2 min and left for 10 min at rt. The reaction mixture was concentrated under reduced pressure to afford HCl salt 68 as a white solid in quantitative yield. IR (neat) $v_{max}$ 3186, 3099, 2838, 2237, 1615, 1593, 1449, 1277, 1007, 760, 649, 530, 491 $cm^{-1}$; $^1H$ NMR (500 MHz, $D_2O$) δ (ppm)*8.18-8.08 (m, 3H, Ar), *7.96-7.91 (m, 1.5H, Ar), *7.74-7.70 (m, 1.5H, Ar), *7.62-7.54 (m, 3H, Ar), *7.51-7.40 (m, 4.5H, Ar), *6.73-6.70 (m, 1.5H, Ar), *3.92 (s, 1.5H, -OMe), *3.84 (t, J=6.6 Hz, 1H, $H_{10'}$), 3.80 (s, 3H, -OMe), 3.75 (t, J=6.6 Hz, 2H, $H_{10}$), *2.98 (t, J=6.6 Hz, 1H, $H_{9'}$), 2.89 (t, J=6.6 Hz, 2H, $H_9$); *$^{13}C$ NMR (125 MHz, $D_2O$) δ (ppm) 156.49, 154.95, 142.15, 142.03, 141.86, 141.45, 140.04, 139.68, 138.68, 137.60, 137.00, 134.19, 131.06, 130.37, 128.51, 128.26, 17.55, 127.52, 125.38, 122.39, 120.29, 120.22, 119.12, 116.93, 116.81, 98.55, 98.47 (Ar), 94.74 (C8), 76.76 (C7), 57.71, 57.22 (-OMe), 41.65, 41.10 (C10), 19.5 (C9) (*1:2 ratio of cis-trans isomers); HRMS ($ESI^+$) m/z calcd for $C_{20}H_{20}ClN_4O_2^+$ 347.1503 found 347.1461.

3-methoxy-6-(4-(quinolin-4-ylamino)butyl)picolinaldehyde oxime 69

69

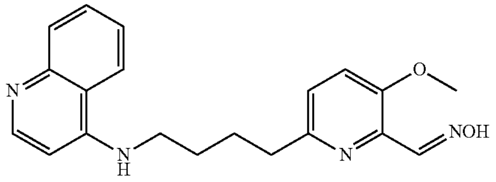

To a degassed solution of methoxy pyridinaldoxime 67 (25 mg, 0.085 mmol, 1 equiv) in dry EtOAc (2 mL), 10% Pd/C (4.5 mg, 0.042 mmol, 0.5 equiv) was added. After flushing with $H_2$ three times, the reaction mixture was stirred at room temperature under $H_2$ (1 atm) for 3 h. Upon completion (monitored by TLC), the catalyst was removed by filtration through a short column of celite, the solvent was evaporated under reduced pressure, and the residue was purified by column chromatography (EtOAc/PE 1:9) to afford oxime 69 as a colourless liquid (24 mg, 95%); $R_f$ (50% EtOAc+PE) 0.40; IR (neat) $v_{max}$ 3327, 2923, 2853, 1582, 1457, 1272, 1126, 968, 763, 694, 540, 473 $cm^{-1}$; *$^1H$ NMR (400 MHz, $CDCl_3$) δ (ppm) 8.42 (2s, 1H, $H_{18}$, $H_{18}$), 8.32 (d, J=5.7 Hz, 1H, Ar), 8.10 (dd, J=1.2, 8.6 Hz, 1H, Ar), 7.79 (d, J=1.2, 8.6 Hz, 1H, Ar), 7.64 (m, 1H, Ar), 7.44 (m, 1H, Ar), 7.39 (d, J=8.7 Hz, 1H, Ar), 7.26 (d, J=8.7 Hz, 1H, Ar), 6.50 (d, J=5.8 Hz, 1H, Ar), 3.87 (s, 3H, -OMe), 3.42 (t, J=6.9 Hz, 1H, $H_{10}$), 3.42 (t, J=6.9 Hz, 1H, $H_{10}$), 2.83 (t, J=7.5 Hz, 1H, $H_7$), 1.87-1.77 (m, 4H, $H_8$, $H_9$); *$^{13}C$ NMR (100 MHz, $CDCl_3$) δ (ppm) 155.21, 154.35, 153.13, 150.73, 148.33, 145.93, 140.73, 138.63, 130.85, 128.33, 125.82, 122.51, 121.43, 120.31, 99.30 (Ar), 56.53 (-OMe), 43.86 (C10), 37.37 (C7), 28.95 (C9), 28.82 (C8) (*1:4 ratio of cis-trans isomers); HRMS ($ESI^+$) m/z calcd for $C_{20}H_{23}N_4O_2^+$ 351.1816 found 351.1827.

4-((4-(6-((hydroxyimino)methyl)-5-methoxypyridin-2-yl)butyl)amino)quinolin-1-ium 70

70

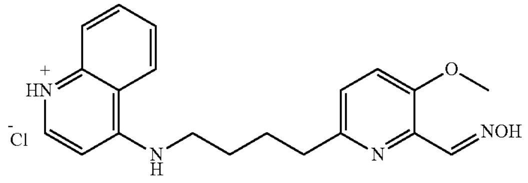

To a compound 69 (8 mg) in MeOH/$H_2O$ (0.5 mL/0.5 mL), 1.2 N HCl (0.1 mL) and agitated for 2 min and left for 10 min at rt. The reaction mixture was concentrated under reduced pressure to obtain HCl salt 70 as a white solid in quantitative yield. IR (neat) $v_{max}$ 3237, 3111, 2926, 1617, 1594, 1452, 1291, 1011, 764, 663, 592 $cm^{-1}$; $^{1}H$ NMR (500 MHz, $D_2O$) δ (ppm) 8.20 (s, 1H, $H_{18}$), 8.19 (d, J=8.6 Hz, 1H, Ar), 8.04 (d, J=8.6 Hz, 1H, Ar), 7.94-7.87 (m, 2H, Ar), 7.75 (dd, J=8.6, 18.8 Hz, 1H, Ar), 7.64 (t, J=8.8 Hz, 1H, Ar), 6.64 (d, J=7.2 Hz, 1H, Ar), 3.93 (s, 3H, -OMe), 3.55 (t, J=6.5 Hz, 1H, $H_{10}$), 3.01 (t, J=6.8 Hz, 1H, $H_7$), 1.95-1.80 (m, 4H, $H_8$, $H_9$); *$^{13}C$ NMR (125 MHz, $D_2O$) δ (ppm) 156.07, 154.21, 150.14, 141.63, 139.57, 137.60, 134.14, 133.86, 129.10, 128.69, 127.47, 122.29, 120.27, 116.86, 98.31 (Ar), 57.45 (-OMe), 42.83 (C10), 32.20 (C7), 26.12 (C9), 25.81 (C8) (*1:2 ratio of cis-trans isomers); HRMS ($ESI^+$) m/z calcd for $C_{20}H_{23}N_4O_2^+$351.1816 found 351.1782.

(3aS,4S,6R,6aR)-6-(6-amino-9H-purin-9-yl)-N-(4-(6-(-(hydroxyimino)methyl)-5-methoxypyridin-2-yl)but-3-yn-1-yl)-2,2-dimethyltetrahydrofuro[3,4-d][1,3]dioxole-4-carboxamide 72

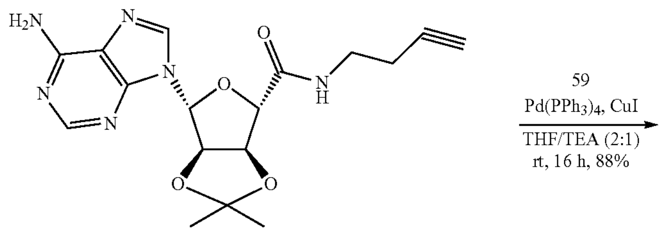

54

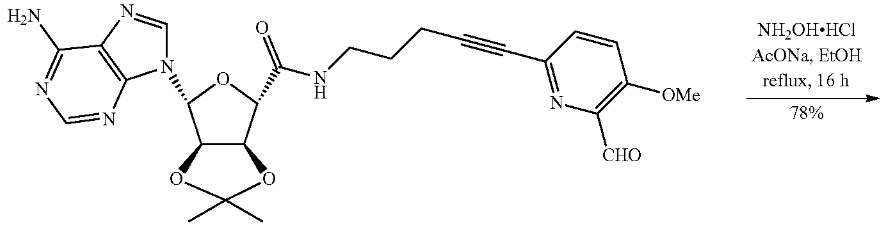

71

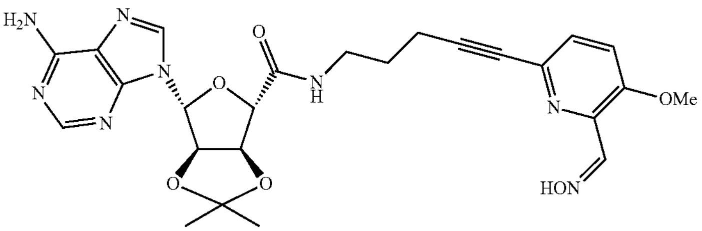

72

To a degassed solution of commercially available 6-bromo-3-methoxypicolinaldehyde 62 (192 mg, 0.887 mmol, 1.1 equiv) in THF/$Et_3N$ (5 mL/5 mL), Pd[$PPh_3$]$_4$ (140 mg, 0.121 mmol, 0.15 equiv) and CuI (46 mg, 0.242 mmol, 0.3 equiv) were added. After degassing the reaction mixture for 5 min at room temperature, alkyne 54 (300 mg, 0.806 mmol, 1 equiv) in THF (5 mL) was added dropwise and the reaction mixture was stirred at room temperature for 16 h. After completion (monitored by TLC), the reaction mixture was concentrated under reduced pressure and the residue was passed through a small filter column (MeOH/EtOAc 5:95) to afford the desired coupled methoxy piconaldehyde 71 (360 mg, 88%) as a light yellow solid. This crude aldehyde was directly used for the next step without purification.

A solution of aldehyde 71 (220 mg, 0.433 mmol, 1 equiv), hydroxylamine hydrochloride (60 mg, 0.867 mmol, 2 equiv), and $CH_3CO_2Na$ (107 mg, 1.299 mmol, 3 equiv) in dry ethanol (7 mL) was stirred at reflux during 16 h. Upon completion (monitored by TLC), the solids were removed by filtration through a short celite pad, the solvent was evaporated, and the residue was purified by column chromatography (MeOH/EtOAc 1:9) to afford oxime 72 as a white solid (180 mg, 78%). $R_f$ (30% MeOH+EtOAc) 0.2; IR (neat) $v_{max}$ 3185, 2926, 1640, 1464, 1264, 1209, 1090, 971, 868, 797, 647, 510 $cm^1$; $^{1}H$ NMR (400 MHz, MeOD) δ (ppm) 8.39-8.11 (3s, 3H, Ar, —C═NOH), 7.37 (d, J=8.6, 1 H, $H_4$), 7.26 (d, J=8.6 Hz, 1H, $H_5$), 6.34 (br s, H, —CH), 5.57 (dd, J=1.8, 6.0 Hz, 1H, —CH), 5.41 (br d, J=6.0 Hz, 1H, —CH), 4.68 (d, J=1.8 Hz, 1H, —CH), 3.89 (s, 3H, —$OCH_3$), 3.21 (m, 1H, —$CH_2$), 3.09 (m, 1H, —$CH_2$), 2.27 (m, 1H, —$CH_2$), 2.10 (m, 1H, —$CH_2$), 1.57 (s, 3H, —$CH_3$), 1.37 (s, 3H, —CH3); $^{13}C$ NMR (100 MHz, MeOD) δ (ppm) 172.07, 157.33, 155.15, 153.99, 150.30, 145.21, 142.55, 141.69, 135.92, 129.89, 120.84, 120.49, 115.17 (Ar), 92.41 (C16), 88.65 (C15), 87.34 (C8), 85.36 (C14), 85.26 (C13), 81.58 (C7), 56.74 (C30), 38.79 (C10), 27.29 (C28), 25.54 (C29), 20.47 (C9); HRMS ($ESI^+$) m/z calcd for $C_{24}H_{27}N_8O_6^+$ 523.2048 found 523.2038.

VI—Synthesis of Tri Functional Neca Compounds

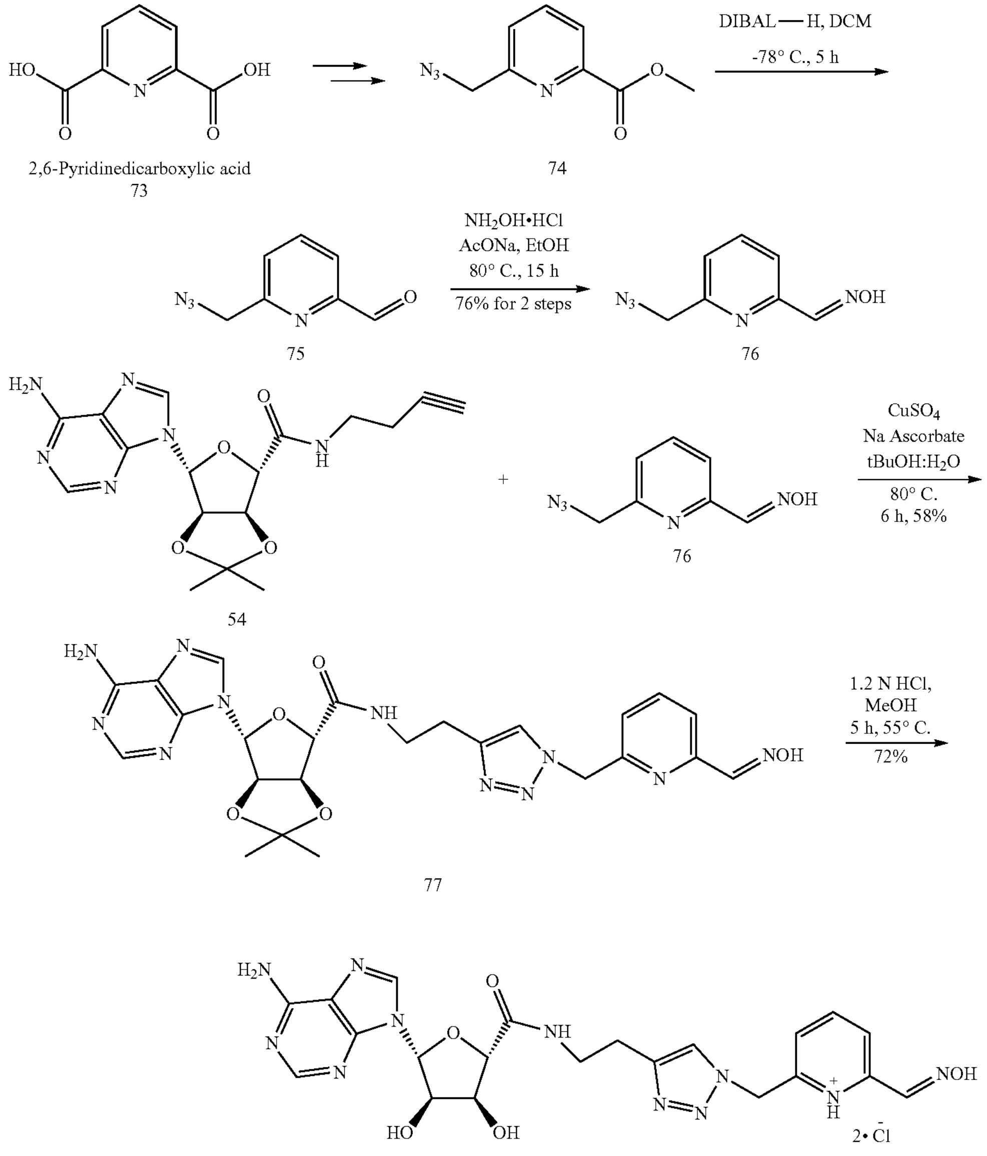

2,6-Pyridinedicarboxylic acid
73
74
75
76
54
76
77
78

6-(azidomethyl)picolinaldehyde 75

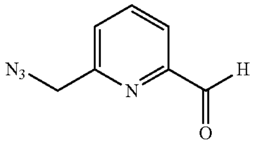

75

The synthesis of methyl 6-(azidomethyl)picolinate 74 was achieved by using a well-established procedure from Harekrushna, B. et al.[1].

To the solution of azido ester 74 (100 mg 0.521 mmol, 1 equiv) in dry $CH_2Cl_2$ (5 mL) at −78° C., DIBAL-H (1 M solution in $CH_2Cl_2$, 1.563 mL, 1.563 mmol, 3 equiv) was added dropwise and the reaction mixture was stirred at −78° C. for 5 h. After completion of the reaction, the reaction mixture was quenched with MeOH (3 mL), and the cooling bath was removed. When the mixture was warmed to room temperature, the reaction mixture was diluted with $H_2O$ and extracted with EtOAc. The combined organic layers are dried over $MgSO_4$. The solids were filtered off and the solvent is evaporated to get aldehyde 75. This crude aldehyde 75 was directly subjected for the next step without purification. IR (neat) $\nu_{max}$ 2836, 2098, 1709, 1591, 1457, 1255, 990, 777, 641 $cm^{-1}$; $^1H$ NMR (400 MHz, $CDCl_3$) δ (ppm) 10.04 (s, 1H), 7.94-7.86 (m, 2H), 7.56 (m, 2H), 4.57 (s, 2H); $^{13}C$ NMR (100 MHz, $CDCl_3$) δ (ppm) 193.07, 156.73, 152.59, 138.11, 126.05, 102.78, 55.15; HRMS ($ESI^+$) m/z calcd for $C_7H_7N_4O_1^+$ 163.0604 found 163.0614.

6-(azidomethyl)picolinaldehyde oxime 76

76

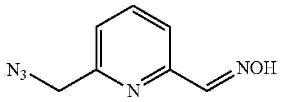

A solution of crude picolinaldehyde 75 (0.521 mmol, 1 equiv), hydroxylamine hydrochloride (73 mg, 1.042, 2 equiv), and $CH_3CO_2Na$ (128 mg, 1.563 mmol, 3 equiv) in dry ethanol (5 mL) was stirred at 80° C. during 16 h. Upon completion, the solids were removed by filtration through a short column of celite, the solvent was evaporated, and the residue was purified by column chromatography (EtOAc/P.E: 1:9) to afford the oxime 76 (70 mg, 76%) as thick syrup. IR (neat) $v_{max}$ 3182, 30102889, 2084, 1572, 1590, 1459, 12666, 1233, 1158, 994, 966, 782, 741, 651, 619, 501 $cm^{-1}$; $^1H$ NMR (400 MHz, $CD_3OD$) δ (ppm) 8.10 (s, 1H), 7.86-7.76 (m, 2H), 7.40 (dd, J=1.8, 6.8 Hz, 2H), 4.48 (s, 2H); $^{13}C$ NMR (100 MHz, $CD_3OD$) δ (ppm) 157.29, 153.94, 149.93, 139.26, 1323.66, 120.86, 56.16; HRMS ($ESI^+$) m/z calcd for $C_7H_8N_5O_1^+$ 178.0721 found 178.0723508.1867.

(3aS,4S,6R,6aR)-6-(6-amino-9H-purin-9-yl)-N-(2-(1-((6-(-(hydroxyimino)meth-yl)pyridin-2-yl)methyl)-1H-1,2,3-triazol-4-yl)ethyl)-2,2-dimethyltetrahydrofuro[3,4-d][1,3]dioxole-4-carboxamide 77

77

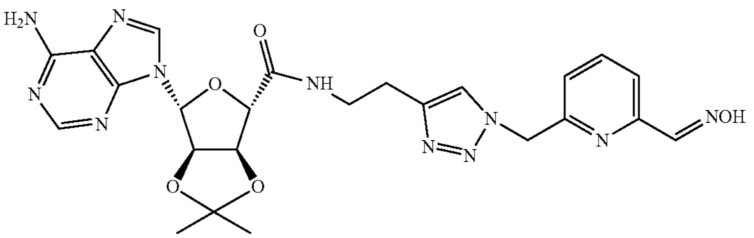

To a stirred solution of oxime 76 (52 mg, 0.295 mmol, 1.1 equiv) in t-BuOH/$H_2O$ (2 mL/1.5 mL), $CuSO_4$ (17 mg, 0.107 mmol, 0.4 equiv), sodium ascarbate (21 mg, 0.107 mmol, 0.4 equiv) and alkyne 54 (100 mg, 0.268 mmol, 1 equiv) were added. The reaction mixture was allowed to stir for 6 h at 80° C. After completion (monitored by TLC), the reaction mixture was concentrated under reduced pressure and the residue was purified by column chromatography (MeOH/EtOAc: 5:95) to afford the desired triazole compound 77 as a white solid (85 mg, 58%). IR (neat) $v_{max}$ 3192, 2924, 1644, 1598, 1458, 1376, 1209, 1155, 1057, 992, 868, 797, 648, 511 $cm^{-1}$; $^1H$ NMR (400 MHz, $CD_3OD$) δ (ppm) 8.20 (s, 1H), 8.08 (s, 1H), 8.05 (s, 1H), 7.75-7.70 (m, 2H), 7.12 (m, 1H), 6.30 (d, J=1.7 Hz, 1H), 5.62 (s, 2H), 5.50 (dd, J=1.9, 6.1 Hz, 1H), 4.62 (d, J=1.9 Hz, 1H), 3.24-3.01 (m, 2H), 2.61-2.41 (m, 2H), 1.57 (s, 3H), 1.38 (s, 3H); $^{13}C$ NMR (100 MHz, $CD_3OD$) δ (ppm) 171.91, 157.38, 156.08, 153.97, 150.27, 150.06, 146.45, 142.54, 139.28, 124.46, 123.53, 121.07, 120.55, 115.24, 92.65, 88.38, 85.28, 85.06, 56.09, 39.64, 27.31, 25.91, 25.55; HRMS ($ESI^+$) m/z calcd for $C_{24}H_{28}N_{11}O_5^+$ 550.2237 found 550.2269.

(2S,3S,4R,5R)-5-(6-amino-9H-purin-9-yl)-3,4-dihydroxy-N-(2-(1-((6-(-(hydroxyimino)-methyl)pyridin-2-yl)methyl)-1H-1,2,3-triazol-4-yl)ethyl)tetrahydrofuran-2-carboxamide. hydrochloride 78

78

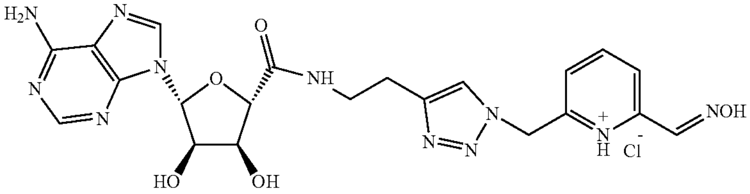

To a stirred solution of triazole 77 (23 mg, 0.042 mmol, 1 equiv) in dry MeOH (2 mL), 1.2 N HCl (127 μL, 0.42 mmol, 10 equiv) was added and the reaction mixture was stirred at 55° C. for 4 h. After completion, the reaction mixture was directly concentrated under reduced pressure and the residue was purified by reverse phase column chromatography (MeOH/$H_2O$ 3:7) to afford HClsalt 78 (15 mg, 72%) as a white solid. IR (neat) $v_{max}$ 3196, 1640, 1588, 1458, 1427, 1306, 1254, 1113, 1054, 997, 796, 647 $cm^{-1}$; $^1H$ NMR (400 MHz, $CD_3OD$) δ (ppm) 7.99 (s, 1H), 8.89 (s, 1H), 7.83 (s, 1H), 7.42 (t, J=7.8 Hz, 1H), 7.29 (t, J=9.3 Hz, 1H), 7.20 (s, 1H), 7.13 (t, J=7.8 Hz, 1H), 5.77 (d, J=8.3 Hz, 1H), 5.44-5.38 (2d, J=14.8 Hz, 2H), 4.43 (s, 1H), 4.32 (br d, J=5.0 Hz, 1H), 4.08 (dd, J=4.8, 8.3 Hz, 1H), 3.61 (m, 1H), 3.35 (m, 1H), 3.08-299 (m, 1H), 3.96-288 (m, 1H); $^{13}C$ NMR (100 MHz, $CD_3OD$) δ (ppm) 172.32, 155.44, 153.78, 151.99, 150.84, 147.61, 142.13, 138.97, 124.62, 124.41, 121.56, 119.75, 89.21, 85.20, 73.72, 72.06, 55.28, 49.50 (MeOH), 39.92, 24.77; HRMS ($ESI^+$) m/z calcd for $C_{21}H_{334}N_{11}O_5^+$ 510.1957 found 510.1956.

REFERENCES

1. Harekrushna, B. et al. *Chem. Eur. J.* 2015, 21, 10179-10184.

VII—Synthesis of Tri Functional Pseudo Neca Compound

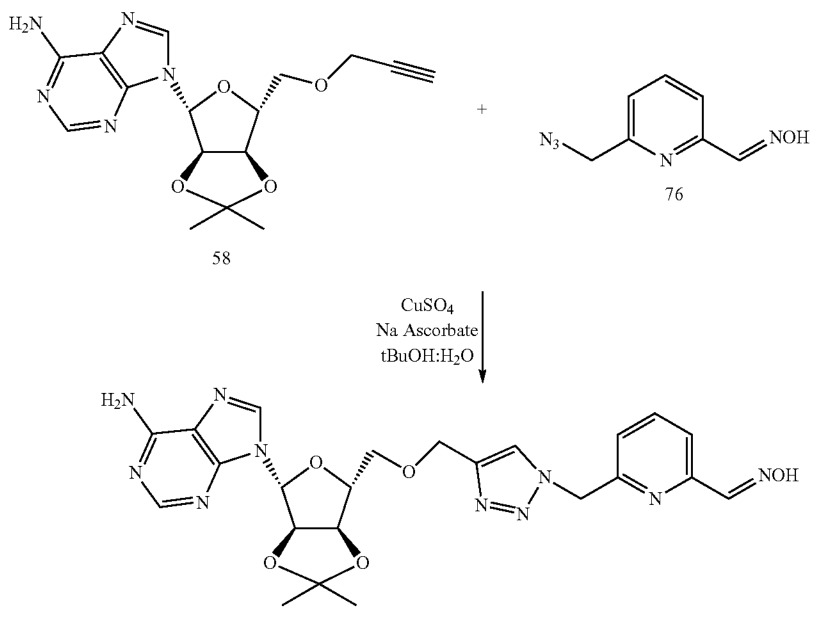

58

76

79

N-(9-((3aR,4R,6R,6aR)-6-(((1-((6-(-(hydroxyimino)methyl)pyridin-2-yl)methyl)-1H-1,2,3-triazol-4-yl)methoxy)methyl)-2,2-dimethyltetrahydrofuro[3,4-d][1,3]dioxol-4-yl)-9H-purin-6-yl)benzamide 79

79

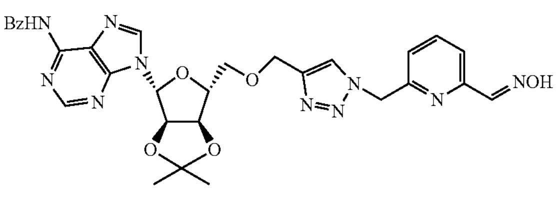

To a stirred solution of oxime 76 (44 mg, 0.245 mmol, 1.1 equiv) in t-BuOH/$H_2O$ (2 mL/1.5 mL), $CuSO_4$ (17 mg, 0.045 mmol, 0.2 equiv), sodium ascarbate (18 mg, 0.045 mmol, 0.2 equiv) and alkyne 58 (100 mg, 0.223 mmol, 1 equiv) were added. The reaction mixture was allowed to stir for 6 h at 80° C. After completion (monitored by TLC), the reaction mixture was concentrated under reduced pressure and the residue was purified by column chromatography (pure EtOAc-MeOH/EtOAc: 5:95) to afford the desired triazole compound 79 as a white solid (100 mg, 72%). IR (neat) $v_{max}$ 2924, 1698, 1610, 1581, 1455, 1248, 1211, 1070, 994, 796, 709, 645, 563 $cm^{-1}$; $^1H$ NMR (400 MHz, $CD_3OD$) δ (ppm) 10.88 (br s, 1H), 9.31 (br s, 1H), 8.77 (s, 1H), 8.31 (s, 1H), 8.14 (s, 1H), 7.95-7.80 (m, 3H), 7.51-7.28 (m, 5H), 6.99 (d, J=7.5 Hz, 1H), 6.25 (d, J=2.3 Hz, 1H), 5.63 (s, 2H), 5.21 (dd, J=2.2, 5.9 Hz, 1H), 4.98 (dd, J=1.6, 5.9 Hz, 1H), 4.65-4.50 (m, 3H), 3.82 (dd, J=2.2, 10.6 Hz, 1H), 3.70 (dd, J=3.0, 10.6 Hz, 1H), 1.61 (s, 3H), 1.37 (s, 3H); $^{13}C$ NMR (100 MHz, $CD_3OD$) δ (ppm) 165.35, 154.38, 152.69, 151.64, 151.44, 150.02, 149.19, 143.91, 141.90, 137.62, 133.31, 128.56, 127.93, 124.13, 122.78, 122.07, 120.42, 114.09, 92.26, 86.27, 85.28, 81.85, 70.67, 64.47, 55.03, 27.11, 25.24; HRMS ($ESI^+$) m/z calcd for $C_{30}H_{31}N_{10}O_6^+$ 627.2414 found 627.2423.

Example 2: In Vitro Reactivation of Human Acetylcholinesterase (hAChE) by Compounds of the Invention Compounds 57, 78, 25 and 26 of example 1 were tested for their activation properties of hAChE inhibited by O-ethyl S-[2-(diisopropylamino)ethyl] methylphosphonothioate (VX), tabun, sarin or paraoxon. 2-PAM (pralidoxime or 2-[(E)-(hydroxyimino)methyl]-1-methylpyridinium) and HI6 (asoxime chloride or [1-[(4-carbamoylpyridin-1-ium-1-yl)methoxymethyl]pyridin-2-ylidene]methyl-oxoazanium dichloride) were used as comparative compounds.

The protocol was as follows:

Materials and methods are already described in WO2017021319, in European Journal of Medicinal Chemistry 2014, 78, 455-467, and in *J. Med. Chem.* 2018, 61, 7630-7639.

$IC_{50}$ measurements. Recombinant hAChE was produced and purified as previously described (Carletti et al 2008 J Am Chem Soc 130(47): 1601 1-20). Compounds were dissolved in MeOH to make a 5 mM or a 10 mM stock solution and further diluted in phosphate buffer (sodium phosphate 0.1 M, pH 7.4). Recombinant hAChE activity was measured spectrophotometrically (absorbance at 412 nm) in the presence of various concentrations of oximes in 1 mL Ellman's buffer (sodium phosphate 0.1 M, pH 7.4, 0.1% BSA, 0.5 mM DTNB, 25° C.). Measurements were performed at least in duplicate for each concentration tested. The concentration of compound producing 50% of enzyme inhibition was determined by non-linear fitting using ProFit (Quantumsoft) using the standard $IC_{50}$ equation: % Activity=100*$IC_{50}$/($IC_{50}$+[Ox]).

Inhibition of hAChE by OPNAs. Recombinant hAChE was produced and purified as previously described (see reference: http://www.ncbi.nlm.nih.gov/pubmed/18975951). VX and Tabun were from DGA maitrise NRBC (Vert le Petit, France). Stock solution of VX, Sarin, Tabun and Paraoxon were 5 mM in isopropanol. The inhibition of 120 μM hAChE was carried out with a 5-fold excess of OPNAs and was performed in tris buffer (20 mM, pH 7.4, 0.1% BSA) at 25° C. After incubation for 20 minutes, inhibited hAChE was desalted on PD-10 column (GE Healthcare).

Reactivation of hAChE inhibited by OPNAs. OPNA-inhibited hAChE was incubated at 37° C. with at least 4 or 5 concentrations of oxime in phosphate buffer (0.1 M, pH 7.4, 0.1% BSA). The final concentration of MeOH in the incubation mix was below 2% and had no influence on the enzyme stability. At time intervals ranging from 1 to 10 minutes depending on the reactivation rate, 10 aliquots of each solution containing the different concentrations of oxime were transferred to cuvettes containing 1 mM acetylthiocholine in 1 mL Ellman's buffer (phosphate 0.1 M, pH 7.4, 0.1% BSA, 0.5 mM DTNB, 25° C.) for measurement of hAChE activity.

The enzyme activity in the control remained constant during the experiment. The percentage of reactivated enzyme (% $E_{react}$) was calculated as the ratio of the recovered enzyme activity and activity in the control. The apparent reactivation rate kobs for each oxime concentration, the dissociation constant $K_D$ of inhibited enzyme-oxime complex (E-POx) and the maximal reactivation rate constant $k_r$, were calculated by non-linear fit with ProFit (Quantumsoft) using the standard oxime concentration-dependent reactivation equation derived from the following scheme:

$$E—P + Ox \overset{K_D}{\rightleftharpoons} E—POx \overset{k_r}{\longrightarrow} E + POx$$

$$\%\ E_{react} = 100\star(1 - e^{kobs\star t}) \text{ and } k_{obs} = \frac{k_r\star[Ox]}{K_D + [Ox]}$$

E-P=enzyme

Ox=oxime compound

E-Pox=enzyme-oxime complex

The results are as follows (Tables 1 and 2):

TABLE 1

Reactivation of OP-inhibited human hAChE by oximes 2-PAM, HI6, 57, 78, 25, 26.

| OP | Oxime (μM) | $k_r$ ($min^{-1}$) | $K_D$ (μM) | $kr_2$ ($mM^{-1}$ $min^{-1}$) |
|---|---|---|---|---|
| VX | 2-PAM | 0.19 ± 0.013 | 26 ± 7 | 7.3 |
| | HI6 | 0.38 ± 0.02 | 19 ± 4 | 20 |
| | 57 | 0.58 ± 0.07 | 100 ± 24 | 6 |
| | 78 | 0.2 ± 0.01 | 98.5 ± 17 | 2 |
| | 25 | 0.05 ± 0.001 | 1.2 ± 0.1 | 42 |
| | 26 | 0.06 ± 0.001 | 3 ± 0.3 | 20 |
| Sarin | 2-PAM | 0.27 ± 0.02 | 25 ± 7 | 10.8 |
| | HI6 | 0.76 ± 0.06 | 57 ± 11 | 13.3 |
| | 57 | 1.2 ± 0.15 | 110 ± 31 | 10.9 |
| | 78 | 3.7 ± 0.5 | 181 ± 46 | 20.4 |

TABLE 1-continued

Reactivation of OP-inhibited human hAChE by oximes 2-PAM, HI6, 57, 78, 25, 26.

| OP | Oxime (μM) | $k_r$ ($min^{-1}$) | $K_D$ (μM) | $kr_2$ ($mM^{-1}$ $min^{-1}$) |
|---|---|---|---|---|
| | 25 | 0.03 ± 0.0006 | 0.35 ± 0.1 | 86 |
| | 26 | 0.027 ± 0.0006 | 1.1 ± 0.1 | 25 |
| Tabun | 2-PAM | 0.47 ± 0.2 | 211 ± 113 | 2.2 |
| | HI6 | 0 | 0 | 0 |
| | 57 | 1.2 ± 0.07 | 32 ± 7 | 38 |
| | 78 | 0.15 ± 0.01 | 5.4 ± 1.8 | 29 |
| | 25 | 0 | 0 | 0 |
| | 26 | 0 | 0 | 0 |
| Paraoxon | 2-PAM | 0.066 ± 0.02 | 68 ± 16 | 1 |
| | HI6 | 290 ± 70 | 0.1 ± 0.01 | 0.36 |
| | 57 | 0.36 ± 0.16 | 57 ± 9 | 6.4 |
| | 78 | 0 | 0 | 0 |
| | 25 | 0 | 0 | 0 |
| | 26 | 0 | 0 | 0 |

Table 1 shows that compound 57 shows higher reactivation kinetics ($k_r$ in $min^{-1}$) for VX, Tabun, Sarin and Paraoxon, as compared to references 2-PAM and HI6; and that compound 78 shows higher reactivation kinetics ($k_r$ in $min^{-1}$) for VX, Tabun and Sarin, as compared to references 2-PAM and HI6.

Compounds 25 and 26 show strong affinities for AChE inhibited by VX or Sarin. These compounds show higher reactivation (kr2 $mM^{-1}$ $min^{-1}$) than 2-PAM and HI6.

TABLE 2

IC50 for AChE of oximes: 2-PAM, HI6, 57, 78, 25, 26.

| Oxime | $IC_{50}$ (μM) |
|---|---|
| 2-PAM | 580 ± 28 |
| HI6 | 82 ± 6 |
| 57 | 79% at 1.5 mM |
| 78 | 840 ± 106 |
| 25 | 4 ± 0.4 |
| 26 | 11 ± 2 |

Table 2 shows that compounds 25 and 26 show very high affinities for AChE, which are higher than the ones of 2-PAM and HI6. Compound 25 shows the best affinity.

The invention claimed is:

1. Compound of formula (I), or one of its pharmaceutically acceptable salts:

(I)

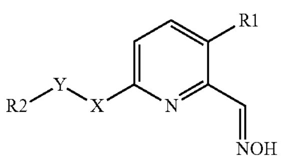

wherein:

R1 is H, or a linear or cyclic C1-C7 alkoxy radical;

—X—Y— is —CH2-(CH2)n-, —C≡C—,

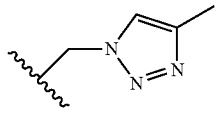

or —X—Y— is Br and R2 does not exist;

n is an integer between 0 and 5;

R2 is a group chosen from alkyl, aryl, aralkyl, heteroaryl, —R3-N(R4)(R5), radical A, radical B, radical C and radical D, wherein radical A or radical B or radical C or radical D is optionally linked to —Y—X— by an alkyl group:

A

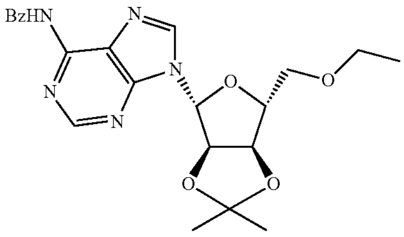

B

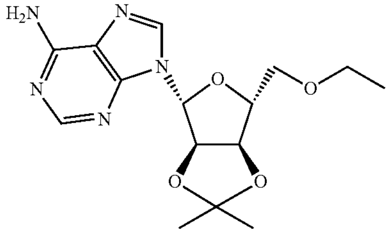

C

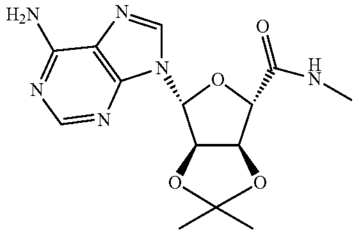

D

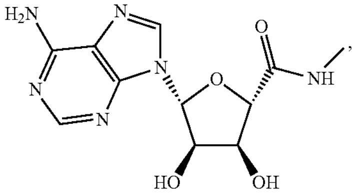

R3 is a C1-C4 alkyl group, and

R4 and R5 are identical or different and each independently represent H, a naphthyl radical, a 5-fluoroquinolin-4-yl radical, a quinolin-4-yl radical or a 8-methoxyquinolin-4-yl radical or R4 and R5 form together with the nitrogen atom a 4-benzyl-piperazin-1-yl radical or a 3,7-dimethyl-2,6-dioxo-2,3,6,7-tetrahydro-1H-purin-1-yl radical.

2. Compound according to claim 1, wherein the compound has scaffold 1 below:

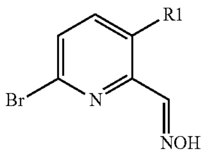

Scaffold 1 wherein R1 is as defined in claim 1.

3. Compound according to claim 1, wherein the compound has scaffold 2 below:

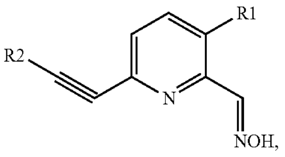

Scaffold 2 wherein R1 and R2 are as defined in claim 1.

4. Compound according to claim 3, wherein R2 is chosen from radical A, radical B, radical C and radical D:

A

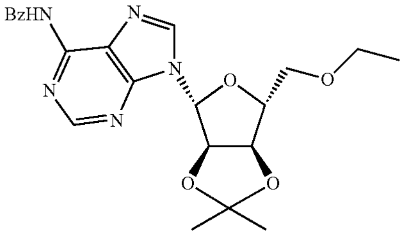

B

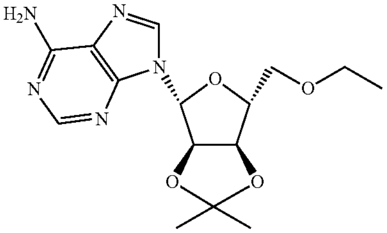

C

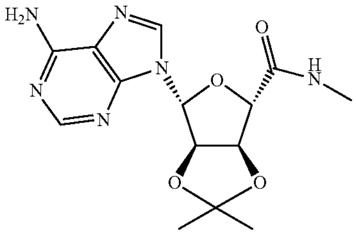

D

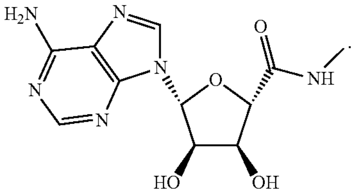

5. Compound according to claim 3, wherein R2 is alkyl, heteroaryl, aralkyl or —R3-N(R4)(R5), wherein R3 is a C1-C4 alkyl group, R4 is H, and R5 is chosen from a naphthyl radical, a 5-fluoroquinolin-4-yl radical, a quinolin-4-yl radical or a 8-methoxyquinolin-4-yl radical.

6. Compound according to claim 3, wherein R2 is —R3-N(R4)(R5), wherein R3 is a C1-C4 alkyl group, and R4 and R5 form together with the nitrogen atom a 4-benzyl-piperazin-1-yl radical or a 3,7-dimethyl-2,6-dioxo-2,3,6,7-tetrahydro-1H-purin-1-yl radical.

7. Compound according to claim 1, wherein the compound has scaffold 3 below:

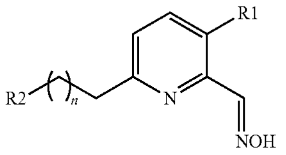

Scaffold 3 wherein R1 and R2 are as defined in claim 1 and n is an integer between 0 and 5.

8. Compound according to claim 7, wherein R2 is alkyl, aryl, aralkyl or —R3-N(R4)(R5), wherein R3 is a C1-C4 alkyl group, R4 is H, and R5 is chosen from a naphthyl radical, a 5-fluoroquinolin-4-yl radical, a quinolin-4-yl radical or a 8-methoxyquinolin-4-yl radical.

9. Compound according to claim 7, wherein R2 is —R3-N(R4)(R5), wherein R3 is a C1-C4 alkyl group, and R4 and R5 form together with the nitrogen atom a 4-benzyl-piperazin-1-yl radical.

10. Compound according to claim 1, wherein the compound has scaffold 4 below:

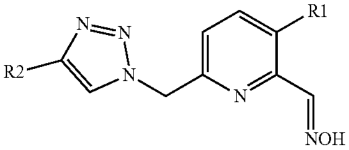

Scaffold 4 wherein R1 and R2 are as defined in claim 1.

11. Compound according to claim 10, wherein R2 is chosen from radical A, radical C and radical D:

A

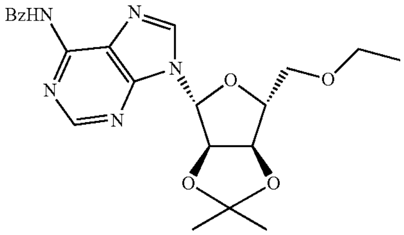

C

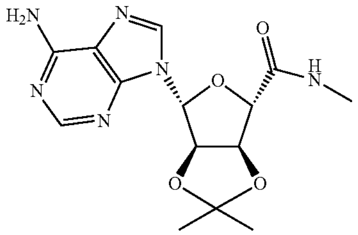

-continued

D

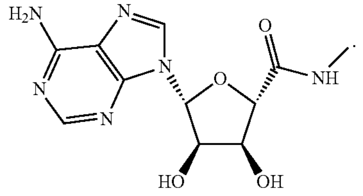

12. Compound according to claim 1, wherein the compound is chosen from:

6-Bromopicolinaldehyde oxime 2:

2

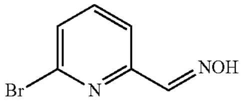

6-(5-phenylpent-1-yn-1-yl)picolinaldehyde oxime 5:

5

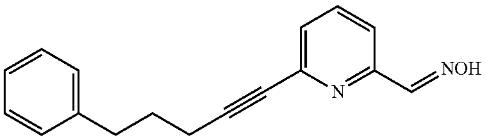

6-(5-phenylpentyl)picolinaldehyde oxime 7:

7

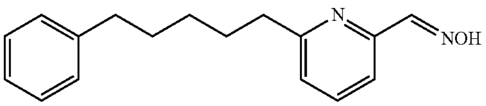

6-(pentadec-1-yn-1-yl)picolinaldehyde oxime 9:

9

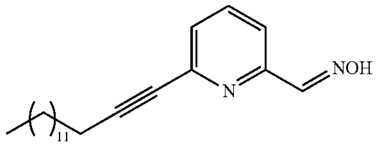

6-pentadecylpicolinaldehyde oxime 10:

10

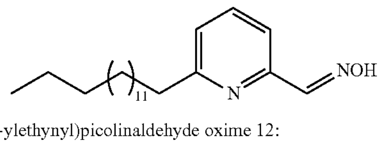

6-(pridin-3-ylethynyl)picolinaldehyde oxime 12:

12

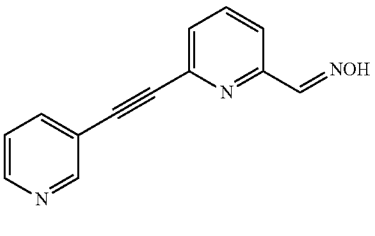

-continued 2-((hydroxyimino)methyl)-6-(pyridin-1-ium-3-ylethynyl)pyridin-1-ium chloride 13:

13

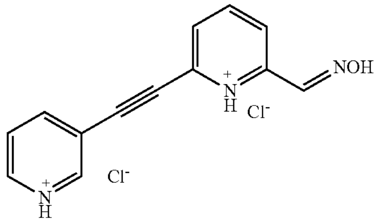

N-(4-{6-[hydroxyimino)methyl]pyridine-2-yl}but -3-yn-1-yl) naphthalene-1-amine 19:

19

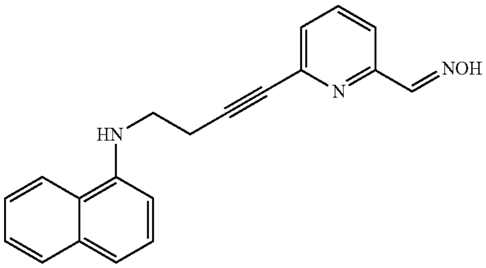

N-(4-{6-[hydroxyimino)methyl]pyridine-2-yl}but -3-yn-1-yl) naphthalene-1-amine 20:

20

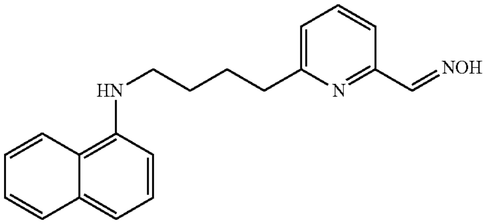

6-(4-(quinolin-4-ylamino)but-1-yn-1-yl)picolinaldehyde oxime 25:

25

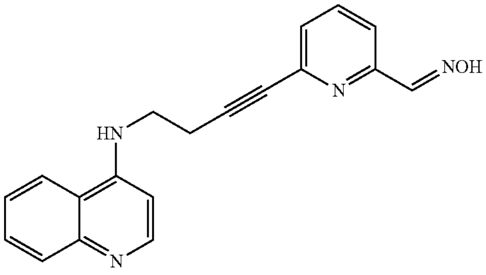

Methyl 3-hydroxy-6-(4-(quinoline-4-ylamino)butyl)picolinate 26:

26

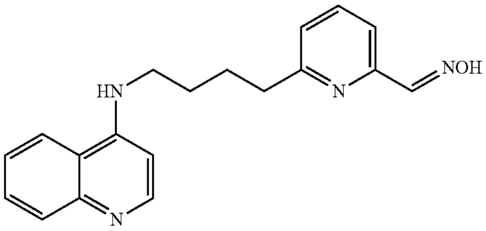

-continued 6-(4-((5-fluoroquinolin-4-yl)amino)but-1-yn-1-yl)picolinaldehyde oxime 30:

30

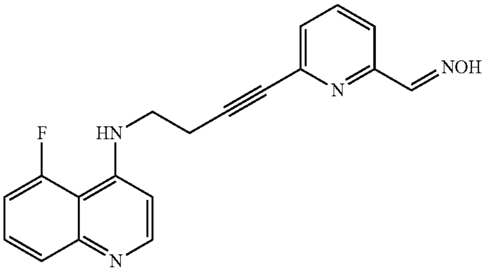

6-(4-((5-fluoroquinolin-4-yl)amino)butyl)picolinaldehyde oxime 31:

31

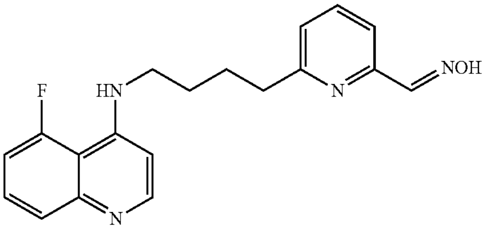

6-(4-((8-methoxyquinolin-4-yl)amino)but-1-yn-1-yl)picolinaldehyde oxime 36:

36

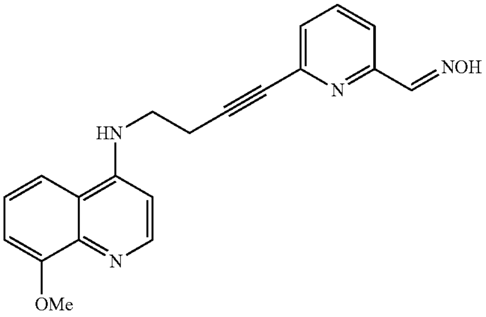

6-(4-((8-methoxyquinolin-4-yl)amino)butl)picolinaldehyde oxime 37:

37

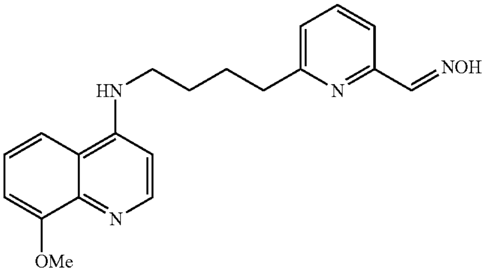

6-(3-(4-benzylpiperazin-1-yl)prop-1-yn-1-yl)picolinaldehyde oxime 42:

42

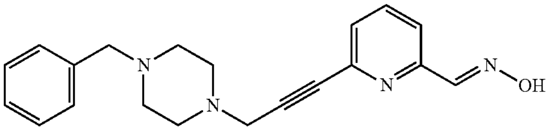

-continued 6-(3-(4-benzylpiperazin-1-yl)propyl)picolinaldehyde oxime 43:

43

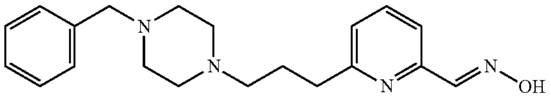

6-(4-(4-benzylpiperazin-1-yl)but-1-yn-1-yl)picolinaldehyde oxime 47:

47

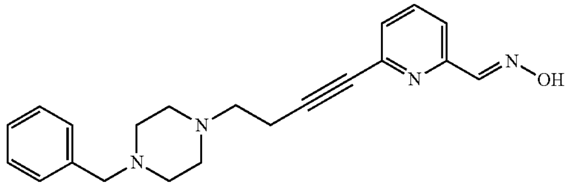

6-(4-(4-benzylpiperazin-1-yl)butl)picolinaldehyde oxime 48:

48

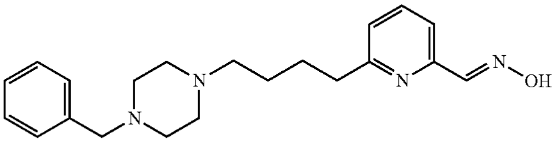

6-(4-(3,7-dimethyl-2,6-dioxo-2,3,6,7-tetrahydro-1H-purin-1-yl)but-1-yn-1-yl)picolinaldehyde oxime 51:

51

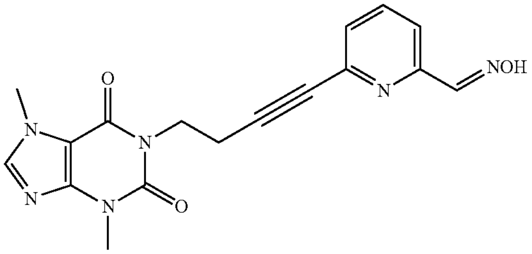

(3aS,4S,6R,6aR)-6-(6-amino-9H-purin-9-yl)-N-(4-6-(hydroxyimino)methyl)pyridin-2-yl)but-3-yn-1-yl)-2,2-dimethyltetrahydrofuro[3,4-d][1,3]dioxole-4-carboxamide 56:

56

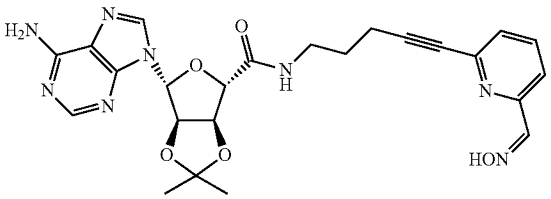

(2S,3S,4R,5R)-5-(6-amino-9H-purin-9-yl)-3,4-dihydroxy-N-(4-(6-hydroxyimino)methyl)pyridin-2-yl)but-3-yn-1-yl)tetrahydrofuran-2-carboxamide 57:

57

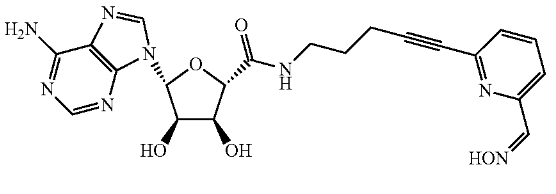

-continued

N-(9-(3aR,4R,6R,6aR)-6-(((3-(6-(hydroxyimino)methyl)pyridin-2-yl)prop-2-yn-1-yl)oxy)methyl)-2,2-dimethyltetrahydrofuro[3,4-d][1,3]dioxol-4-yl)-9H-purin-6-yl)benzamide 60:

60

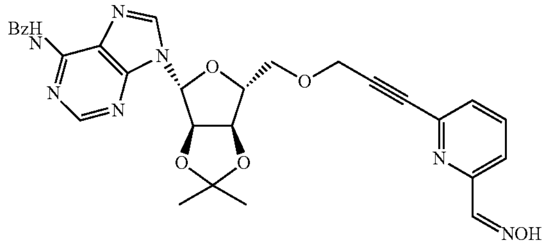

6-(3-(((3aR,4R,6R,6aR)-6-(6-amino-9H-purin-9-yl)-2,2-dimethyltetrahyrofuro[3,4-d][1,3]dioxol-4-yl)methoxy)prop-1-yn-1-yl)picolinaldehyde oxime 61:

61

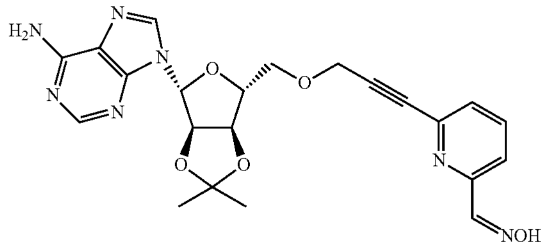

3-methoxy-6-(5-phenylpent-1-yn-1-yl)picolinaldehyde oxime 64:

64

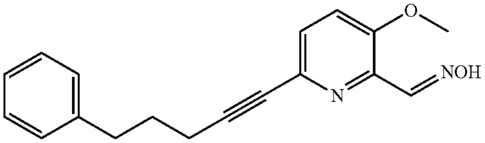

3-methoxy-6-(5-phenylpentyl)picolinaldehyde oxime 65:

65

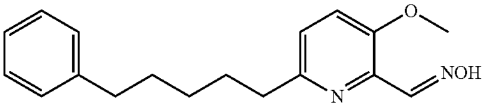

3-methoxy-6-(4-(quinolin-4-ylamino)but-1-yn-1-1yl)picolinaldehyde oxime 67:

67

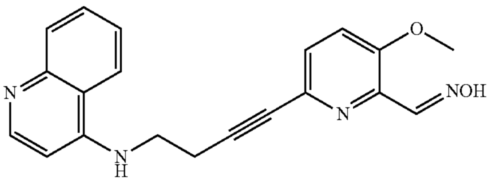

4-((4-(6-((hydroxyimino)methyl)-5-methoxypyridin-2-yl)but-3-yn-1-yl)amino)quinolin-1-ium chloride 68:

68

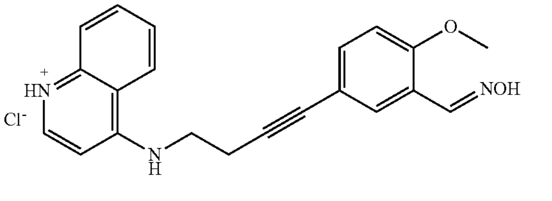

-continued 3-methoxy-6-(4-(quinolin-4-ylamino)butyl)picolinaldehyde oxime 69:

69

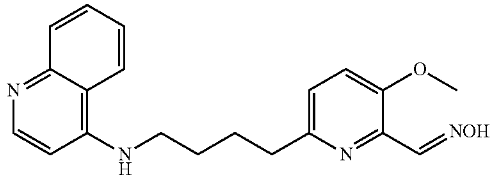

4-((4-(6-((hydroxyimino)methyl)-5-methoxypyridin-2-yl)butyl)amino) quinolin-1-ium 70:

70

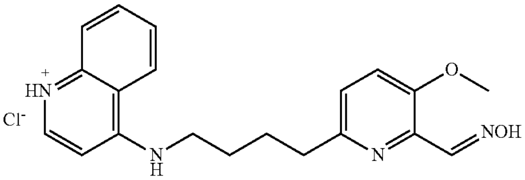

(3aS,4S,6R,6aR)-6-(6-amino-9H-purin-9-yl)-N-(4-(6-(-(hydroxyimino) methyl-5-methoxypyridin-2-yl)but-3-yn-1-yl)-2,2-dimethyltetrahydrofuro [3.4-d][1,3]dioxole-4-carboxamide 72:

72

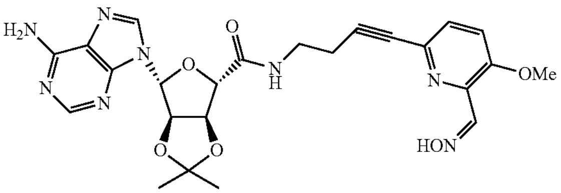

(3aS,4S,6R,6aR)-6-(6-amino-9H-purin-9-yl)-N-(2-(1-((6-(-(hydroxyimino) meth-yl)-pyridin-2-yl)methyl)-1H-1,2,3-trazol-4-yl)ethyl)-2,2-dimethyltetrahydrofuro[3.4-d][1,3]dioxole-4-carboxamide 77:

77

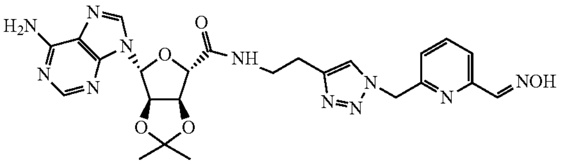

-continued (2S,3S,4R,5R)-5-(6-amino-9H-purin-9-yl)-3,4-dihydroxy-N-(2-(1-((6-(hydroxyimino)methyl)pyridin-2-yl)methyl)-1H-1,2,3-trazol-4-yl) ethyl)tetrahydrofuran-2-carbox-amide. hydrochloride 78:

78

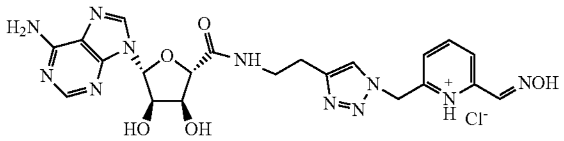

N-(9-((3aR,4R,6R,6aR)-6-(((1-((6-(-(hydroxyimino)methyl)pyridin-2-yl) methyl)-1H-1,2,3-triazol-4-yl)methoxy)methyl)-2,2-dimethyltetrahydrofuro [3,4-d][1,3]dioxol-4-yl)-9H-purin-6-yl)benzamide 79:

79

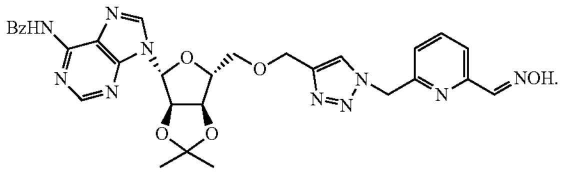

13. Process for preparing a compound of formula (I) according claim 1, wherein —X—Y— is —CH2-CH2- or —C≡C—, comprising performing a Sonogashira coupling reaction between a 6-bromopyridinaldoxime and a compound comprising a terminal alkyne, optionally followed by a reduction step by reaction with hydrogen.

14. A method for treating a disease or condition in a subject in need thereof, comprising administering to said subject a therapeutically effective amount of at least one compound according to claim 1, wherein the disease or condition is:

a nervous and/or respiratory failure due to intoxication with at least one organophosphorous nerve agent; a neurological disease; inflammation; cancer; diabetes; and/or pain.

15. The method of claim 14, wherein the neurological disease is Alzheimer's or Parkinson's disease.

* * * * *